(12) United States Patent
Ouyang et al.

(10) Patent No.: US 8,460,182 B2
(45) Date of Patent: Jun. 11, 2013

(54) METHOD AND APPARATUS FOR HYSTEROSCOPY AND ENDOMETRIAL BIOPSY

(75) Inventors: Xiaolong Ouyang, Palo Alto, CA (US); Paul D. Indman, San Jose, CA (US); Robert K. Deckman, San Bruno, CA (US); Shih-Ping Wang, Los Altos, CA (US)

(73) Assignee: EndoSee Corporaton, Los Altos, CA (US)

( * ) Notice: Subject to any disclaimer, the term of this patent is extended or adjusted under 35 U.S.C. 154(b) by 0 days.

(21) Appl. No.: 13/474,429

(22) Filed: May 17, 2012

(65) Prior Publication Data

US 2012/0289858 A1 Nov. 15, 2012

Related U.S. Application Data

(63) Continuation-in-part of application No. PCT/US2012/034698, filed on Apr. 23, 2012, and a continuation-in-part of application No. PCT/US2011/051982, filed on Sep. 16, 2011, and a (Continued)

(51) Int. Cl.
*A61B 1/00* (2006.01)
*A61B 1/12* (2006.01)
*H04N 7/18* (2006.01)

(52) U.S. Cl.
USPC ........... 600/136; 600/103; 600/131; 600/156; 348/77

(58) Field of Classification Search
USPC ................. 600/104, 105, 127, 129, 135, 136, 600/152, 153, 156, 158, 103, 131, 157, 160, 600/179, 185, 188; 348/77
See application file for complete search history.

(56) References Cited

U.S. PATENT DOCUMENTS

| 4,475,539 A | 10/1984 | Konomura |
| 5,823,940 A | 10/1998 | Newman |

(Continued)

FOREIGN PATENT DOCUMENTS

| WO | WO 94/08512 | 4/1994 |
| WO | WO 2008/048688 A2 | 4/2008 |

(Continued)

OTHER PUBLICATIONS

EndoSee Corporation Brochure www.endosee.com Apr. 2013.

(Continued)

*Primary Examiner* — Alireza Nia
(74) *Attorney, Agent, or Firm* — Cooper & Dunham LLP

(57) ABSTRACT

Methods and devices are described for performing a combined hysteroscopy and endometrial sampling. Techniques for improving visual images include forward facing fluid ports for clearing tissue debris and LED positioning and design. Manufacturability is improved through separately formed tip and shaft pieces. User interface features are described including user-friendly handle-mounted buttons as well the use of an interactive integrated touch screen display. The handle and display can be mated to a docking station for storage and recharging batteries.

18 Claims, 72 Drawing Sheets

Related U.S. Application Data continuation-in-part of application No. 12/911,297, filed on Oct. 25, 2010.

(60) Provisional application No. 61/623,376, filed on Apr. 12, 2012, provisional application No. 61/611,182, filed on Mar. 15, 2012, provisional application No. 61/600,593, filed on Feb. 18, 2012, provisional application No. 61/599,981, filed on Feb. 17, 2012, provisional application No. 61/570,816, filed on Dec. 14, 2011, provisional application No. 61/556,167, filed on Nov. 4, 2011, provisional application No. 61/555,470, filed on Nov. 3, 2011, provisional application No. 61/550,391, filed on Oct. 22, 2011, provisional application No. 61/544,280, filed on Oct. 7, 2011, provisional application No. 61/539,736, filed on Sep. 27, 2011, provisional application No. 61/515,092, filed on Aug. 4, 2011, provisional application No. 61/506,074, filed on Jul. 9, 2011, provisional application No. 61/494,400, filed on Jun. 7, 2011, provisional application No. 61/490,029, filed on May 25, 2011, provisional application No. 61/485,601, filed on May 12, 2011, provisional application No. 61/482,309, filed on May 4, 2011, provisional application No. 61/482,200, filed on May 3, 2011, provisional application No. 61/476,754, filed on Apr. 18, 2011, provisional application No. 61/453,533, filed on Mar. 16, 2011, provisional application No. 61/450,115, filed on Mar. 7, 2011, provisional application No. 61/444,098, filed on Feb. 17, 2011, provisional application No. 61/437,687, filed on Jan. 30, 2011, provisional application No. 61/431,316, filed on Jan. 10, 2011, provisional application No. 61/429,093, filed on Dec. 31, 2010, provisional application No. 61/418,248, filed on Nov. 30, 2010, provisional application No. 61/415,771, filed on Nov. 19, 2010, provisional application No. 61/324,961, filed on Apr. 16, 2010.

(56) References Cited

U.S. PATENT DOCUMENTS

| | | | |
|---|---|---|---|
| 5,879,289 | A | 3/1999 | Yarushi et al. |
| 5,929,901 | A | 7/1999 | Adair et al. |
| 5,986,693 | A | 11/1999 | Adair et al. |
| 6,043,839 | A | 3/2000 | Adair et al. |
| 6,211,904 | B1 | 4/2001 | Adair et al. |
| 6,275,855 | B1 | 8/2001 | Johnson |
| 6,310,642 | B1 | 10/2001 | Adair et al. |
| 6,554,765 | B1 | 4/2003 | Yarushi et al. |
| 6,982,740 | B2 | 1/2006 | Adair et al. |
| 7,030,904 | B2 | 4/2006 | Adair et al. |
| 7,783,133 | B2 | 8/2010 | Dunki-Jacobs et al. |
| 7,794,409 | B2 * | 9/2010 | Damarati ............ 600/565 |
| 7,846,107 | B2 | 12/2010 | Hoffman et al. |
| 7,959,561 | B2 | 6/2011 | Akui et al. |
| 8,189,043 | B2 * | 5/2012 | Schneider et al. ............ 348/82 |
| 2004/0220478 | A1 | 11/2004 | Wallace et al. |
| 2006/0058703 | A1 | 3/2006 | Huenerbein |
| 2006/0184187 | A1 | 8/2006 | Surti |
| 2006/0258955 | A1 * | 11/2006 | Hoffman et al. ............ 600/564 |
| 2007/0129604 | A1 * | 6/2007 | Hatcher et al. ............ 600/136 |
| 2007/0265492 | A1 | 11/2007 | Sonnenschein et al. |
| 2008/0076966 | A1 | 3/2008 | Isaacson |
| 2008/0097469 | A1 | 4/2008 | Gruber et al. |
| 2008/0097470 | A1 | 4/2008 | Gruber et al. |
| 2008/0108869 | A1 | 5/2008 | Sanders et al. |
| 2008/0132763 | A1 | 6/2008 | Isaacson |
| 2008/0243031 | A1 | 10/2008 | Seibel et al. |
| 2010/0030020 | A1 | 2/2010 | Sanders et al. |
| 2010/0262000 | A1 | 10/2010 | Wallace et al. |
| 2010/0284580 | A1 | 11/2010 | Ouyang et al. |
| 2011/0009694 | A1 | 1/2011 | Schultz et al. |

FOREIGN PATENT DOCUMENTS

| | | |
|---|---|---|
| WO | WO 2012/060932 | 5/2012 |
| WO | WO 2012/151073 | 11/2012 |

OTHER PUBLICATIONS

Ethicon Versascope Brochure VS001R2, S/06.
U.S. Appl. No, 12/911,297, filed Oct. 25, 2010, Ouyang.

* cited by examiner

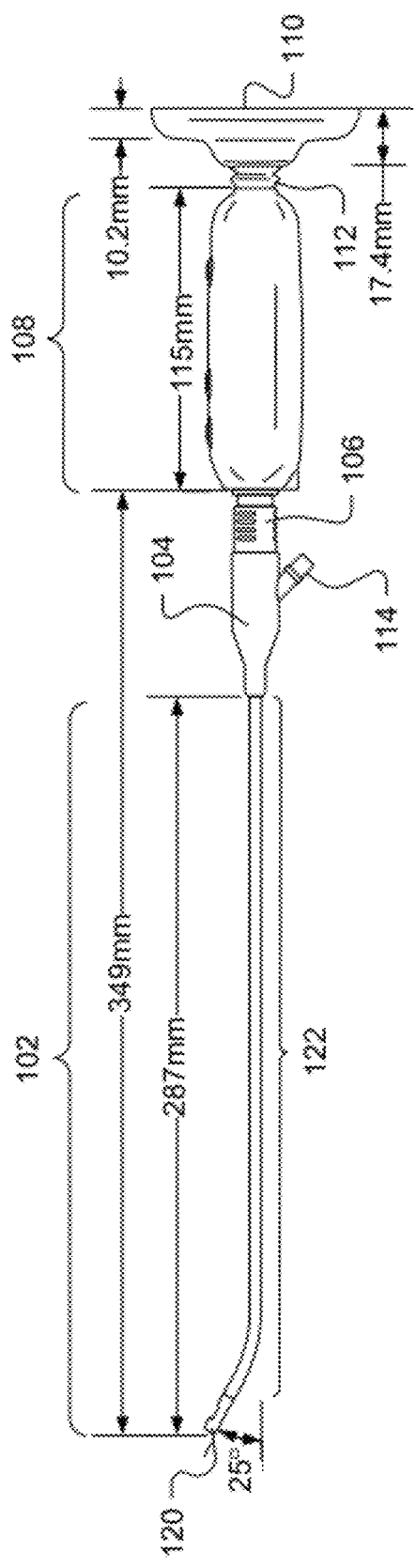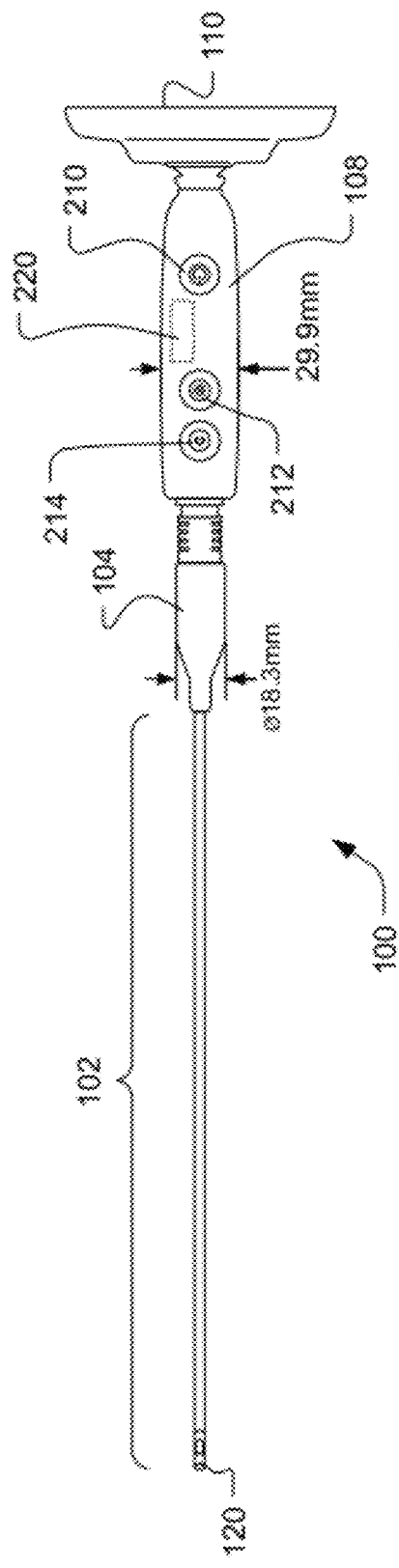

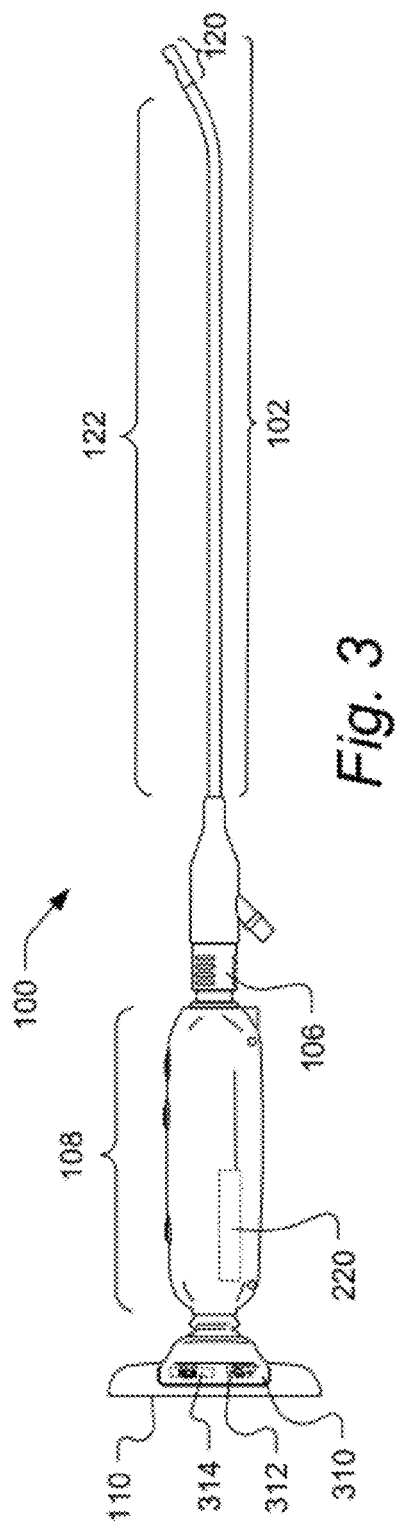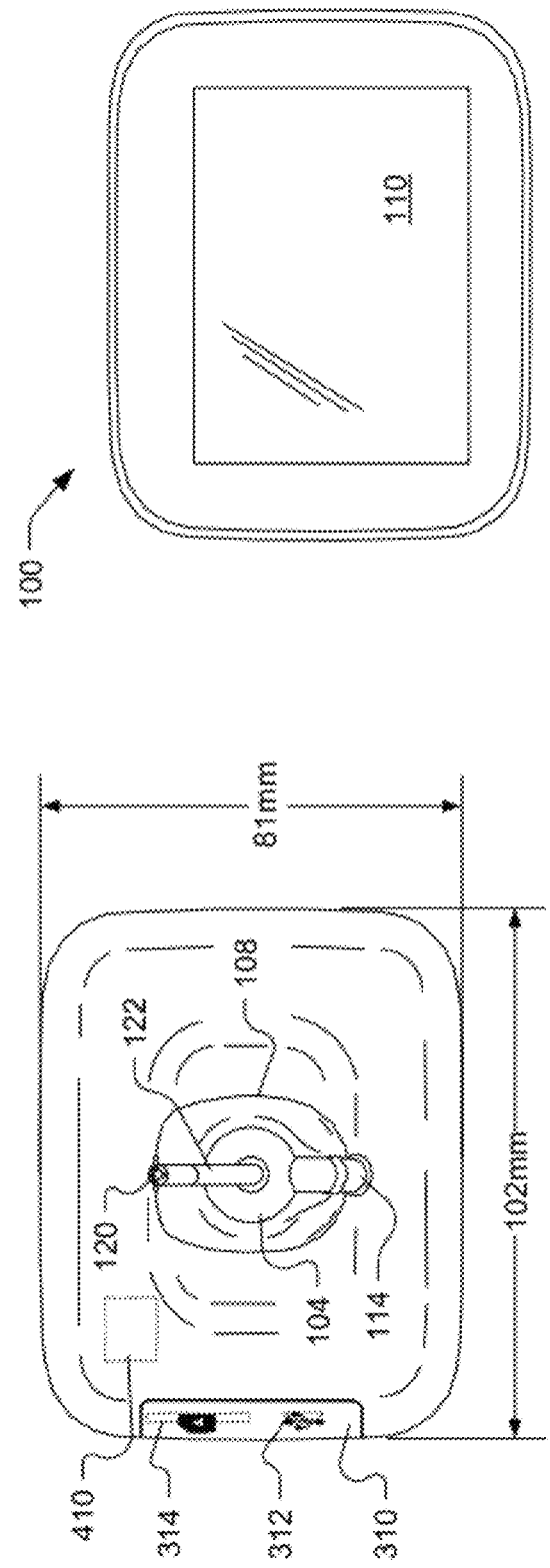

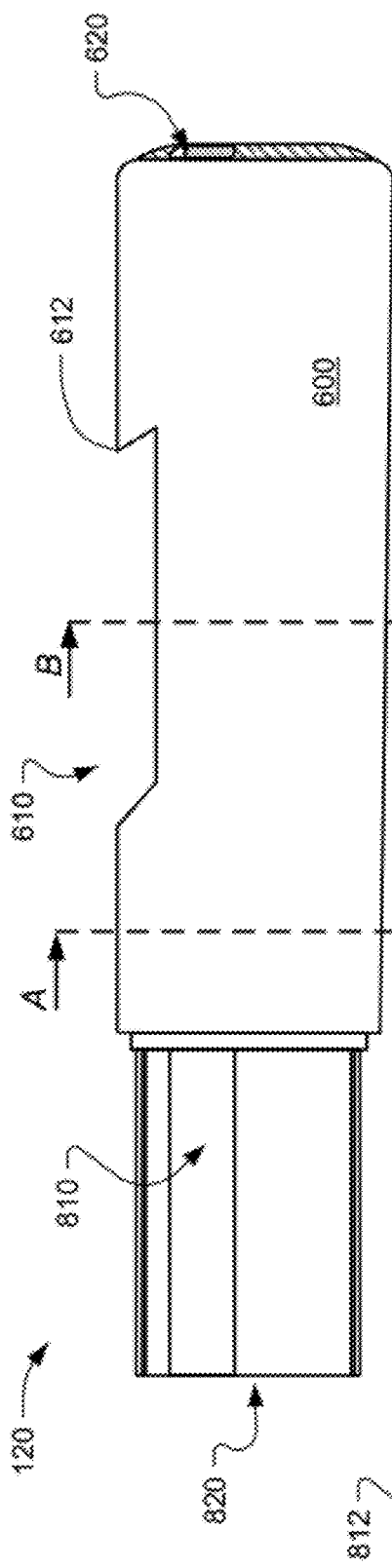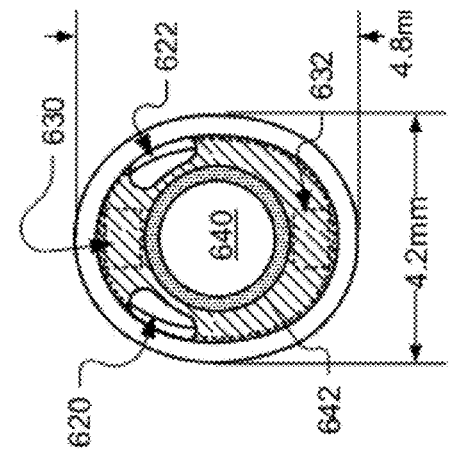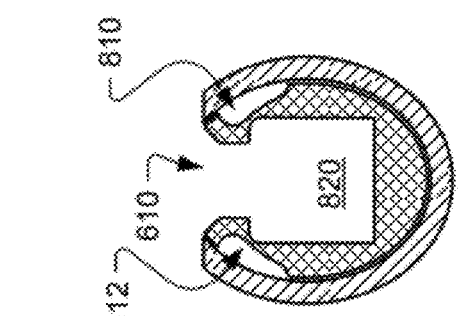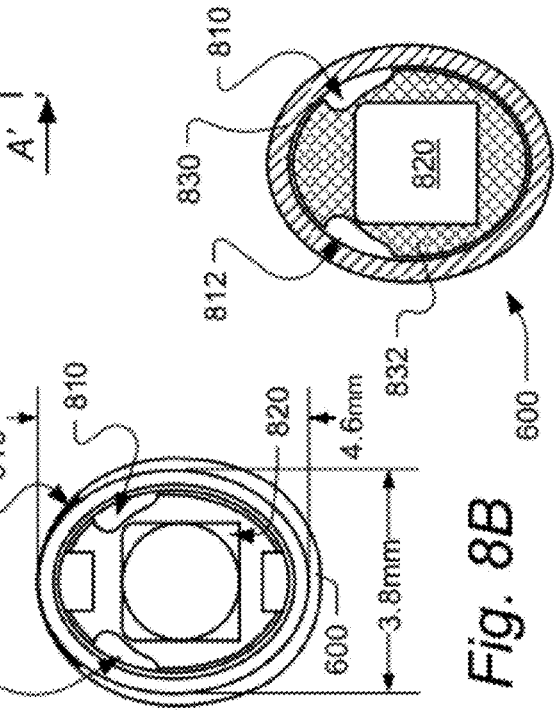
Fig. 8A
Fig. 8B
Fig. 8C A-A'
Fig. 8D B-B'
Fig. 8E

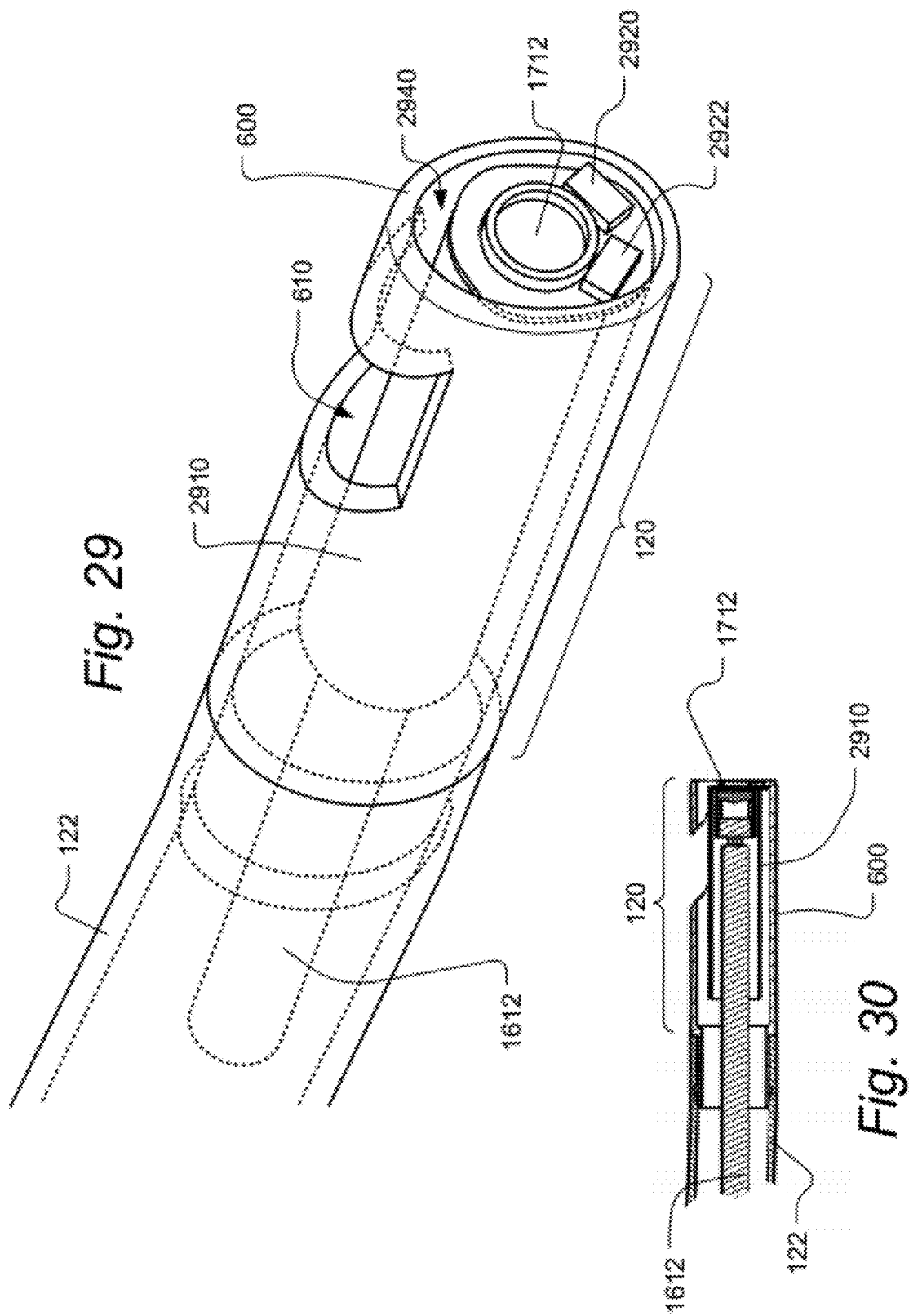

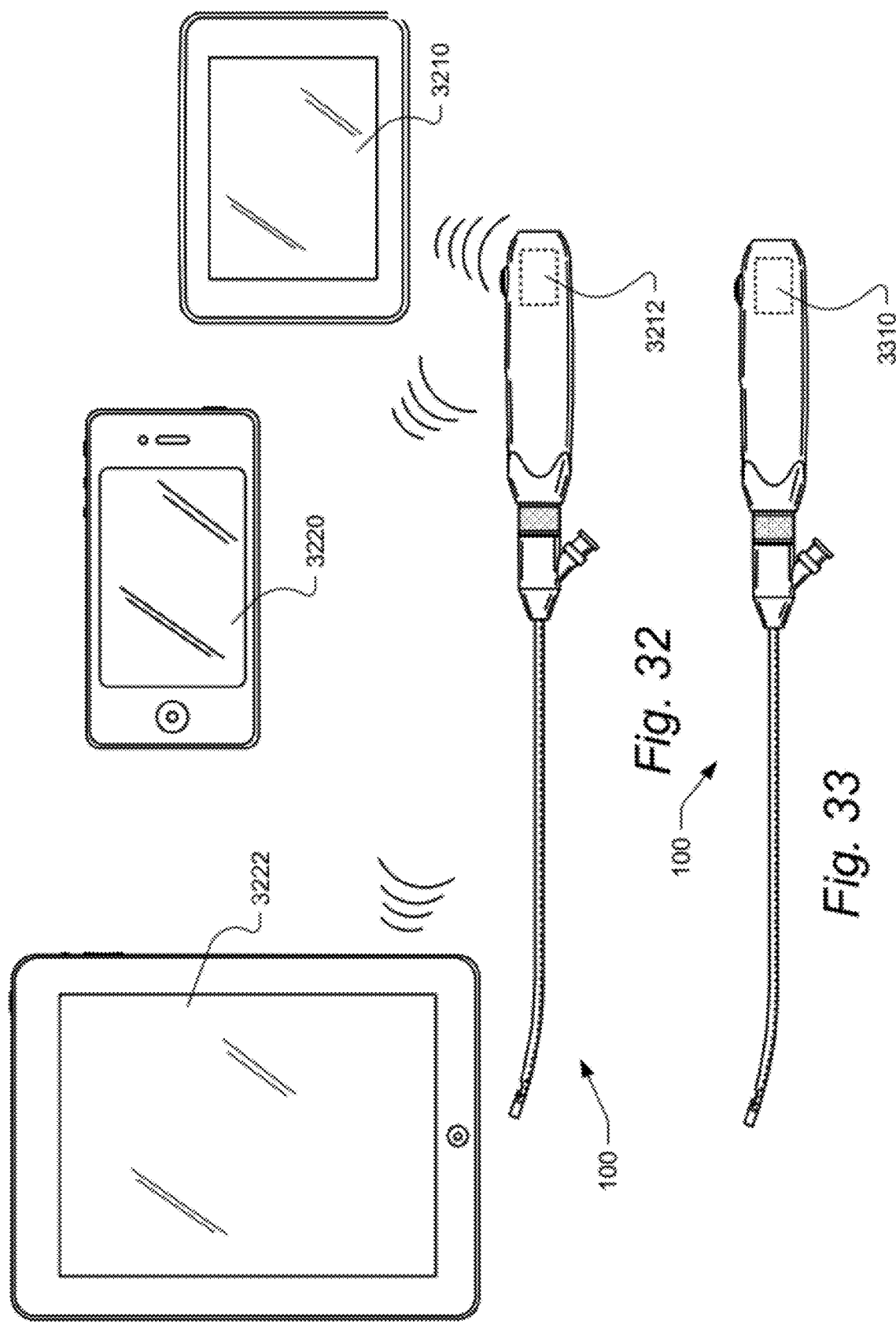

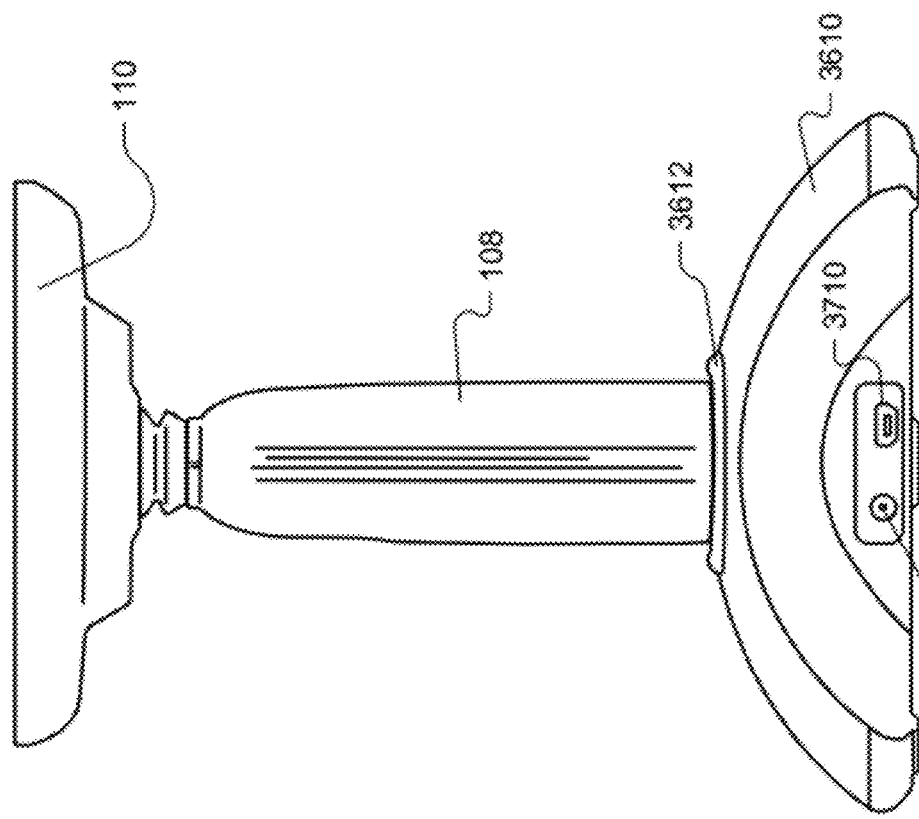
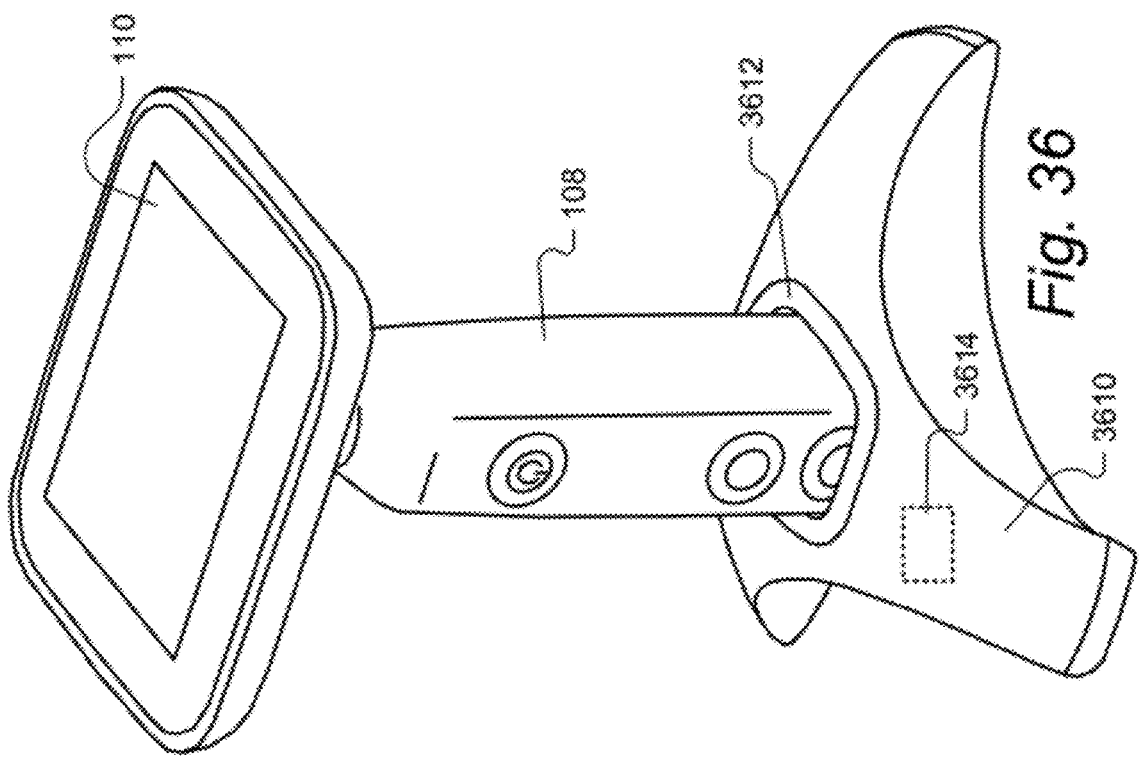

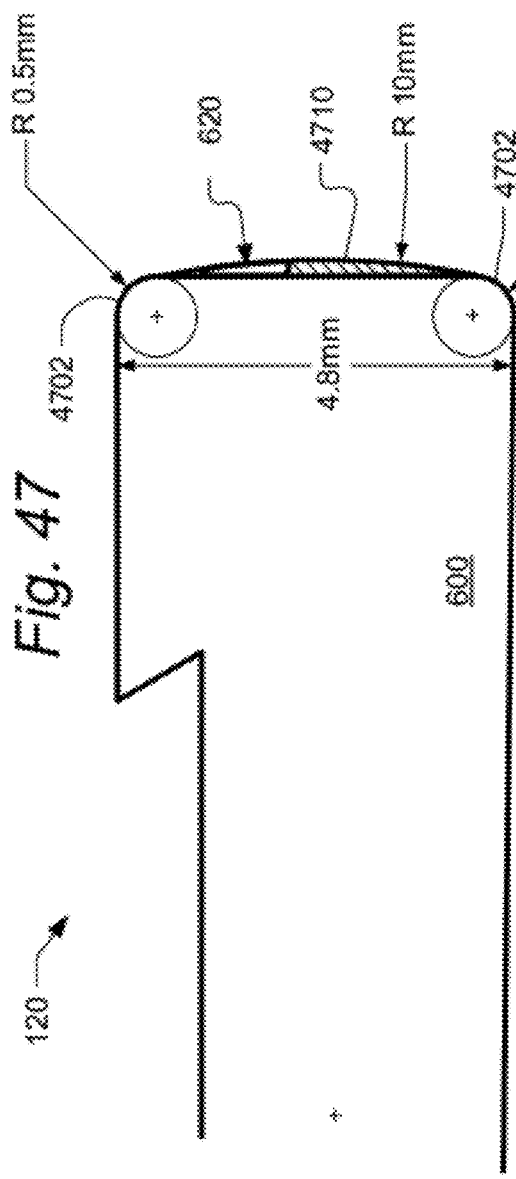
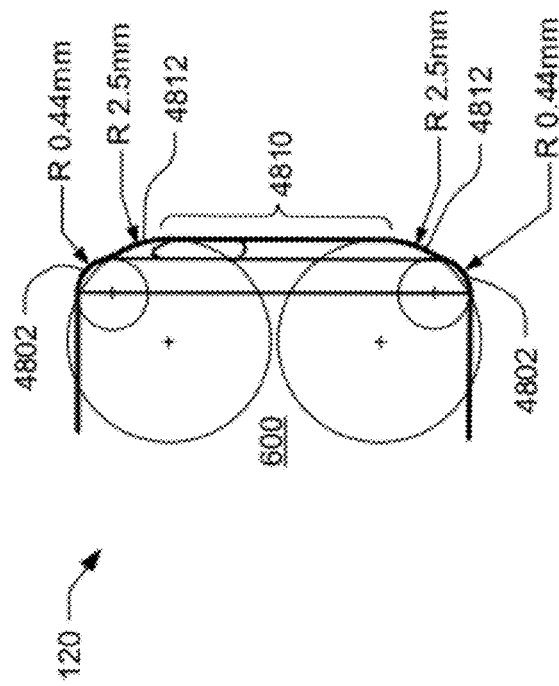

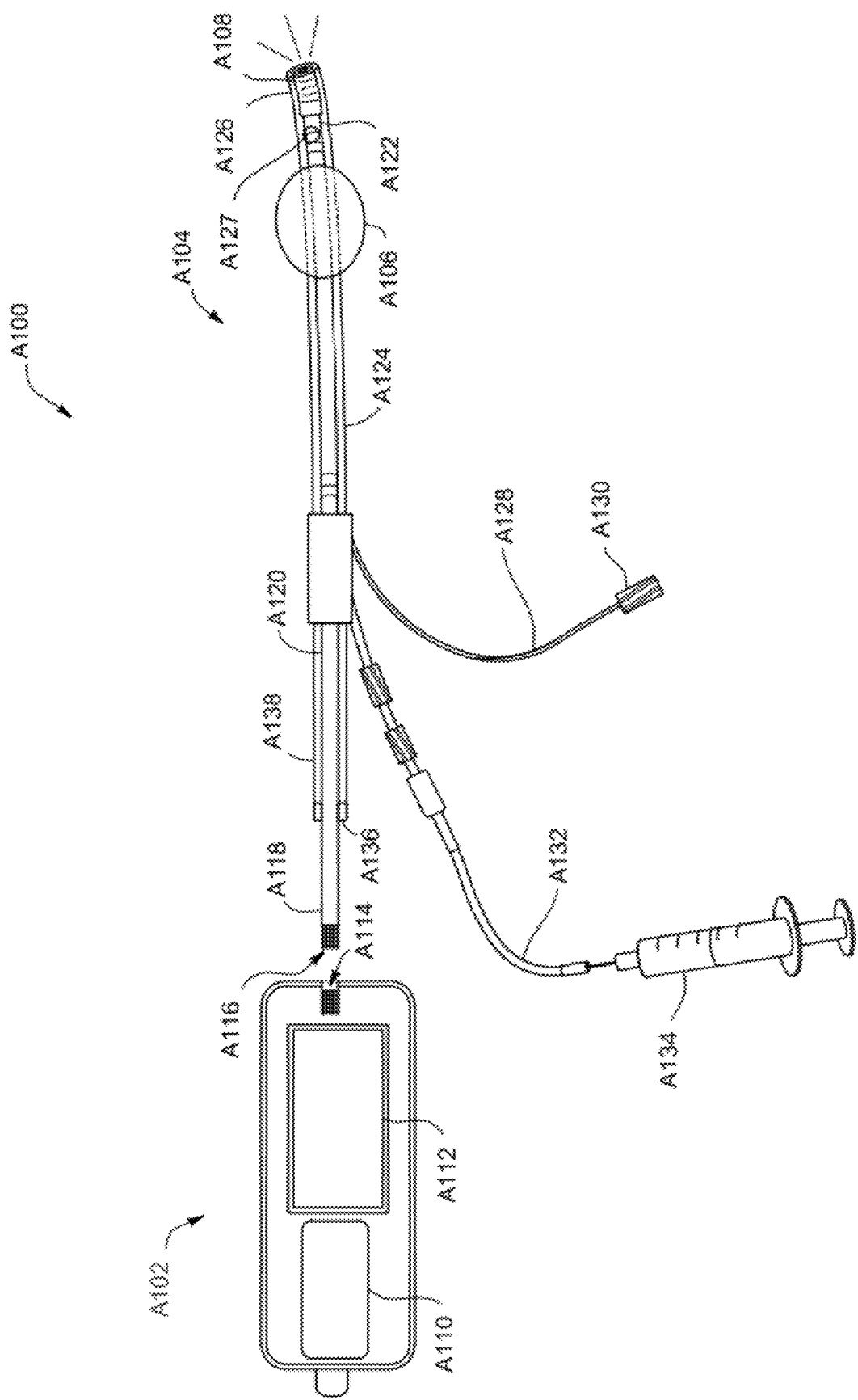
Fig. A1

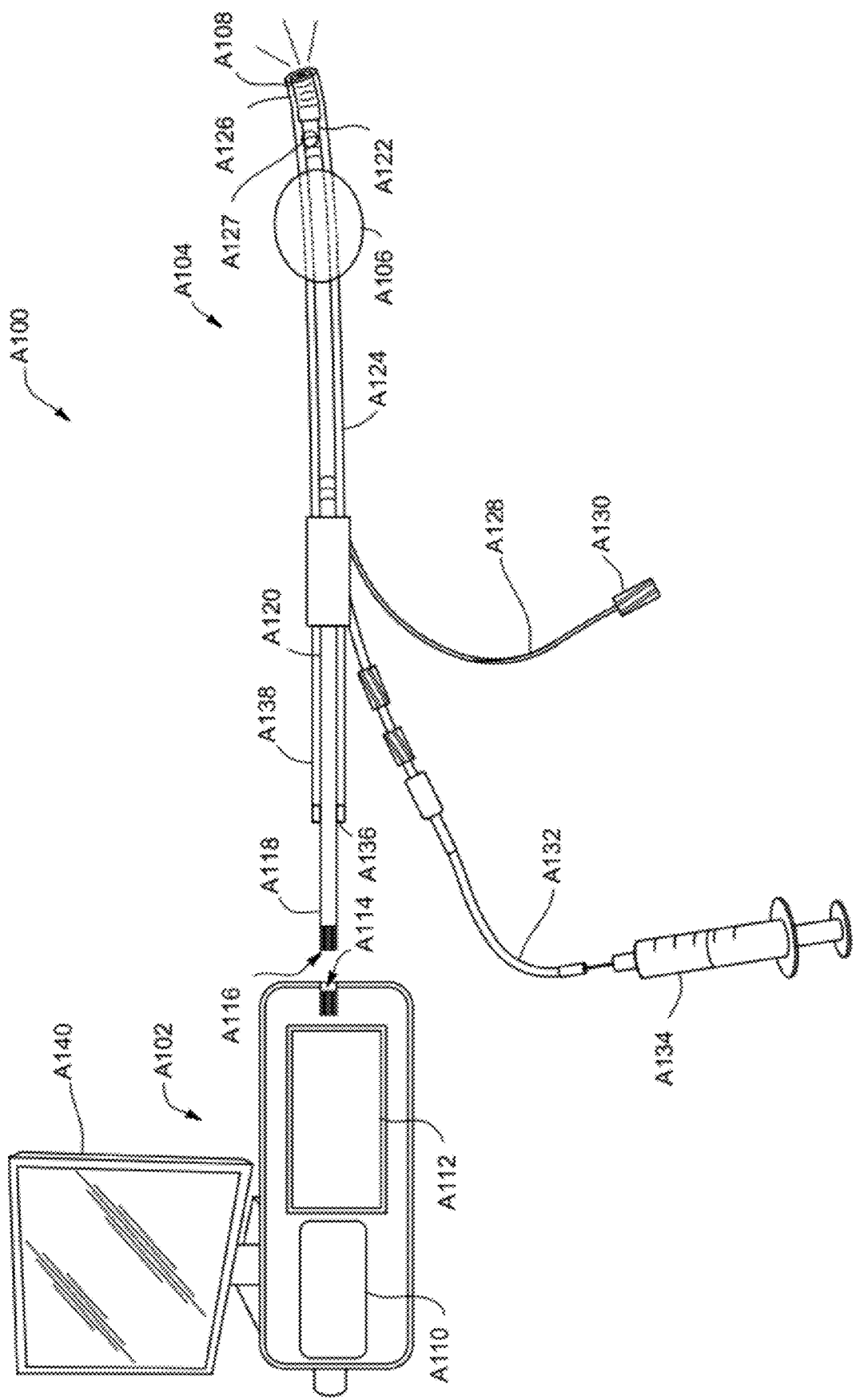
Fig. A 2

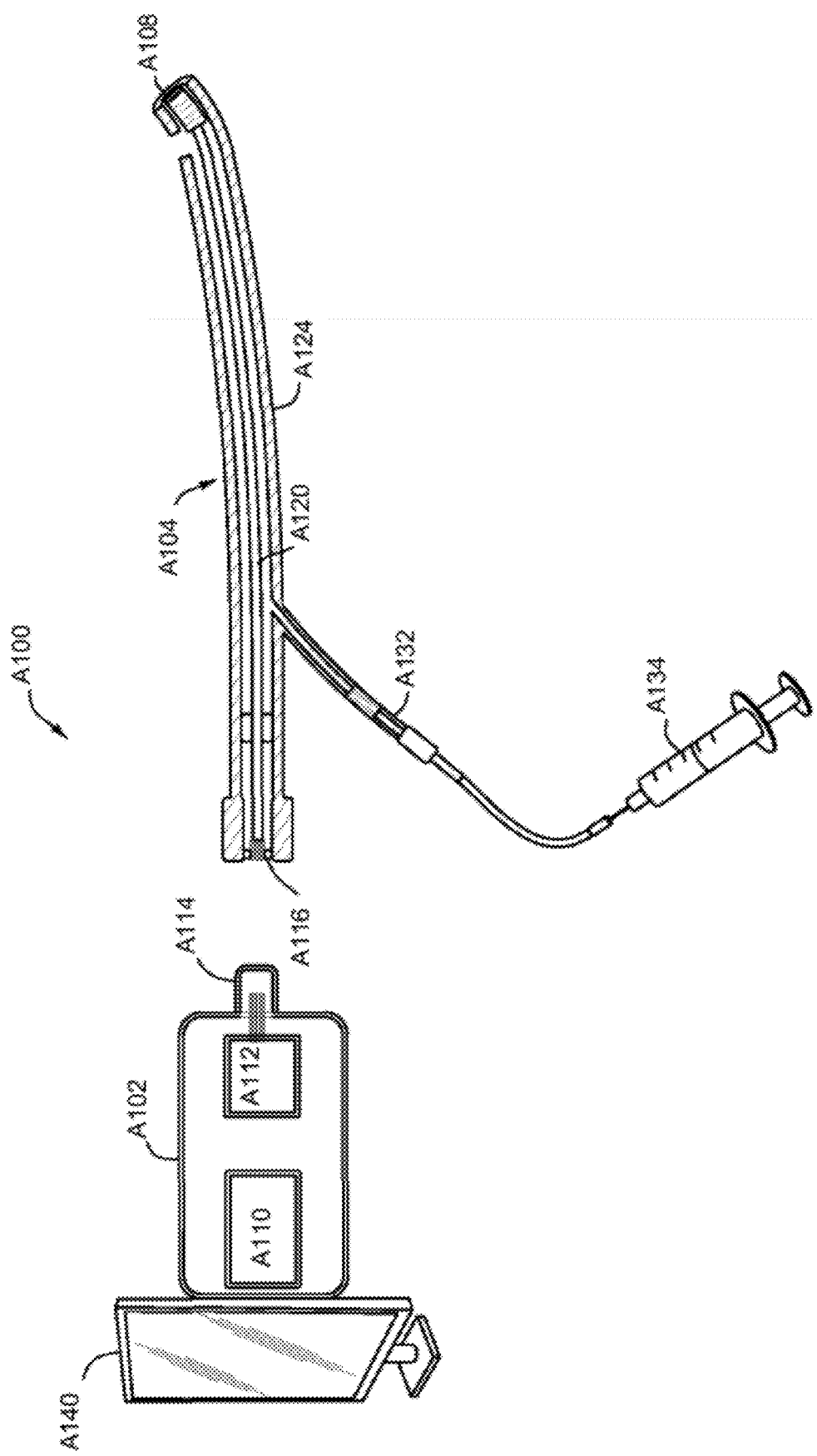
Fig. A 3

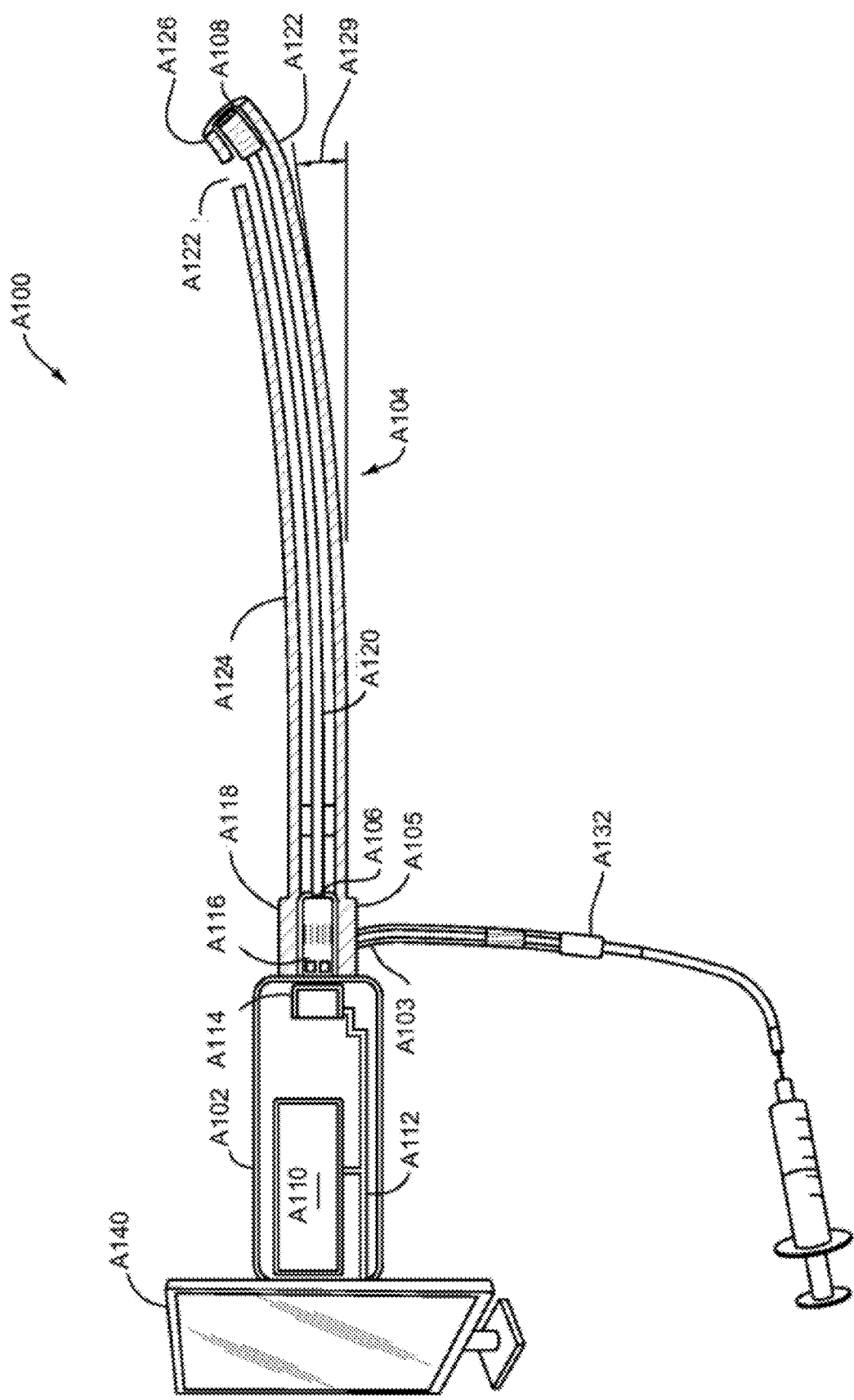
Fig. A 4 A

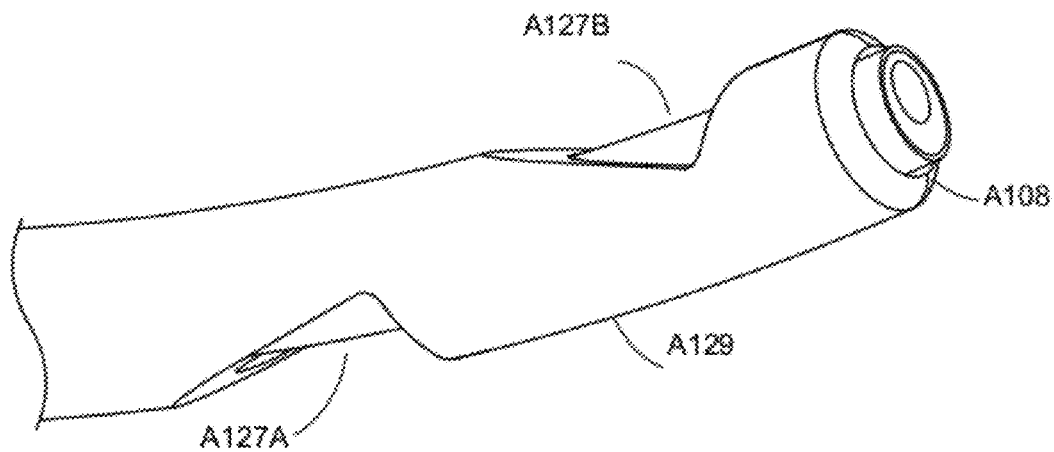
Fig. A 4 B
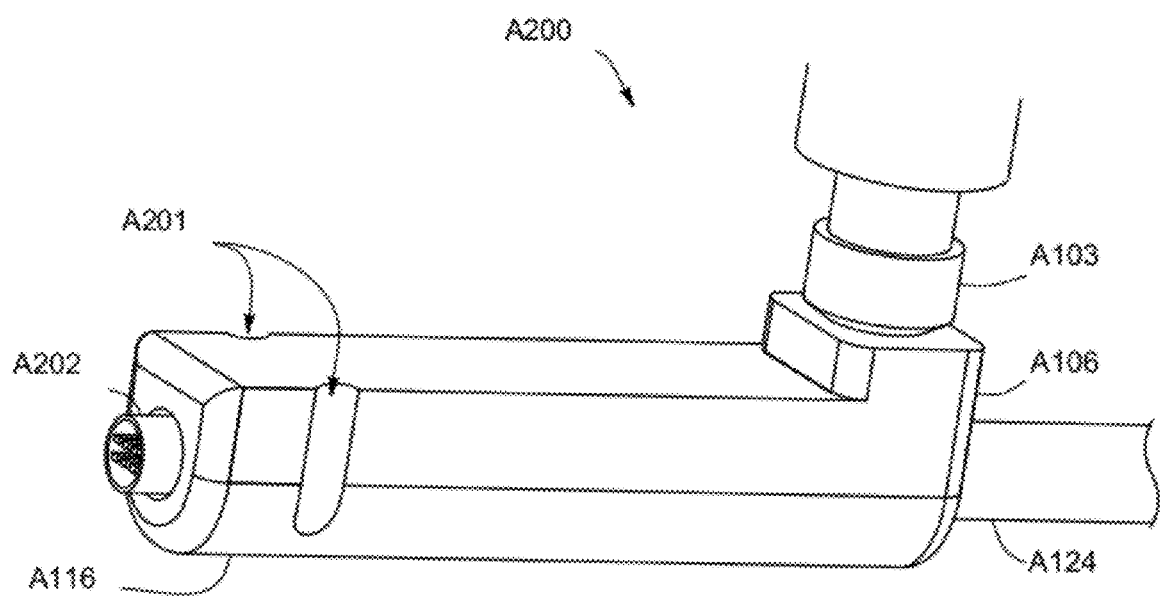
Fig. A 5 A

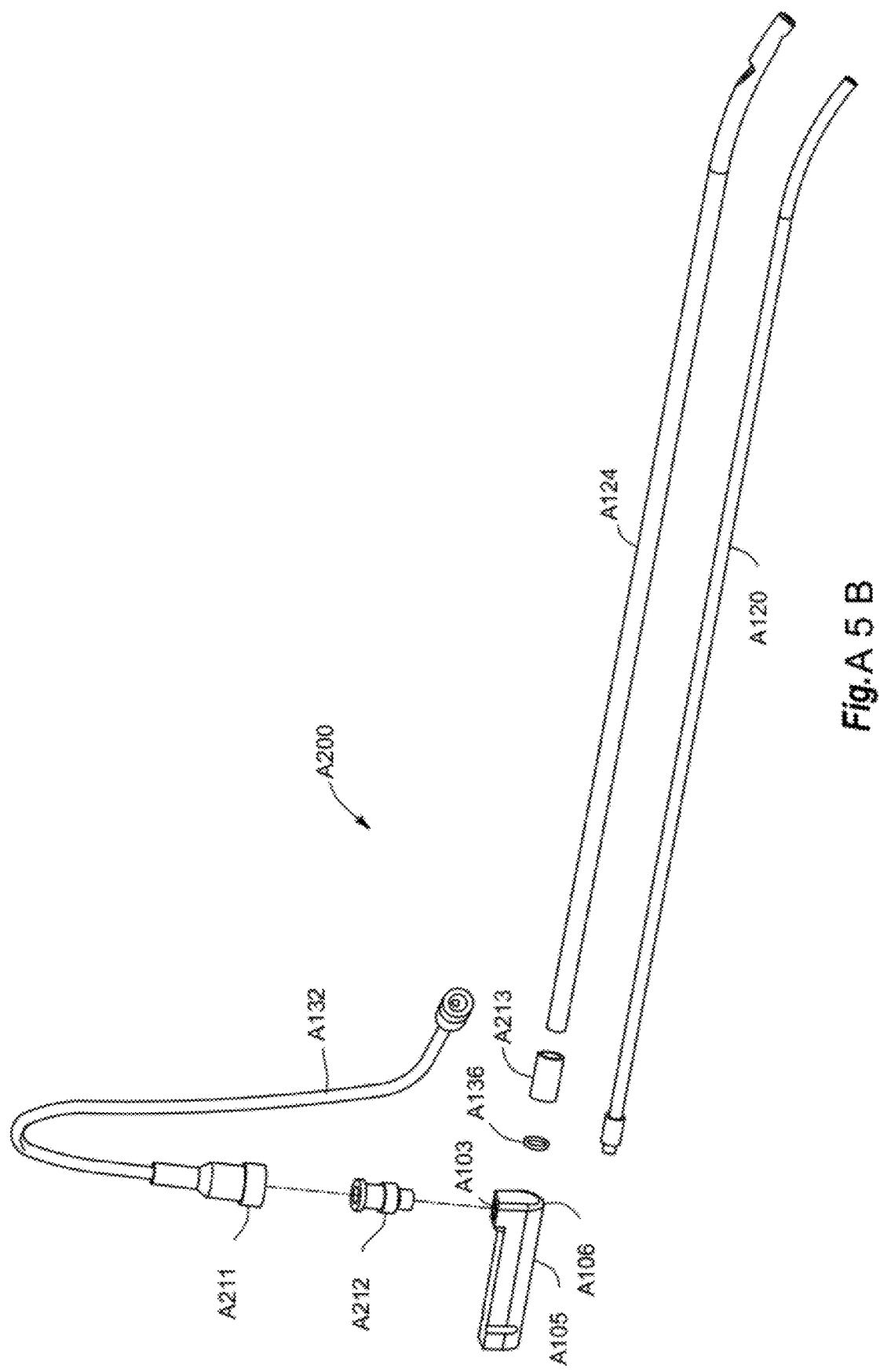
Fig.A 5 B

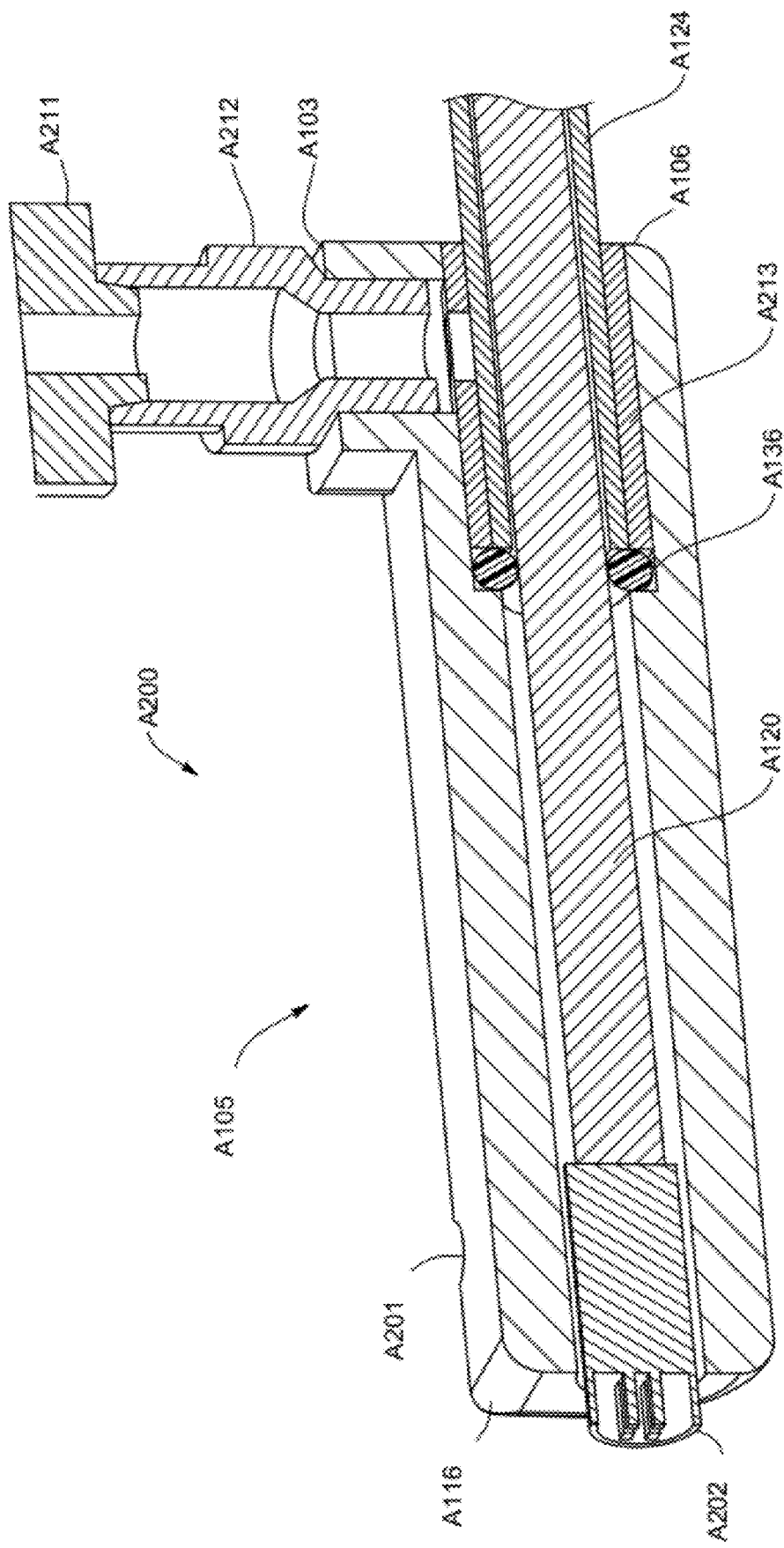
Fig. A 5 C

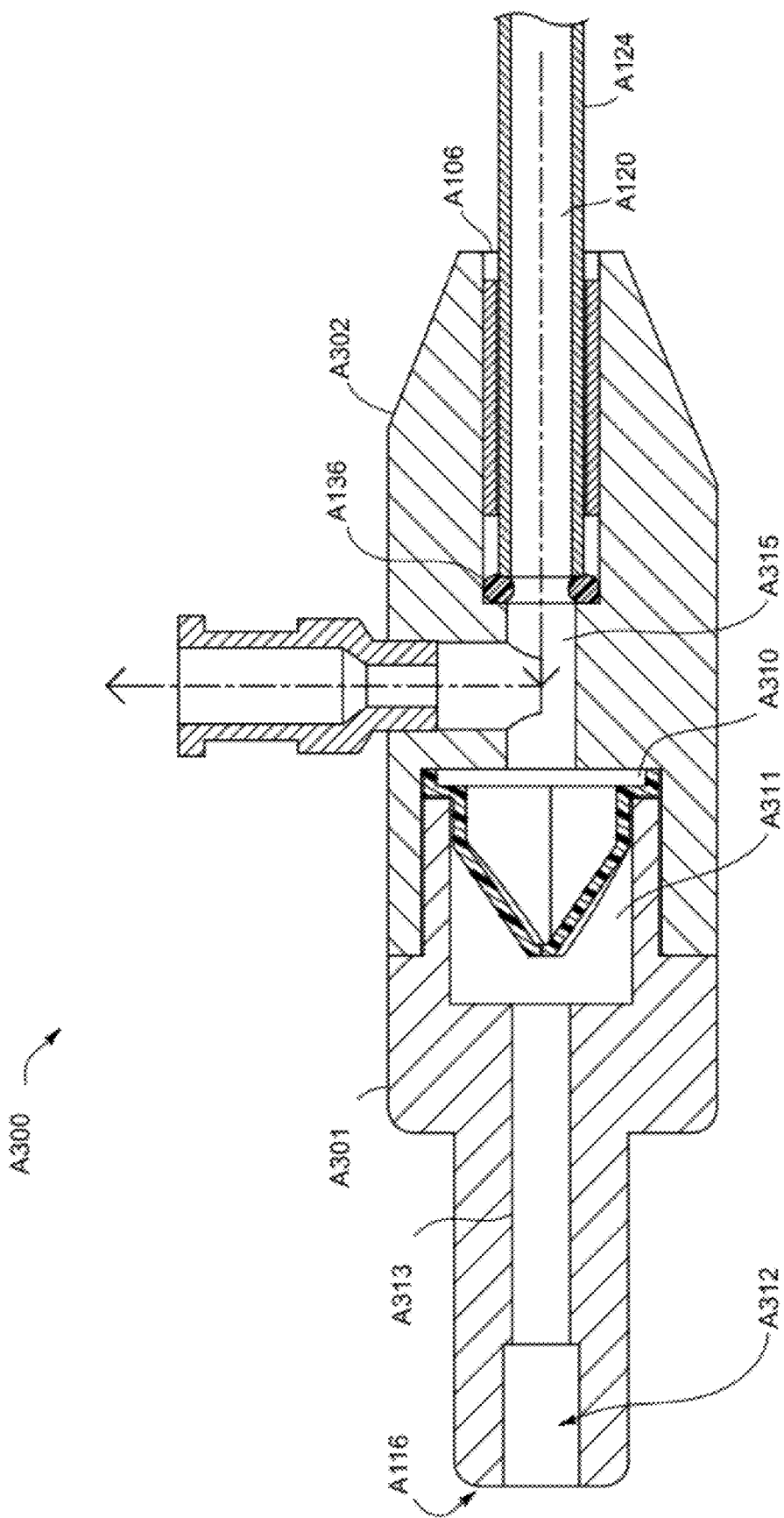
Fig. A 6 A

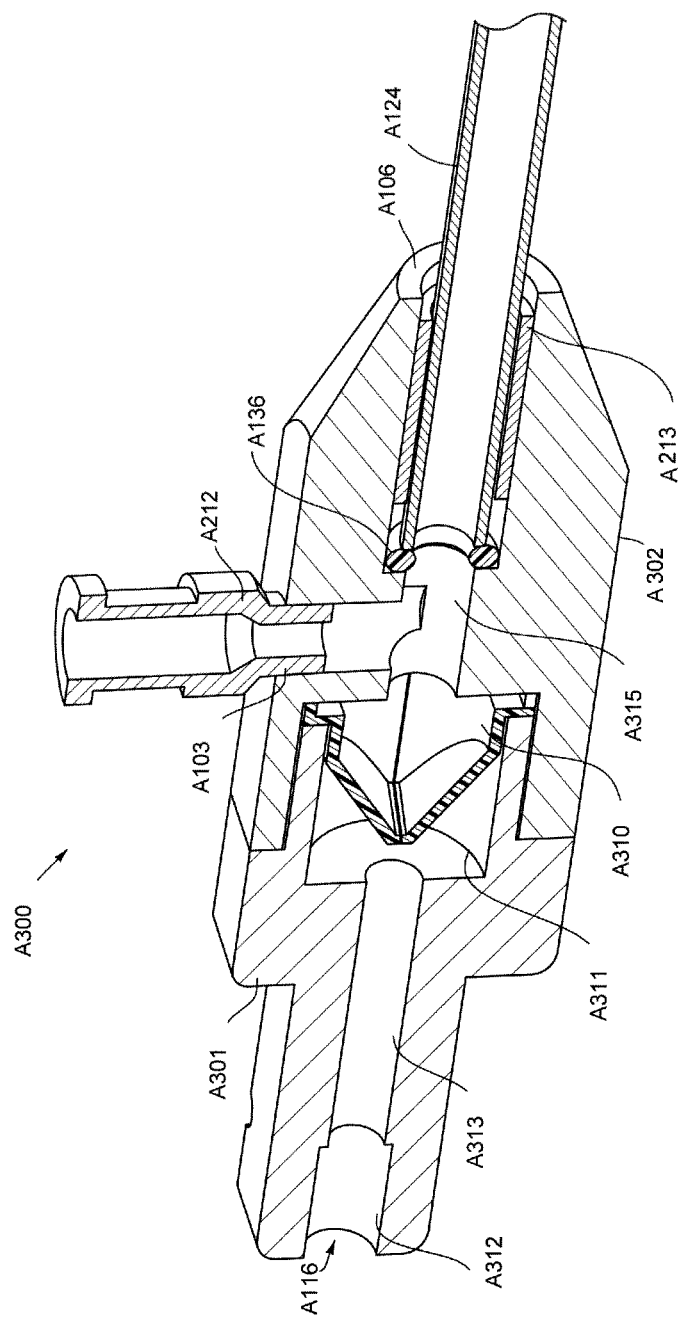
Fig. A 6 B

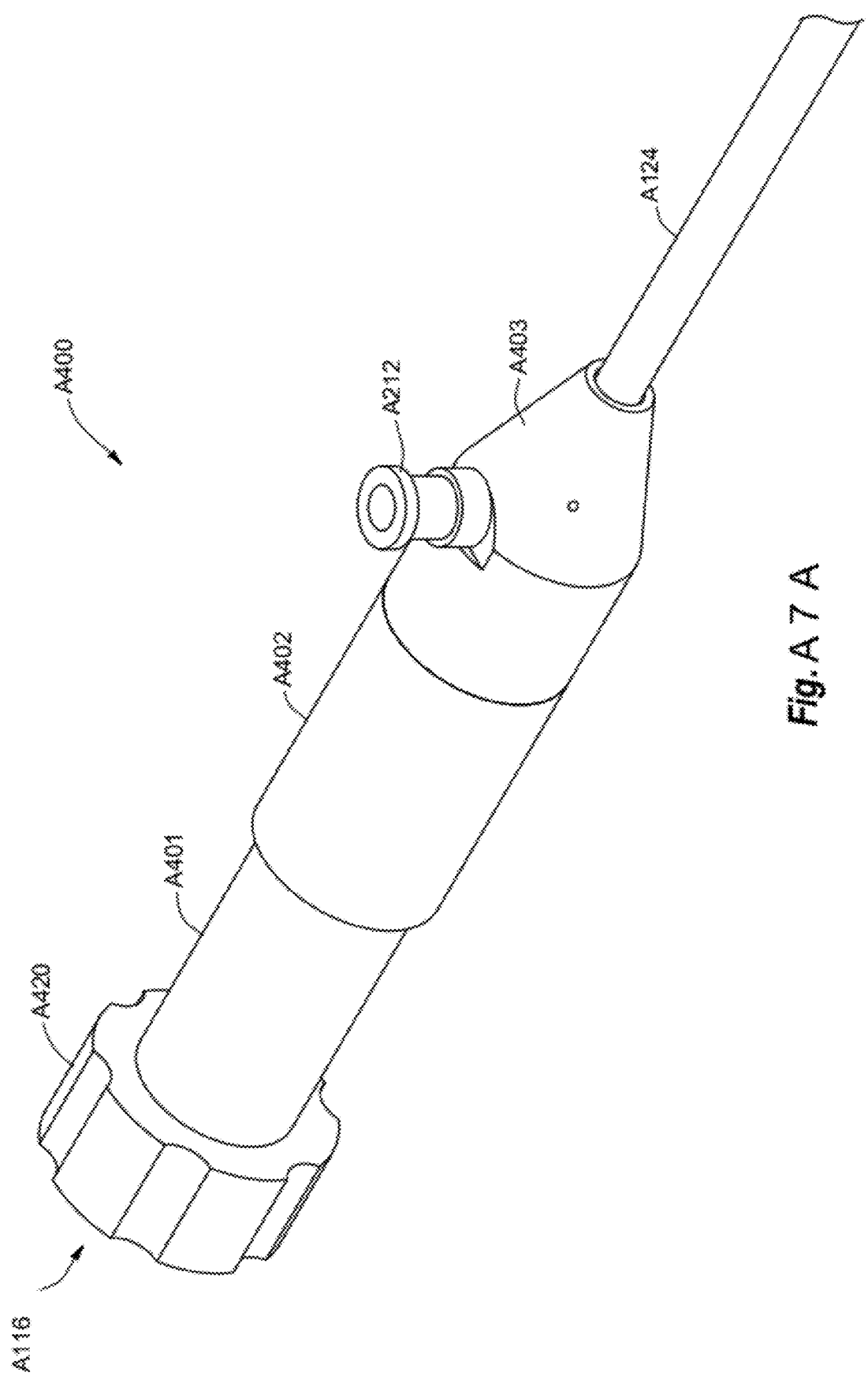
Fig. A7A

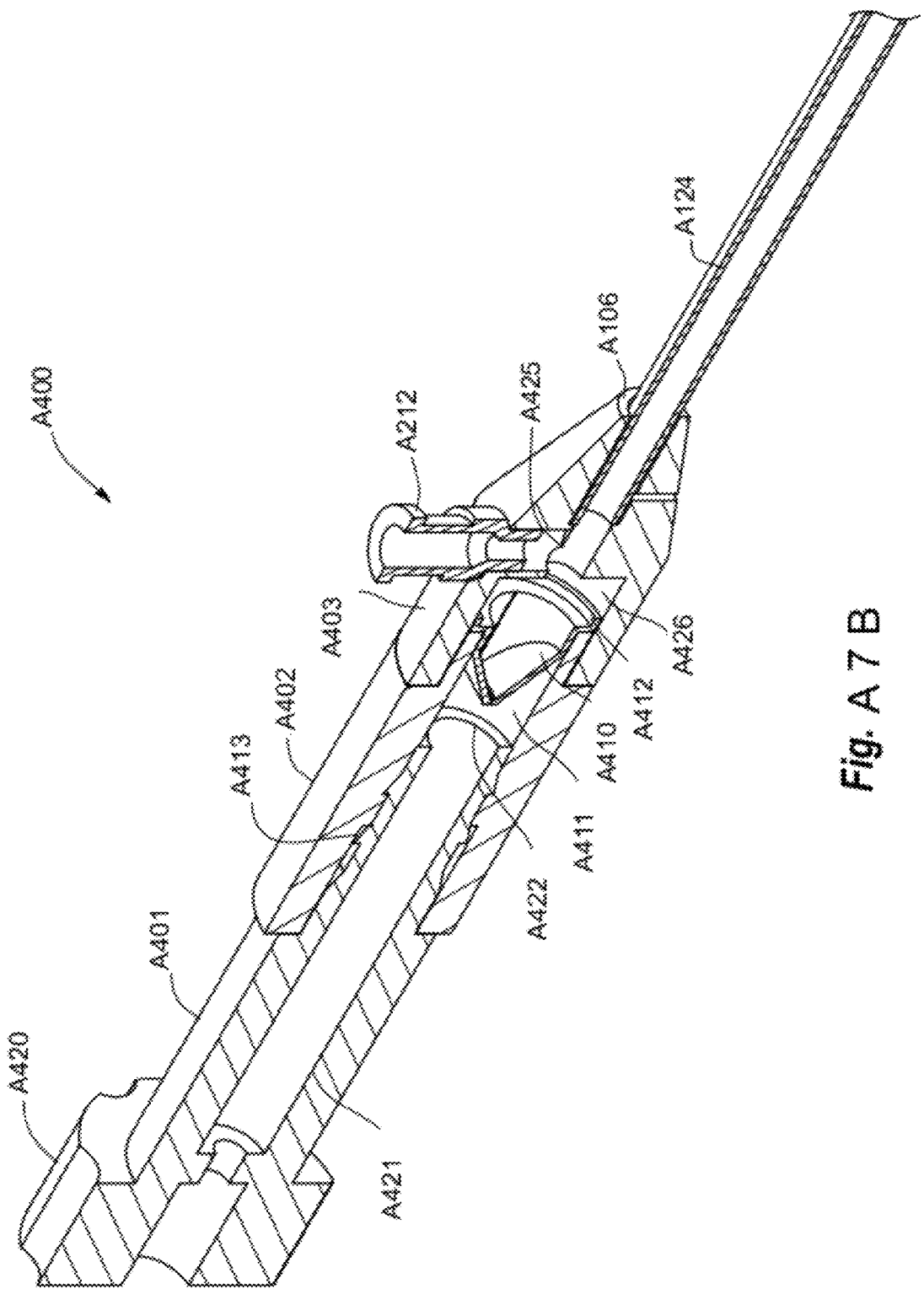
Fig. A 7 B

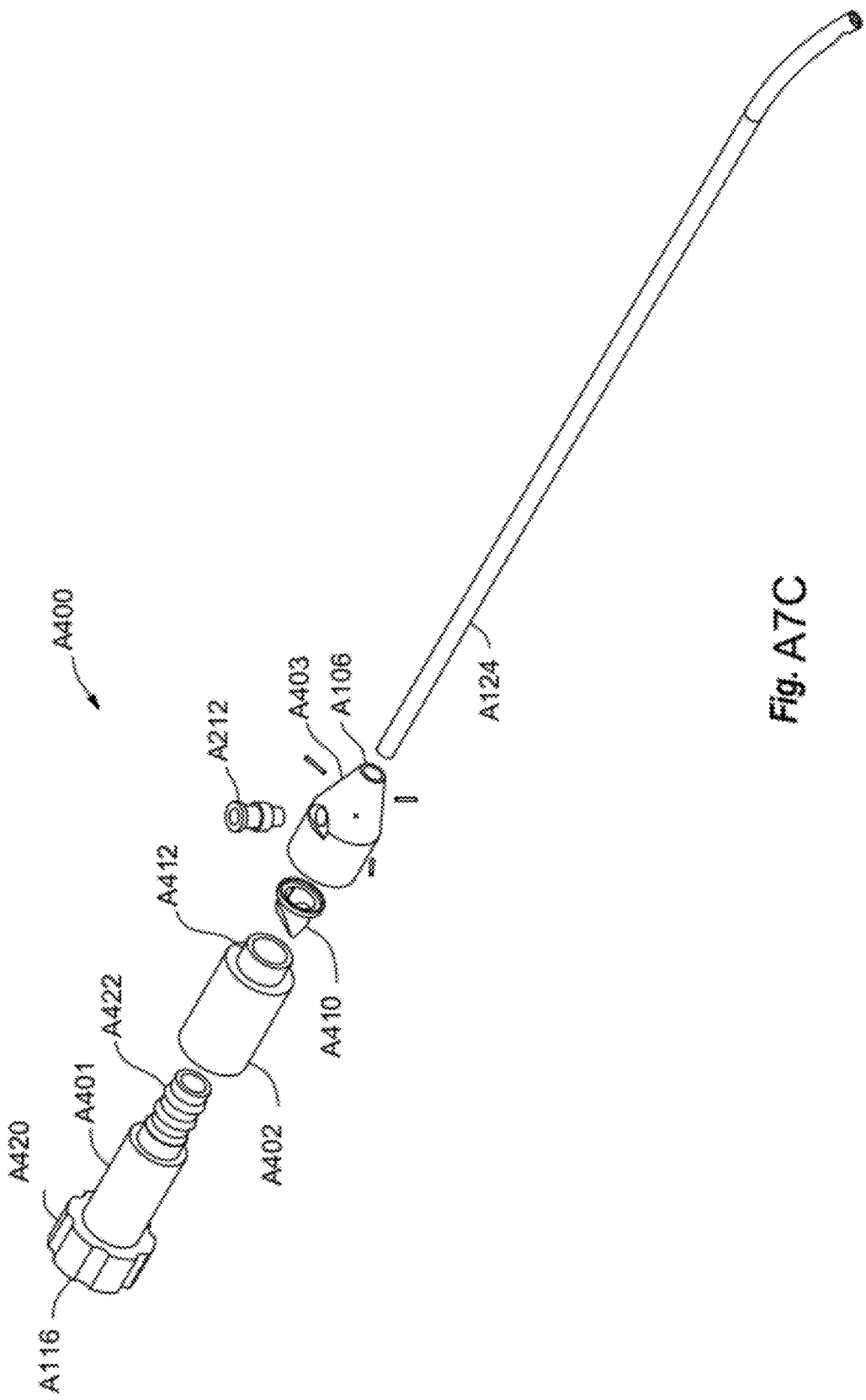
Fig. A7C

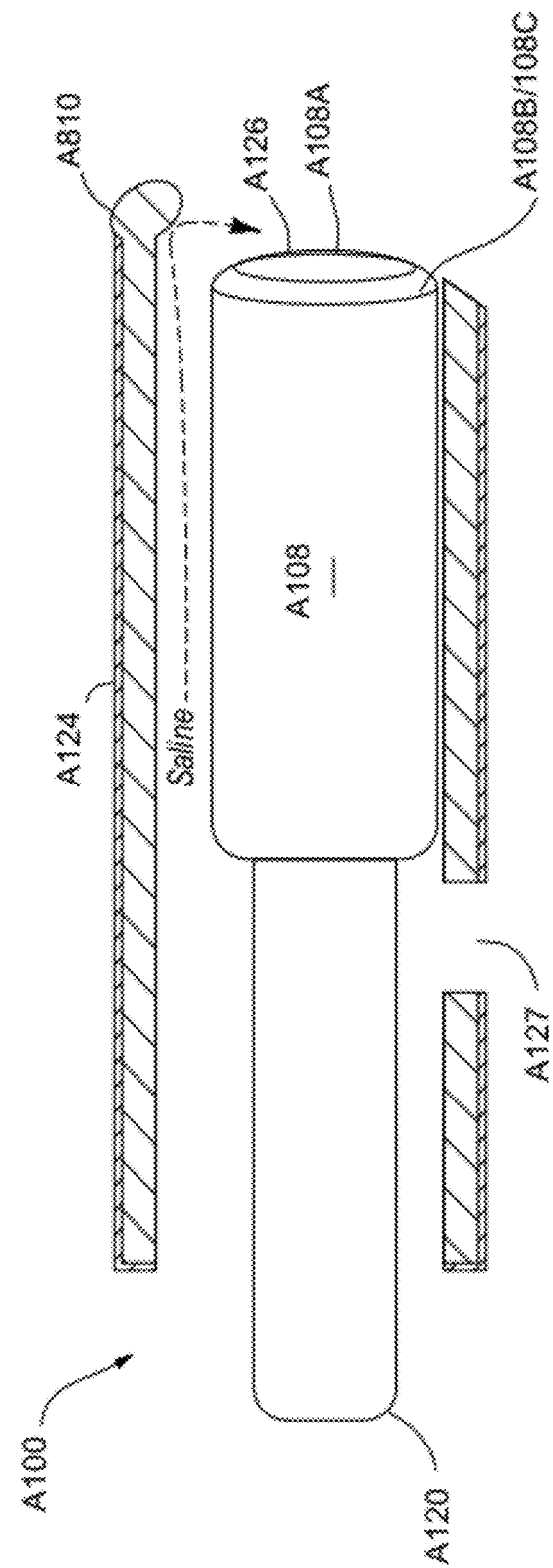
Fig. A8

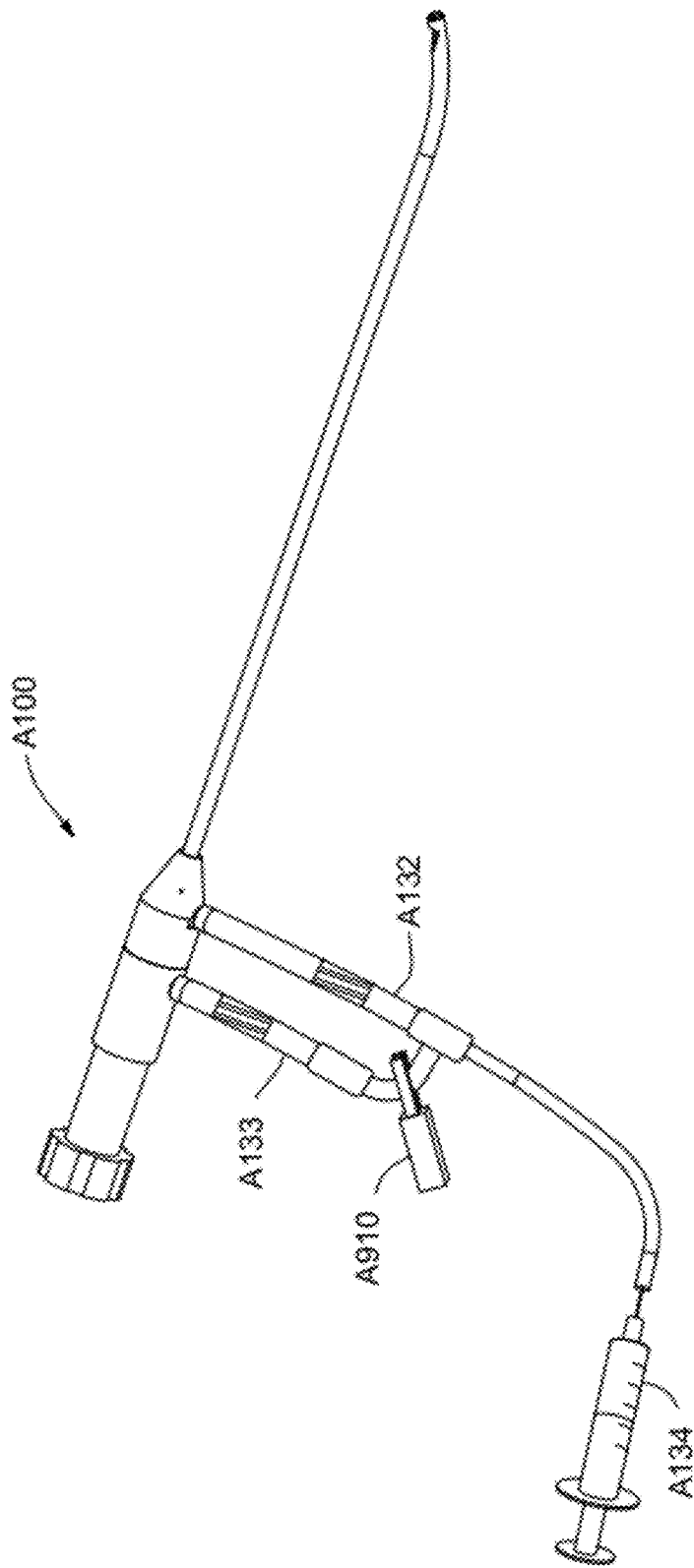
Fig. A9A

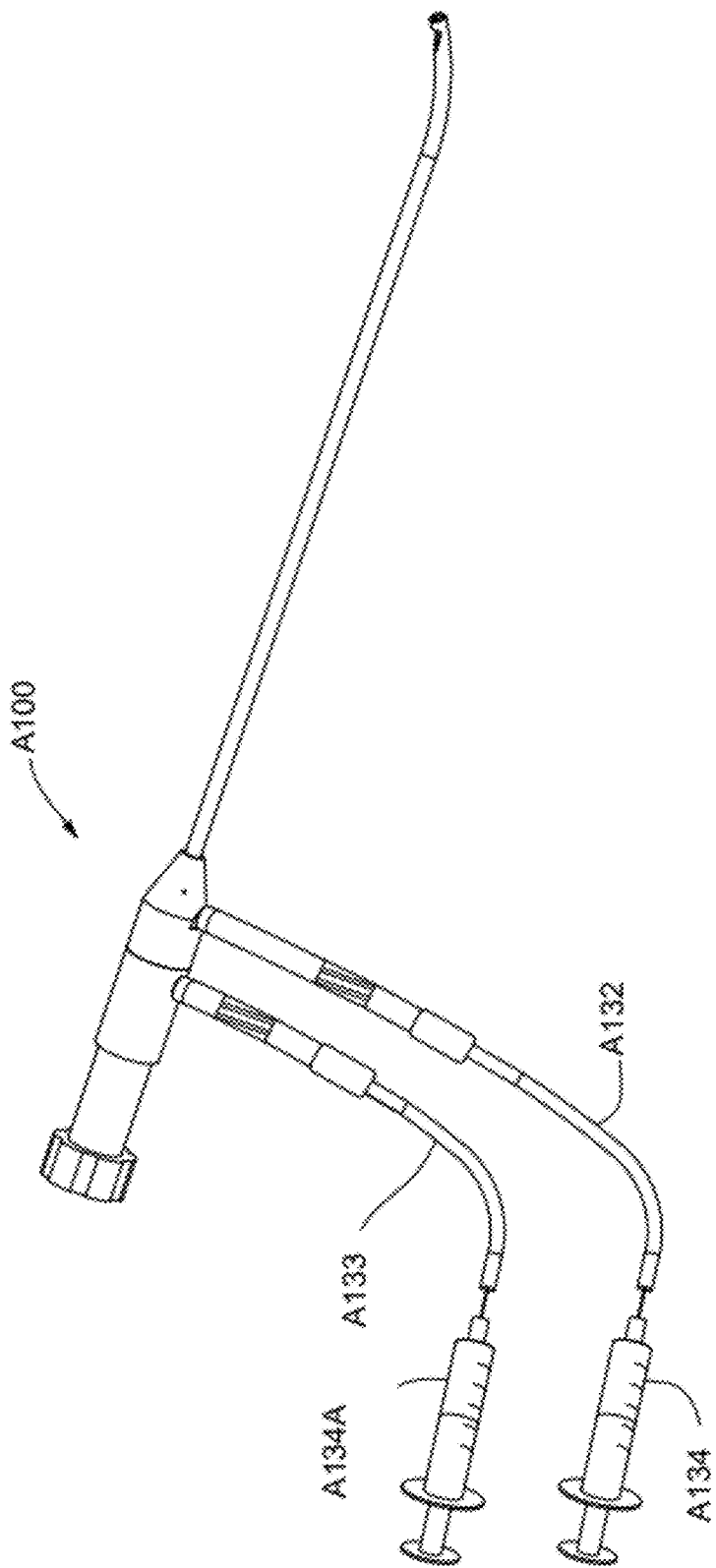
Fig. A10

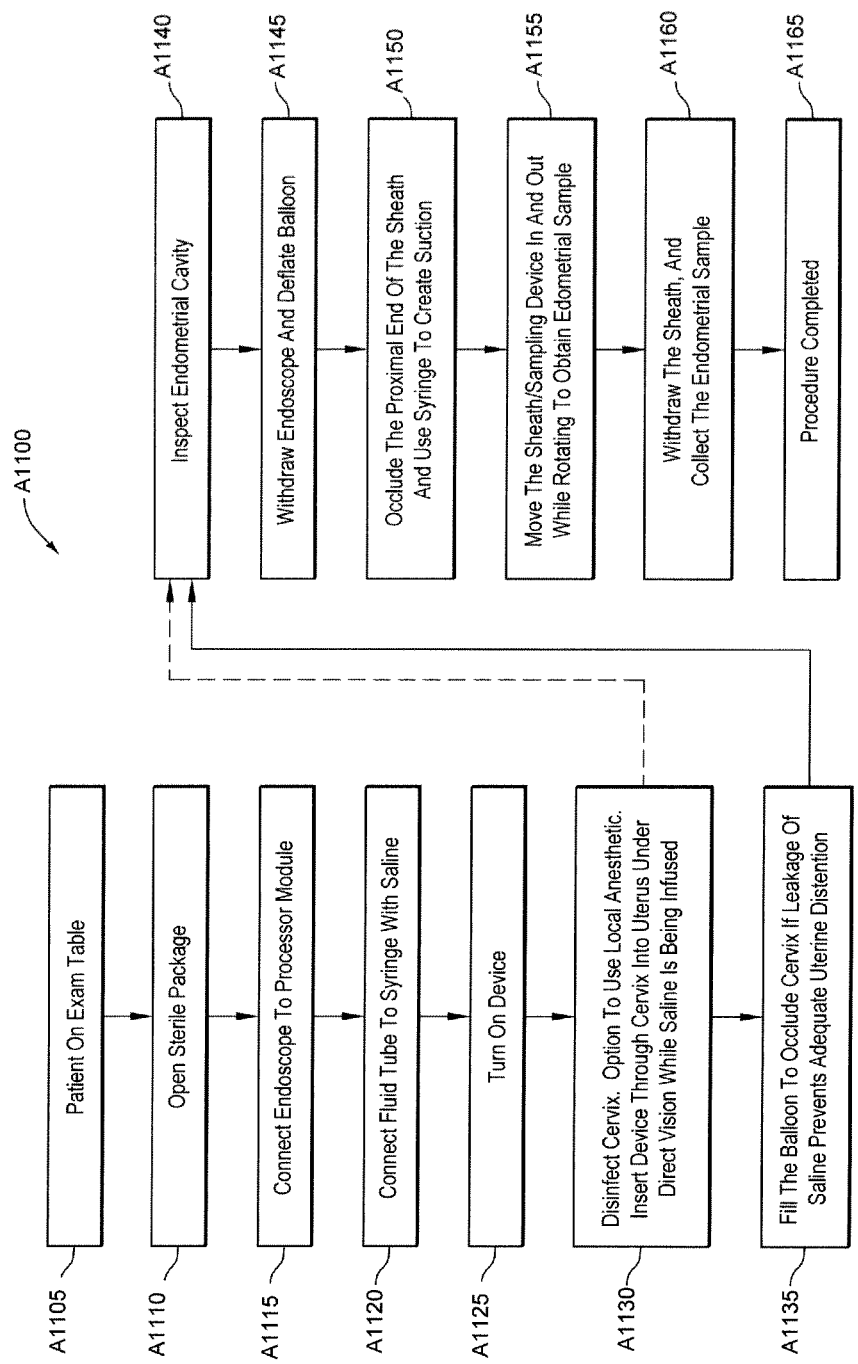
Fig. A 11

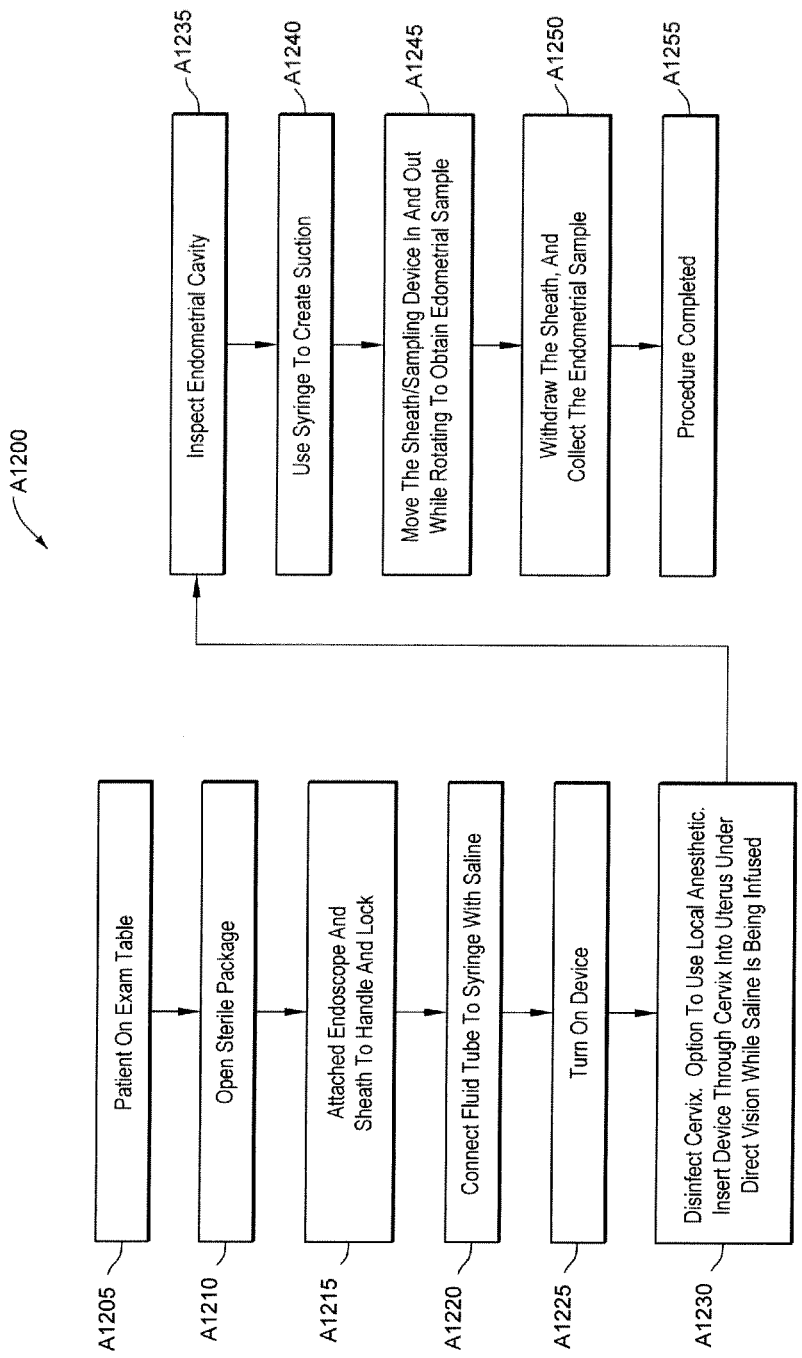
Fig. A 12

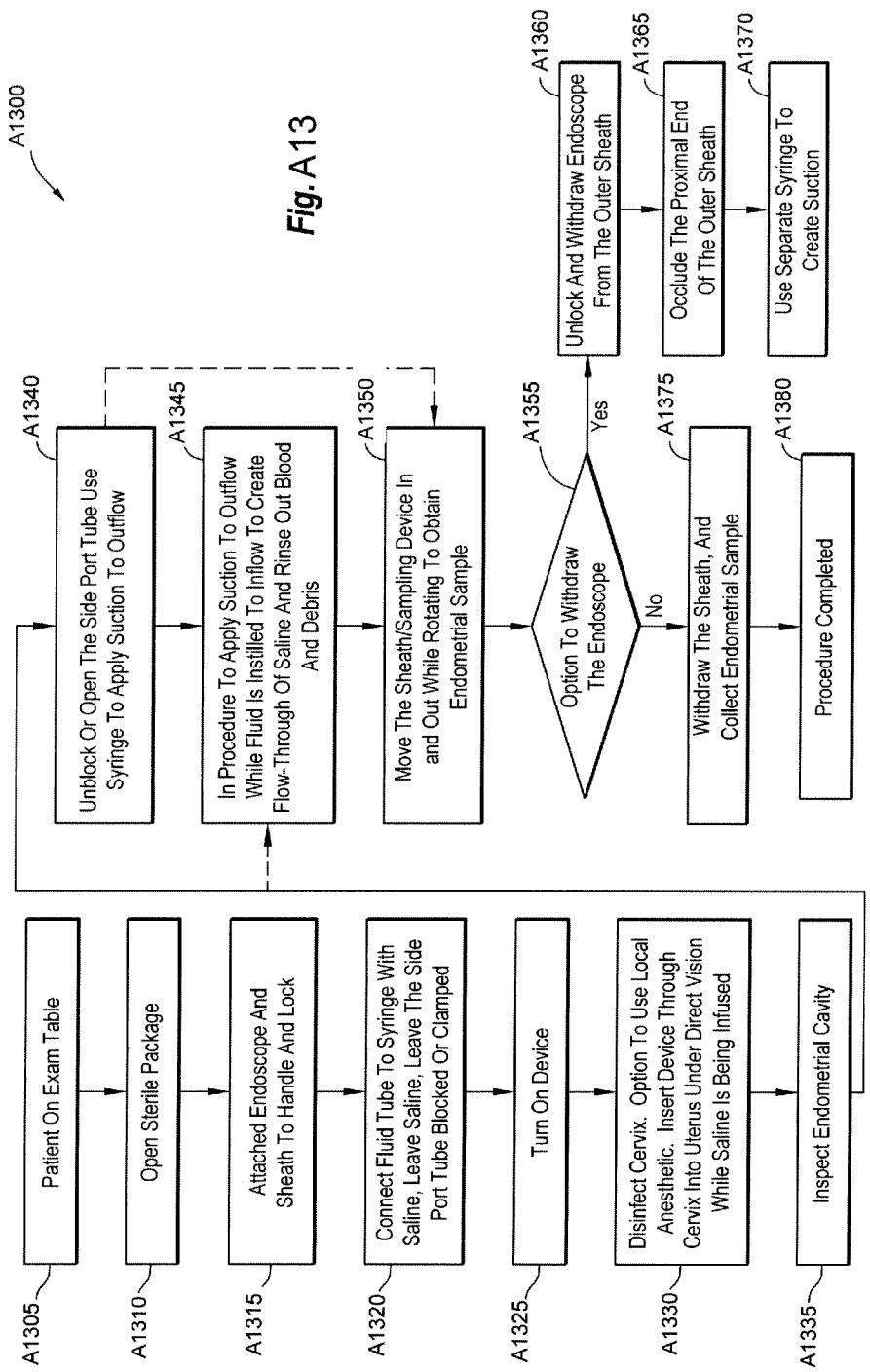

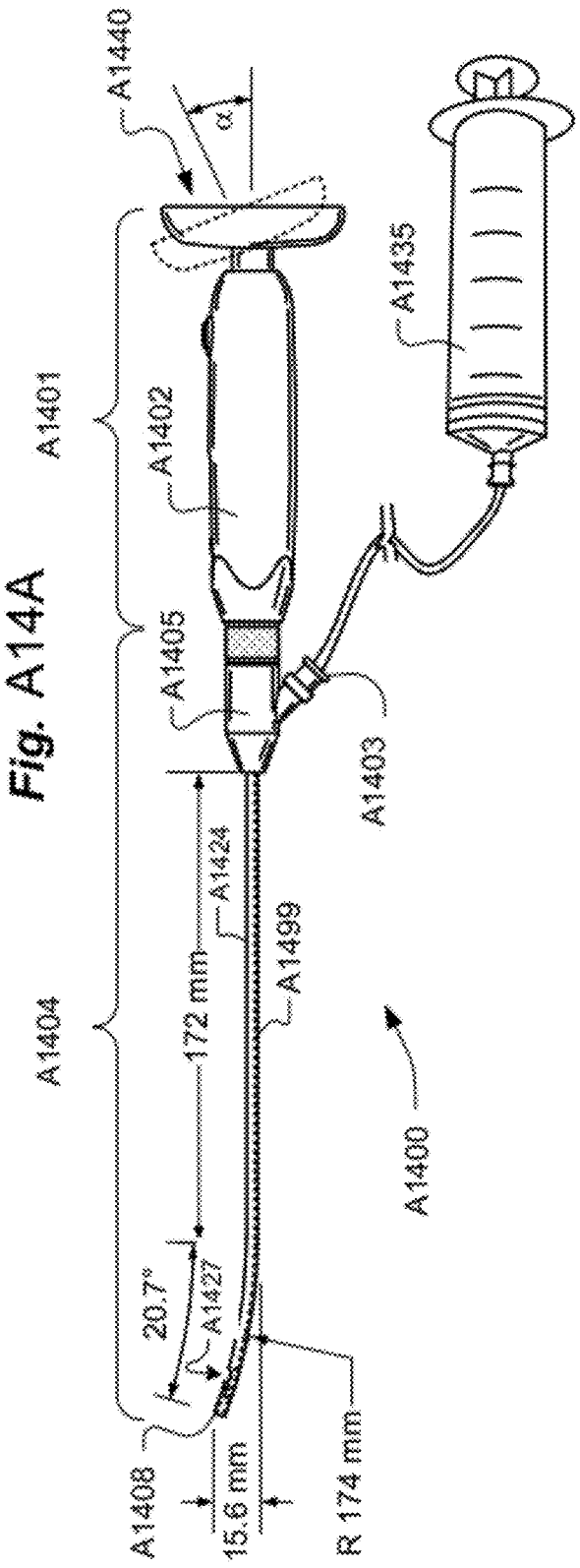
Fig. A14A
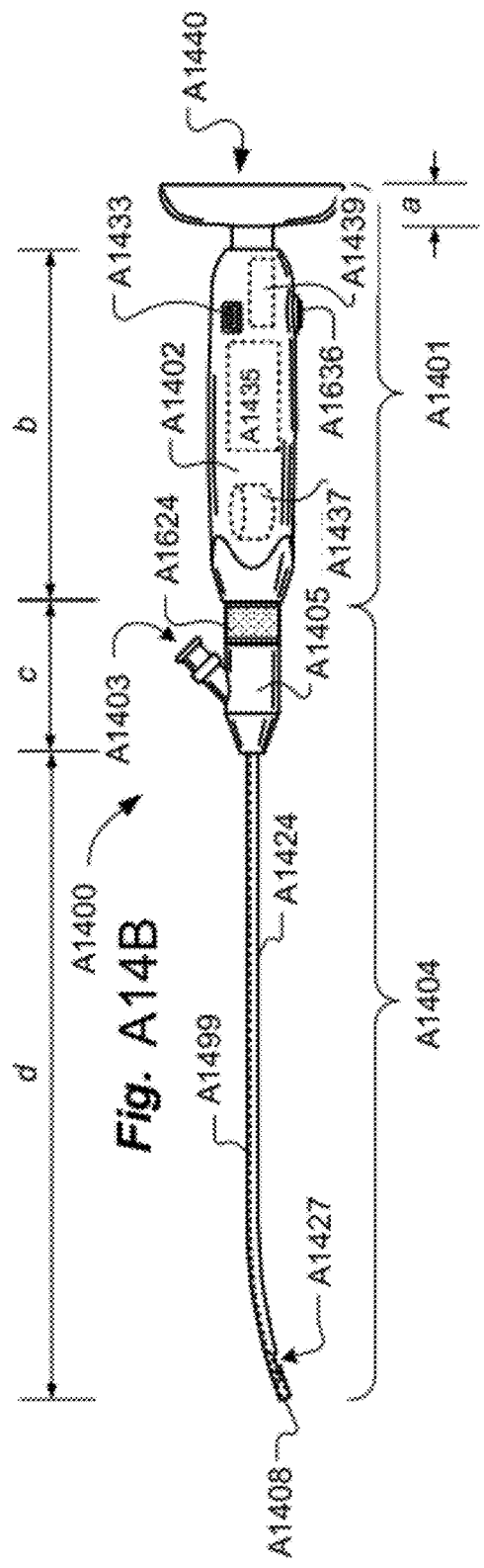
Fig. A14B

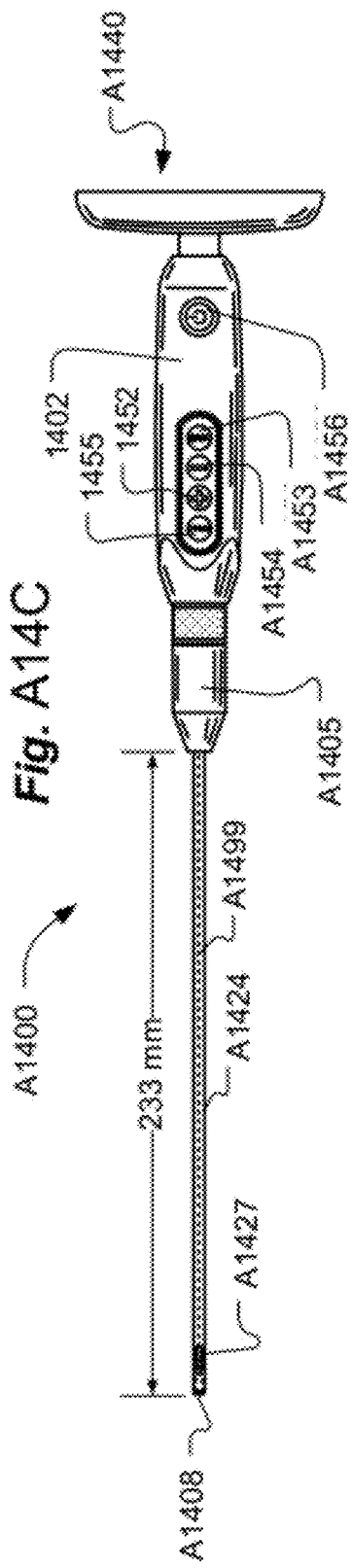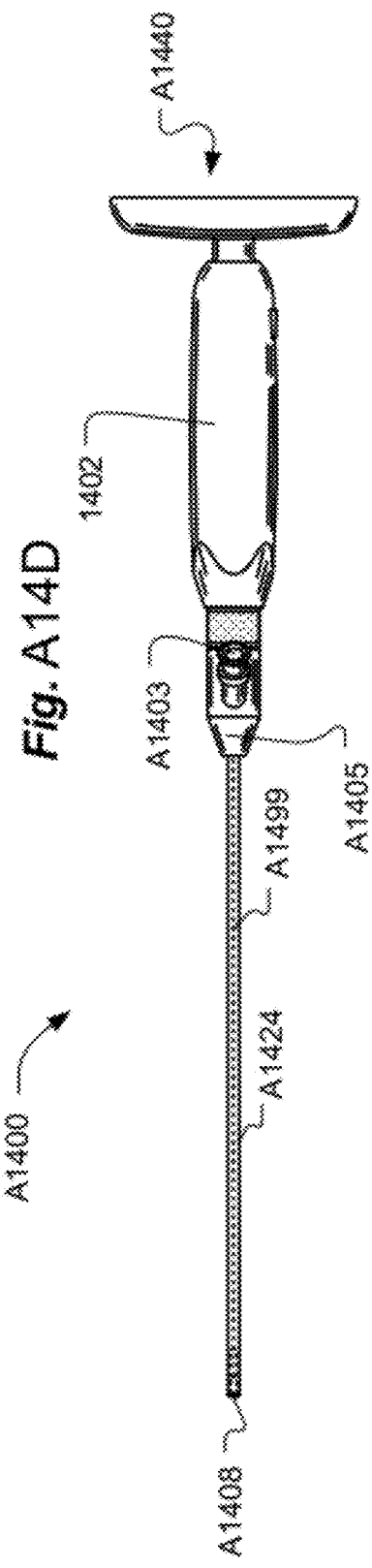

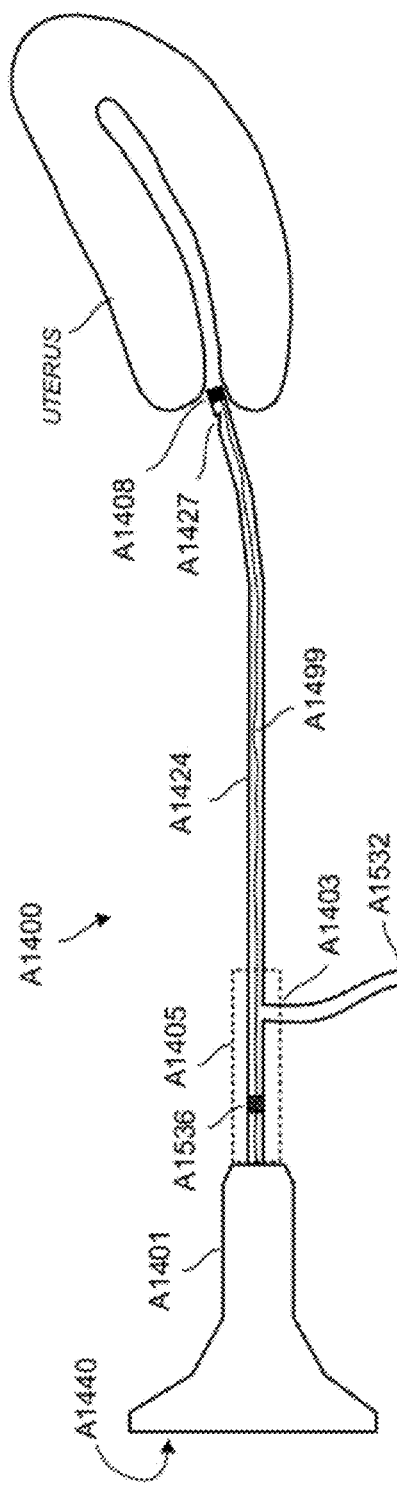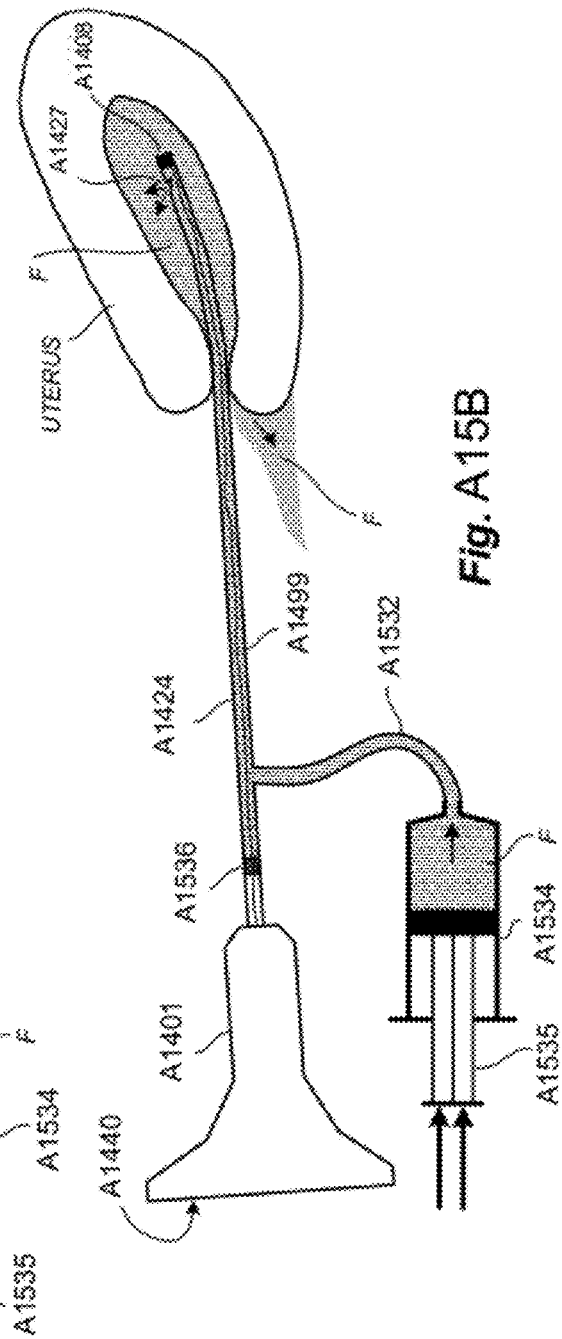
Fig. A15A
Fig. A15B

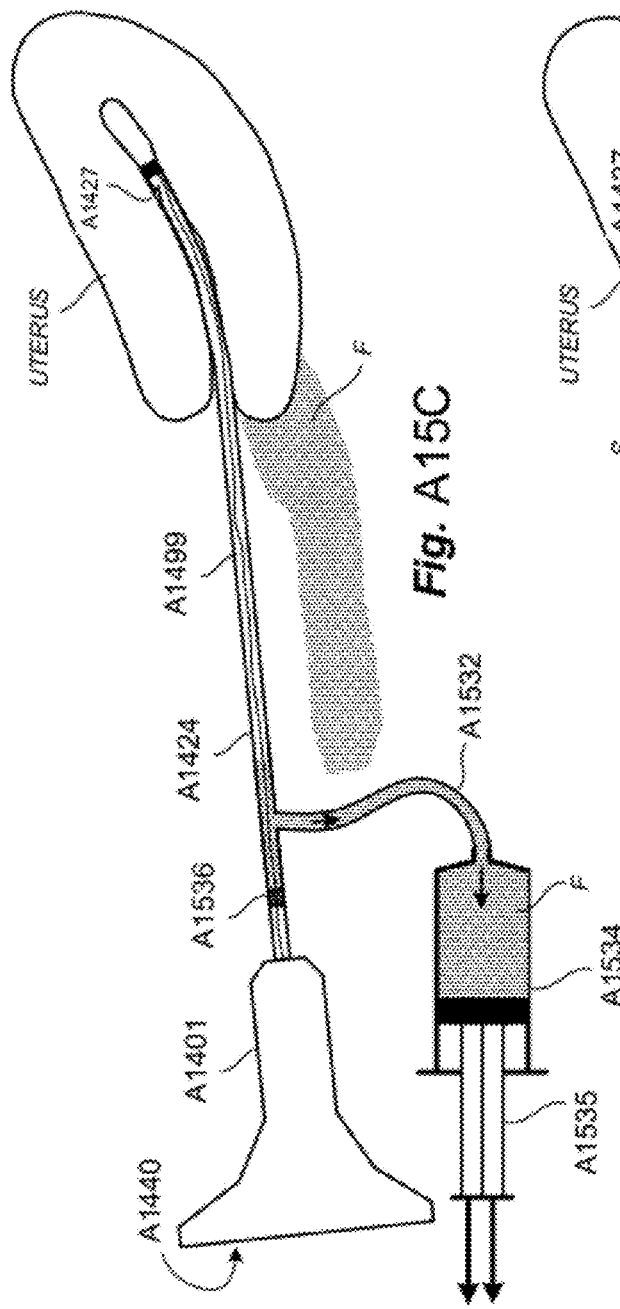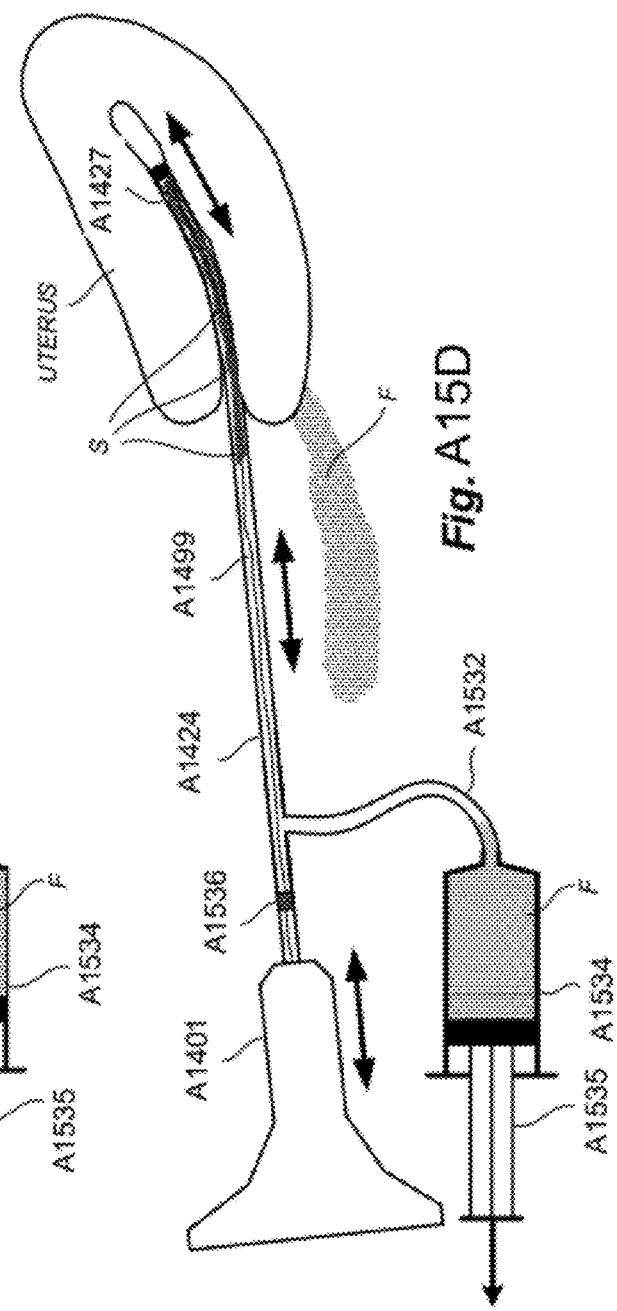

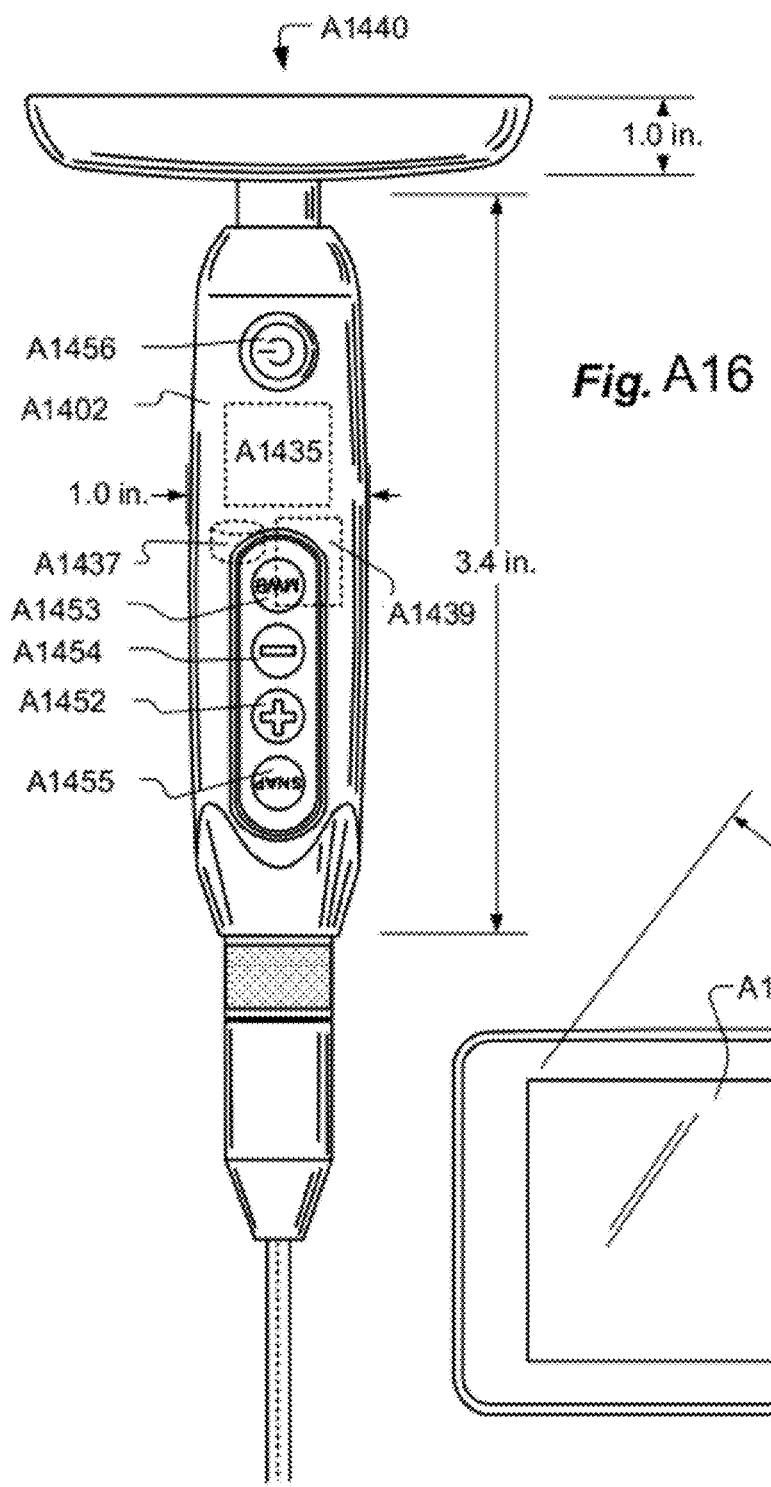
*Fig.* A16
*Fig.* A17

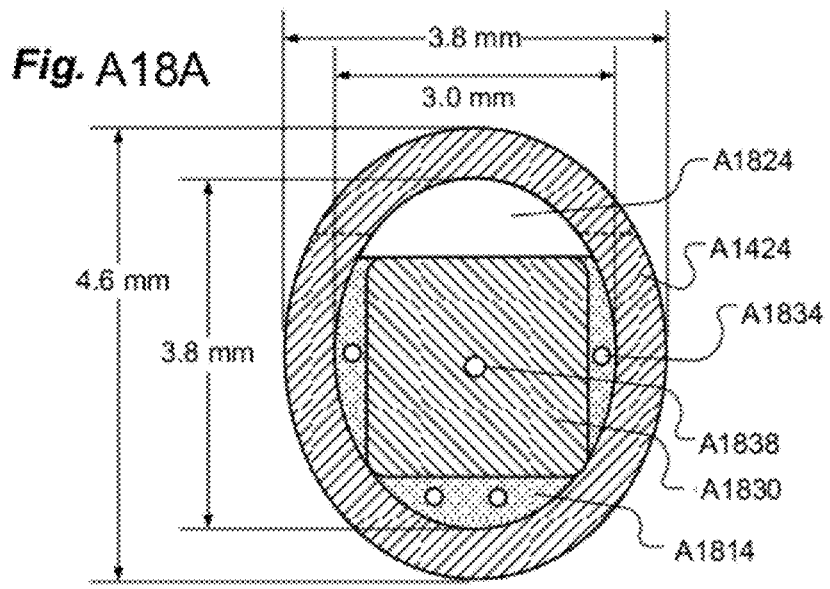
Fig. A18A
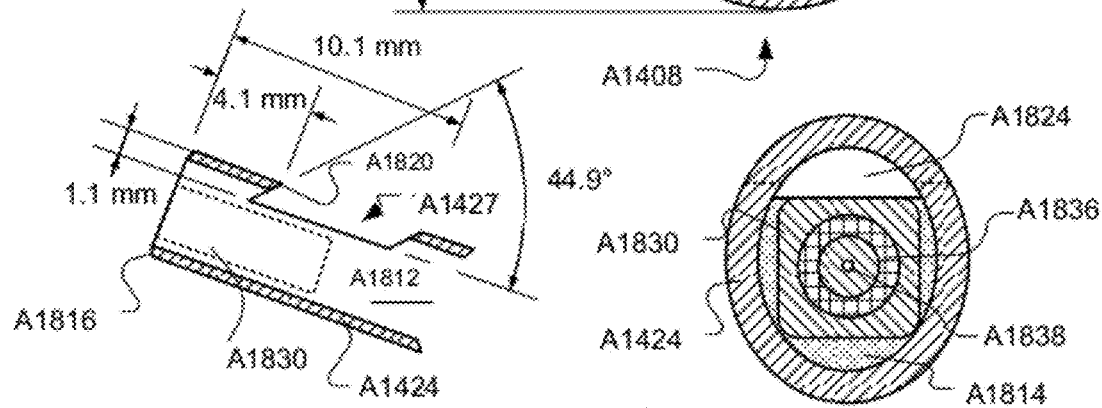
Fig. A18B
Fig. A18D
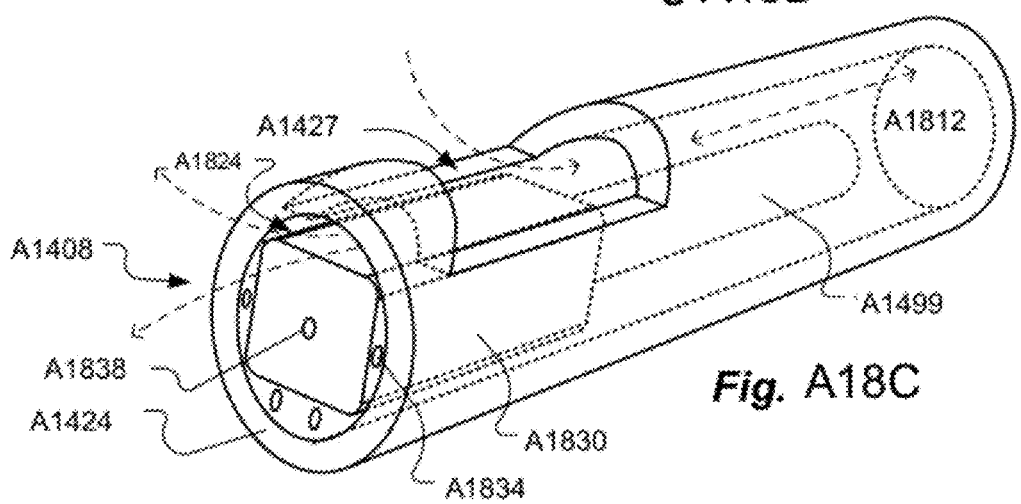
Fig. A18C

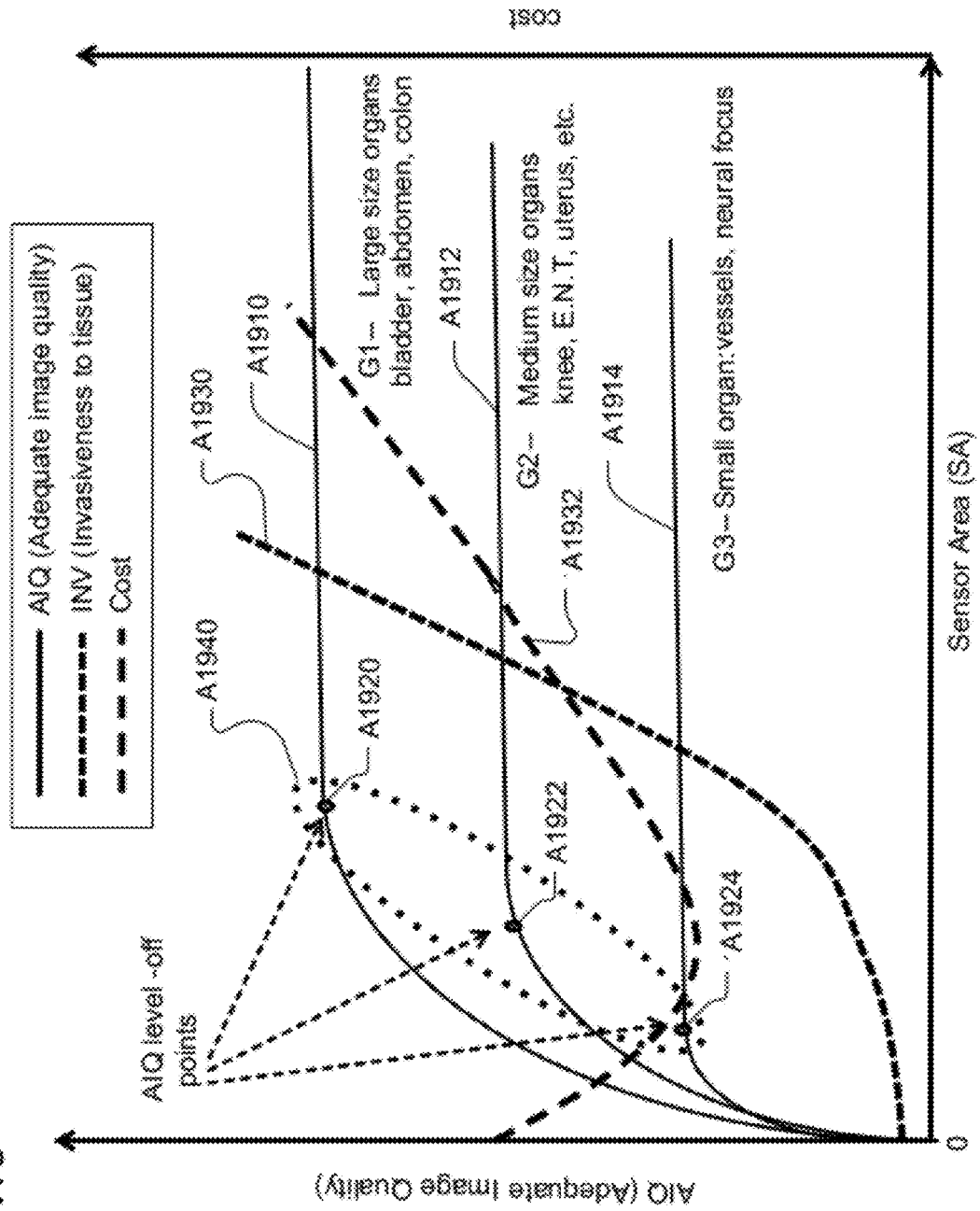
Fig. A19

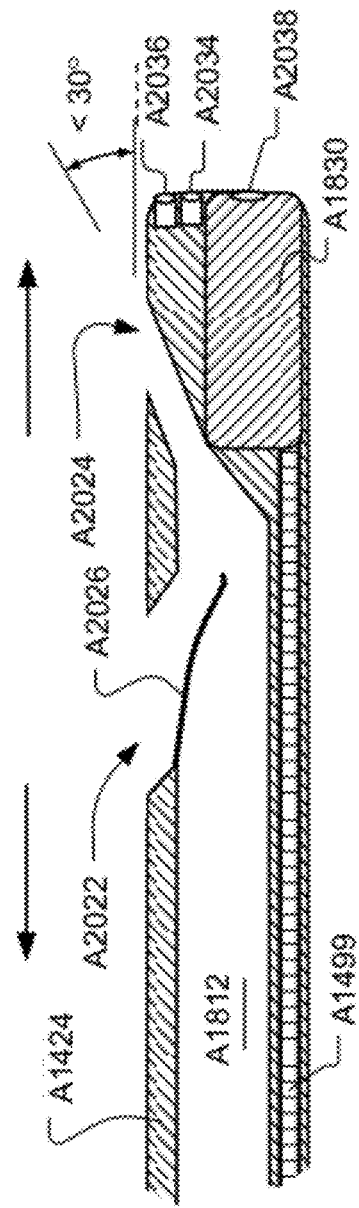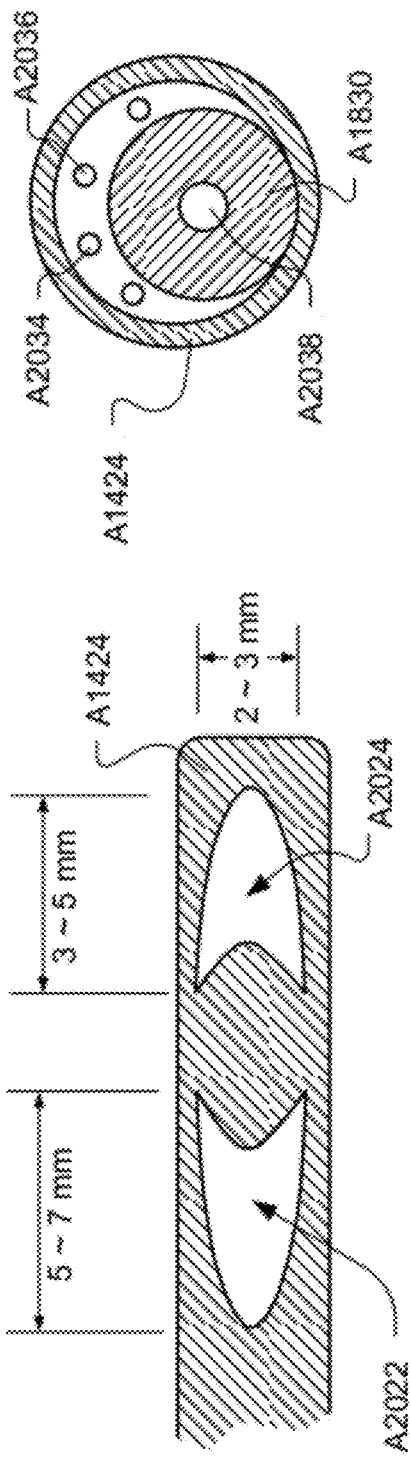

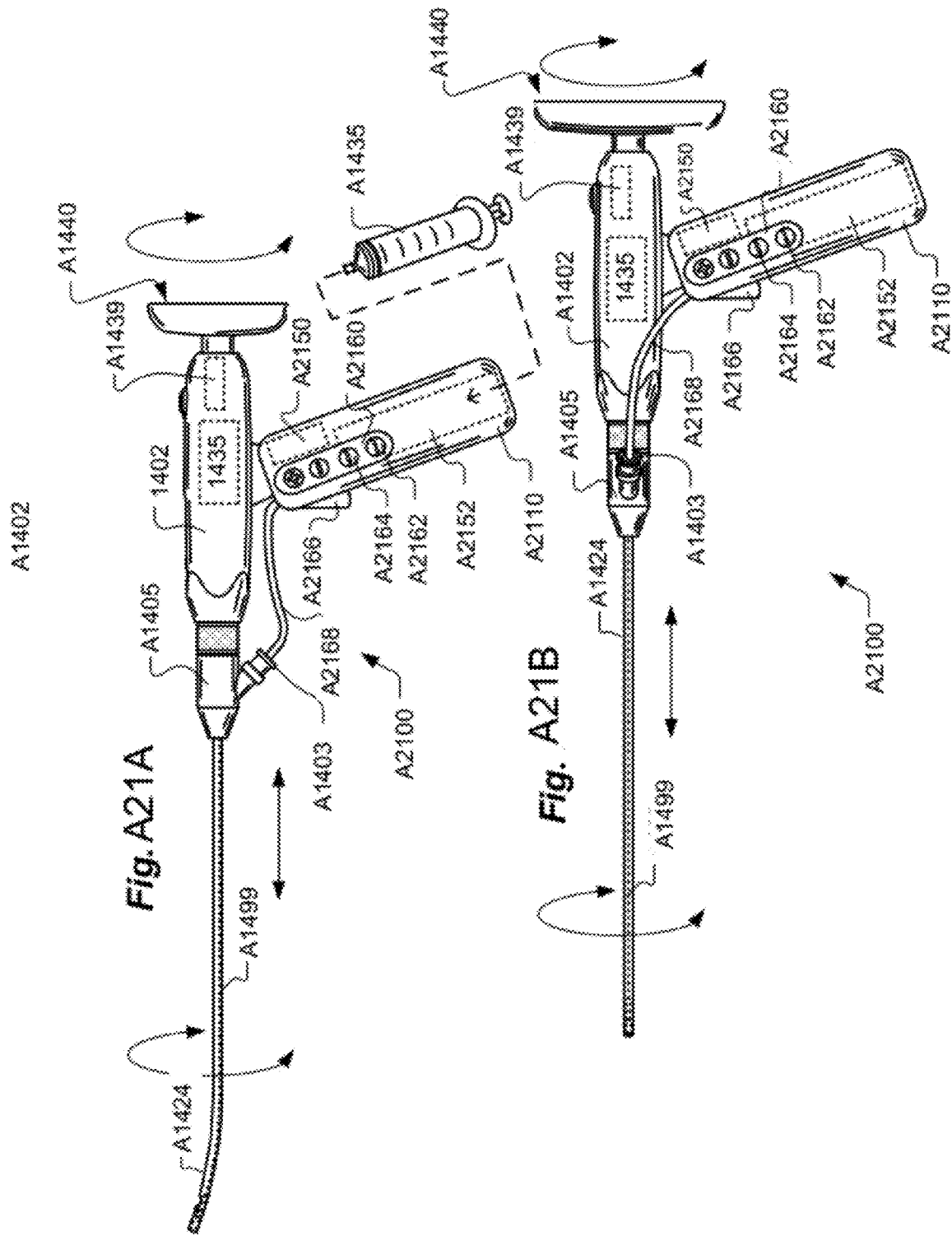

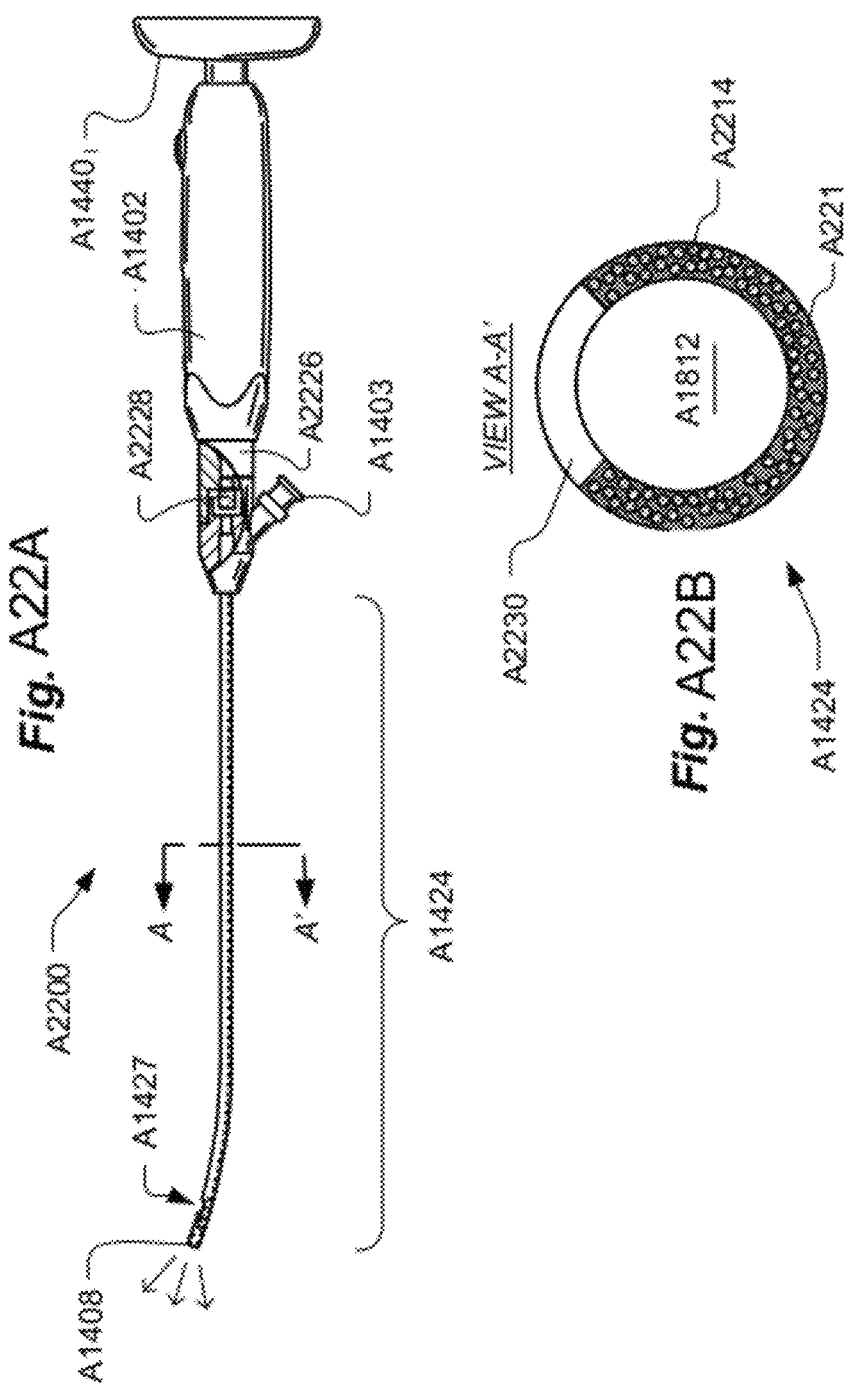

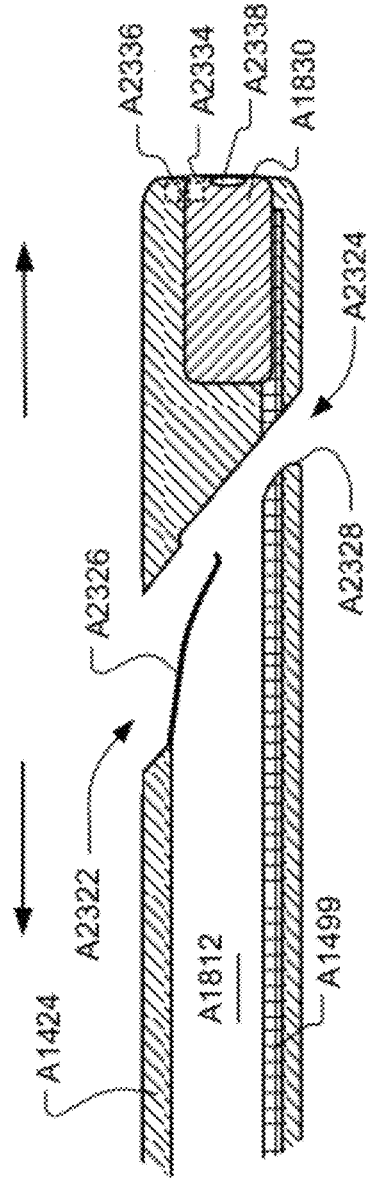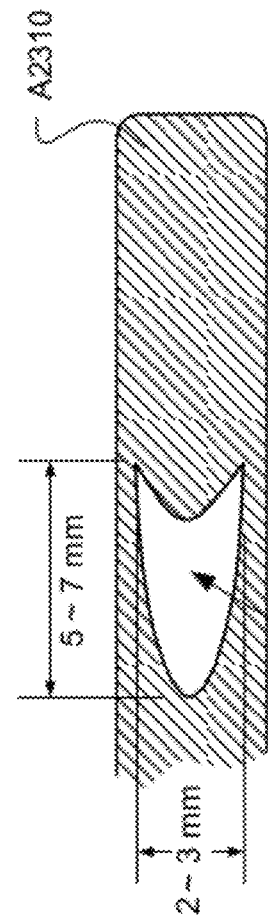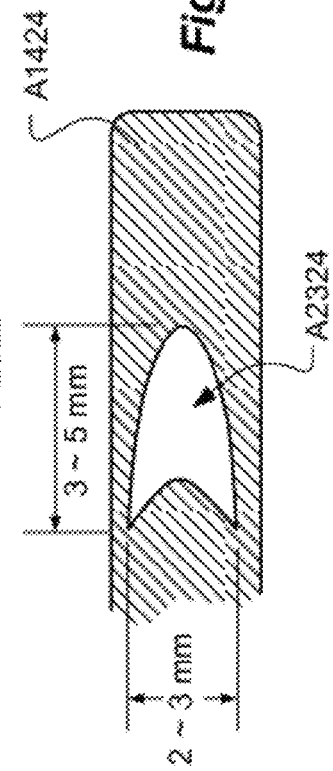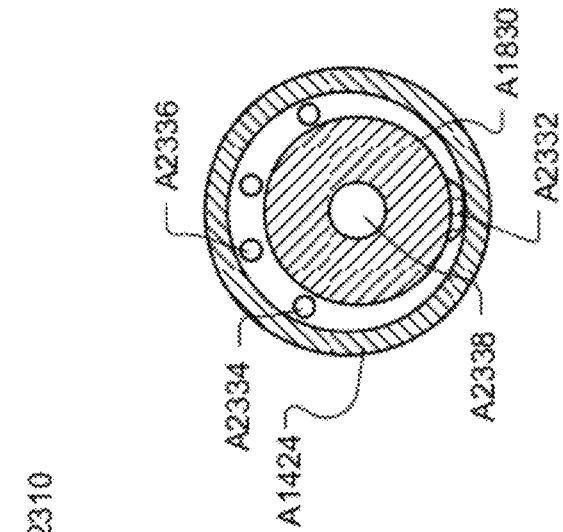

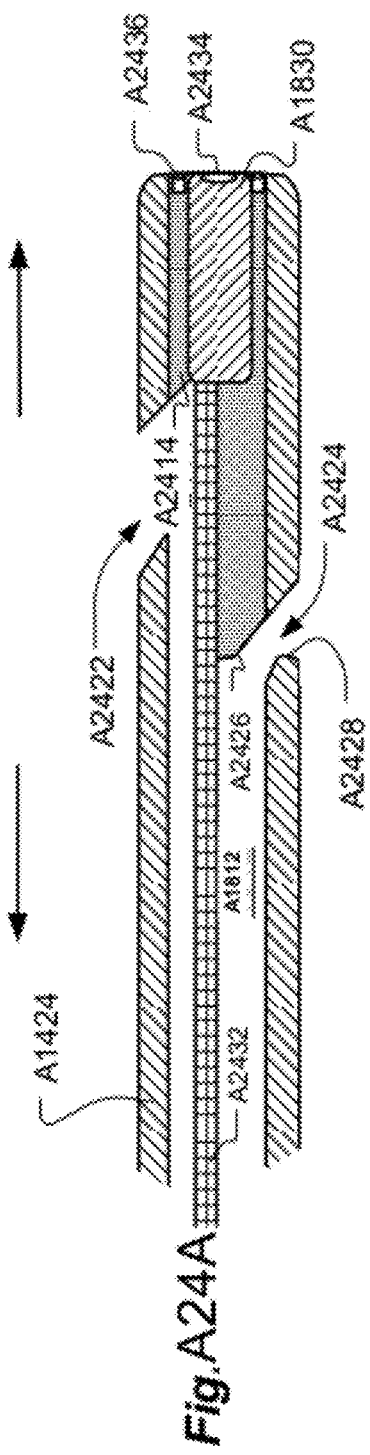
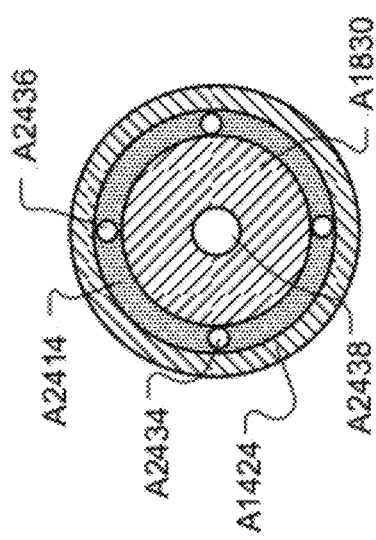

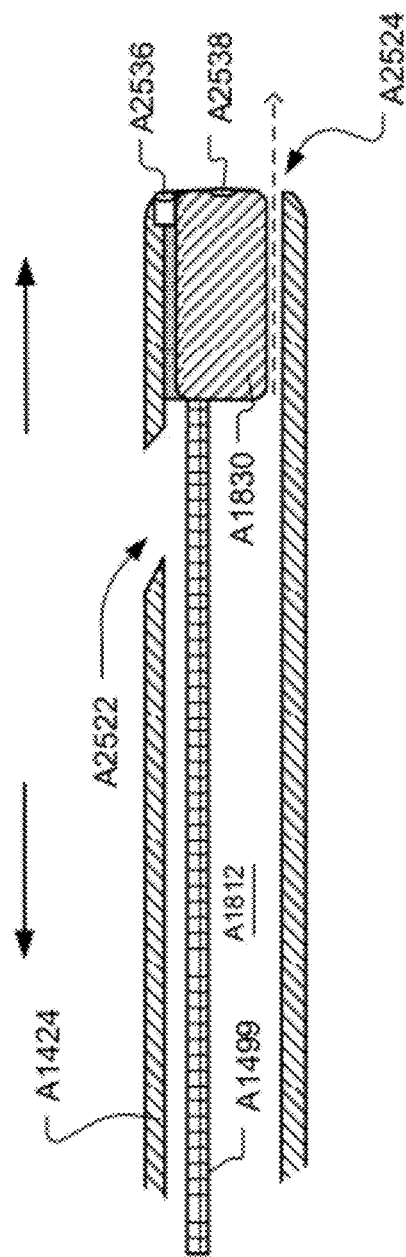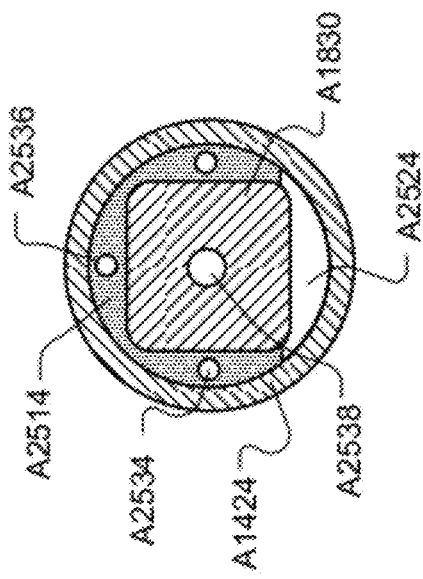

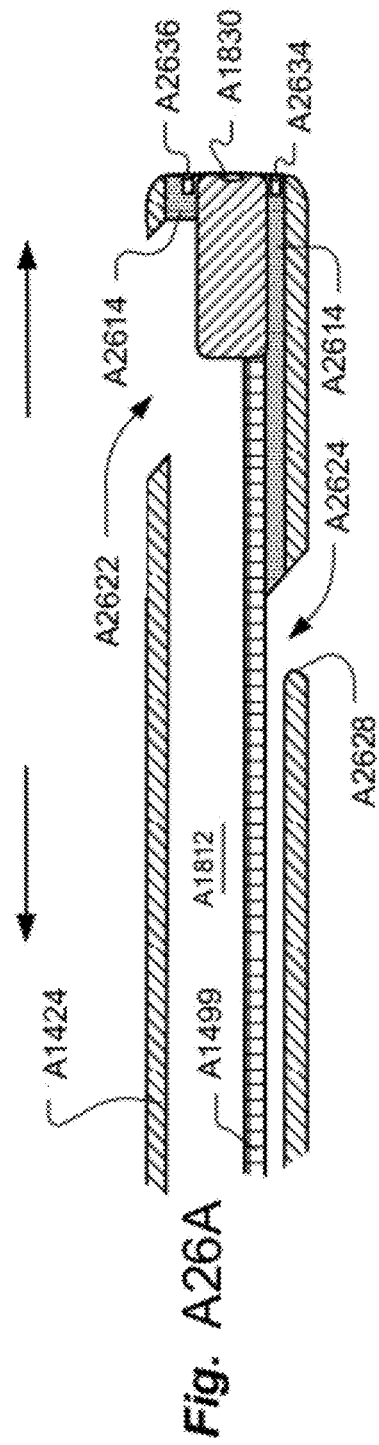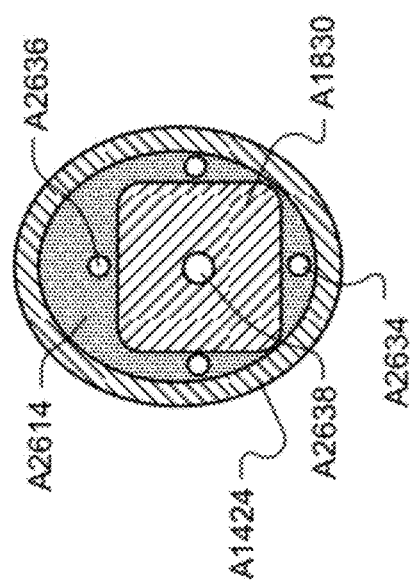
Fig. A26A
Fig. A26B

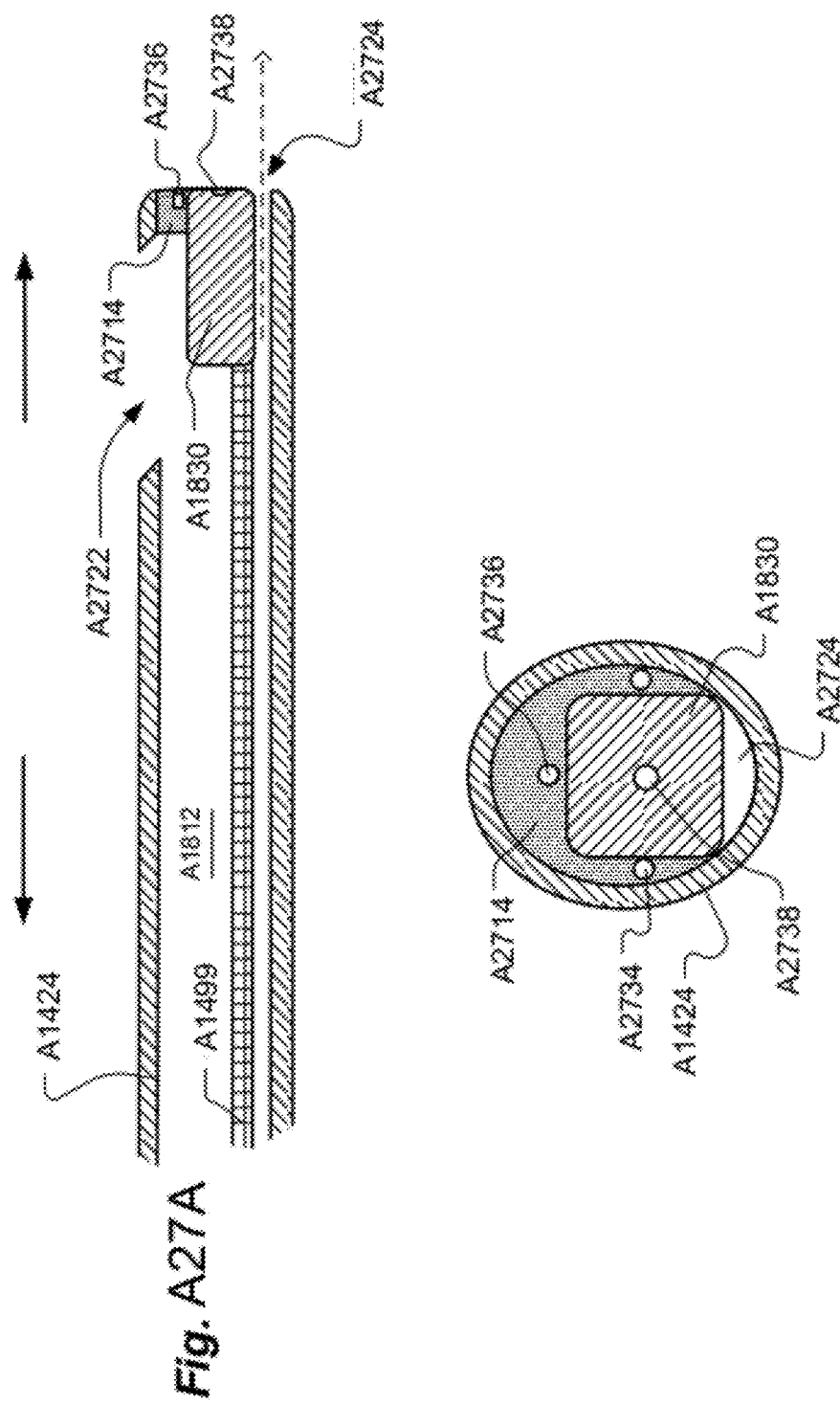

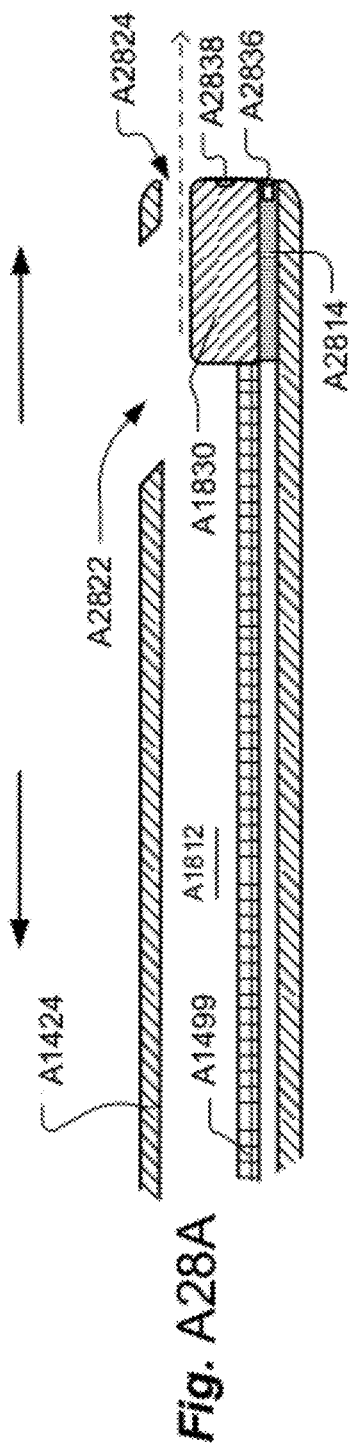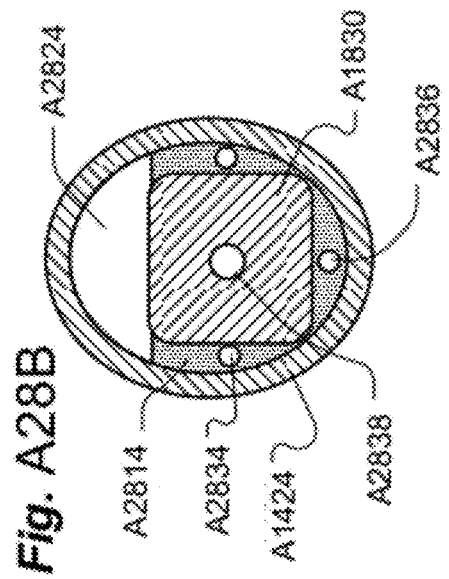

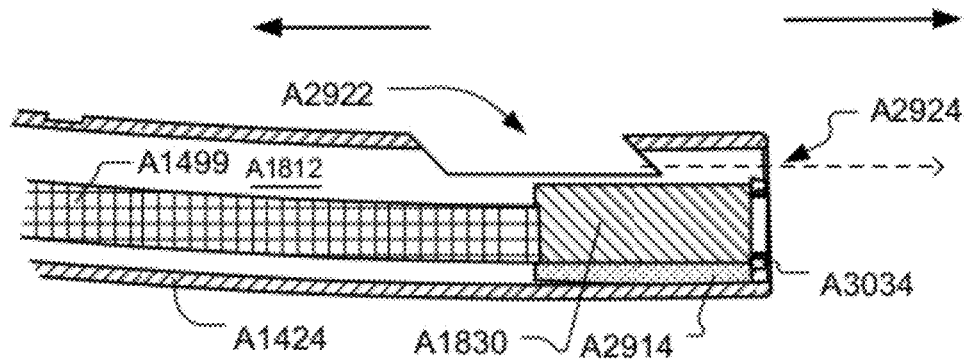
Fig. 29A
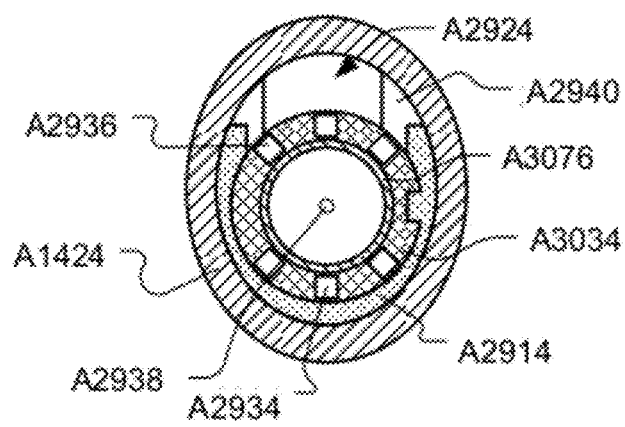
Fig. A29B

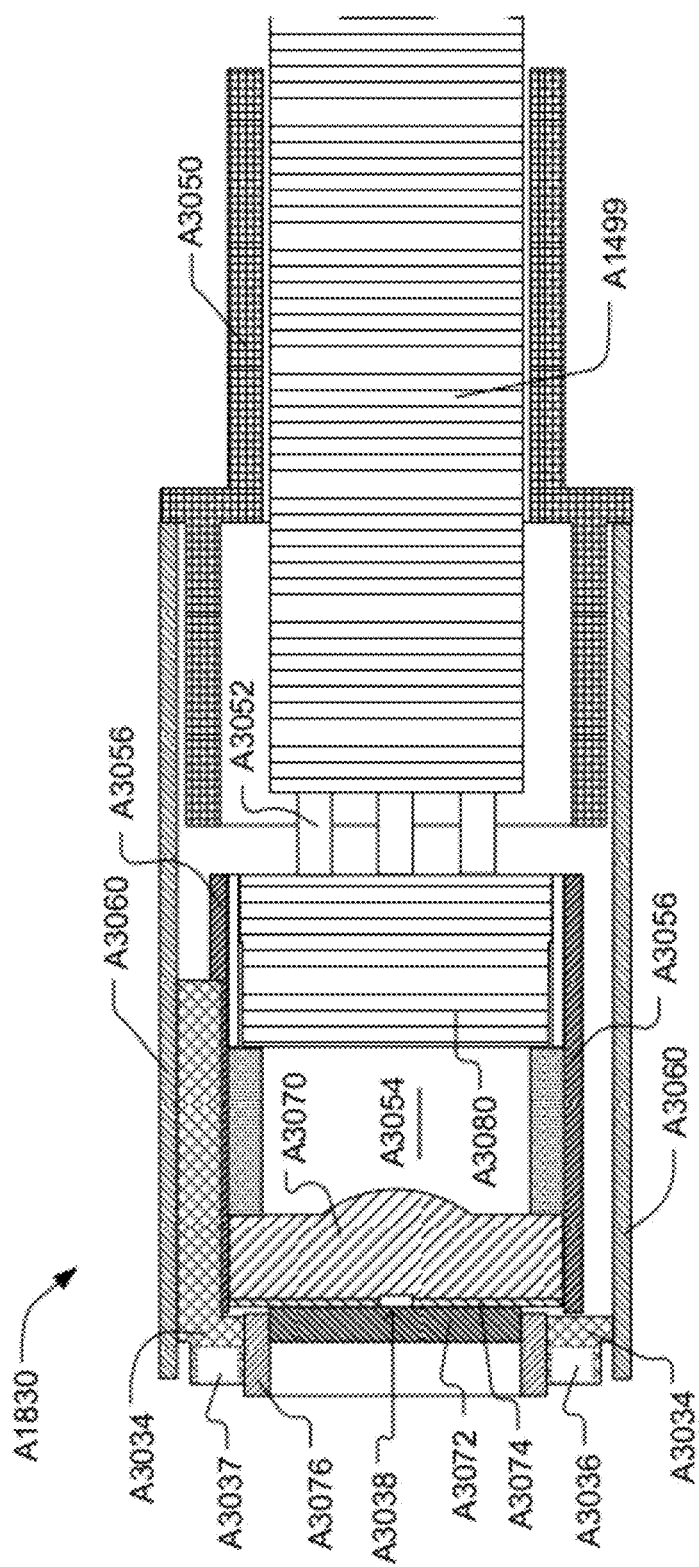
Fig. A30

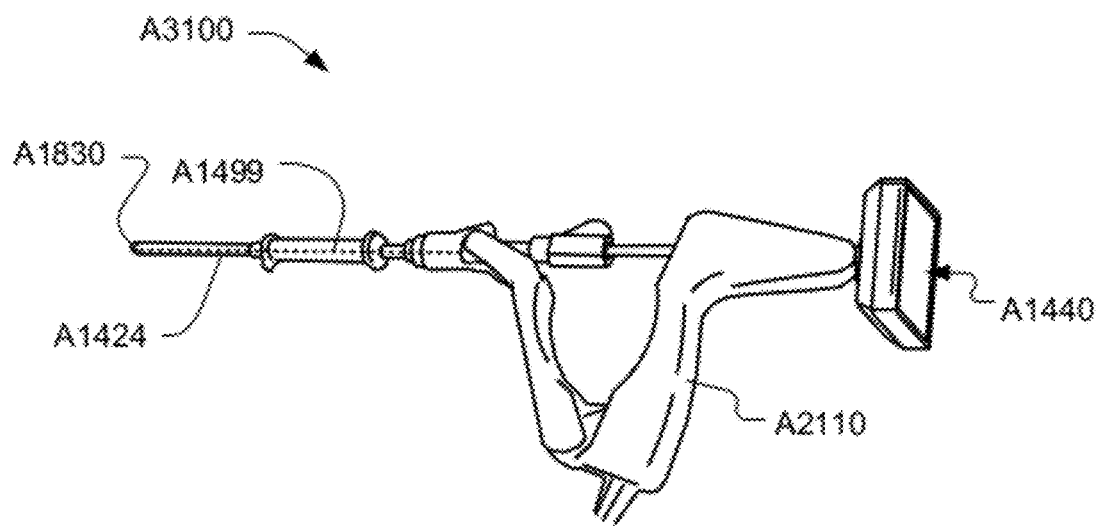
Fig. A31
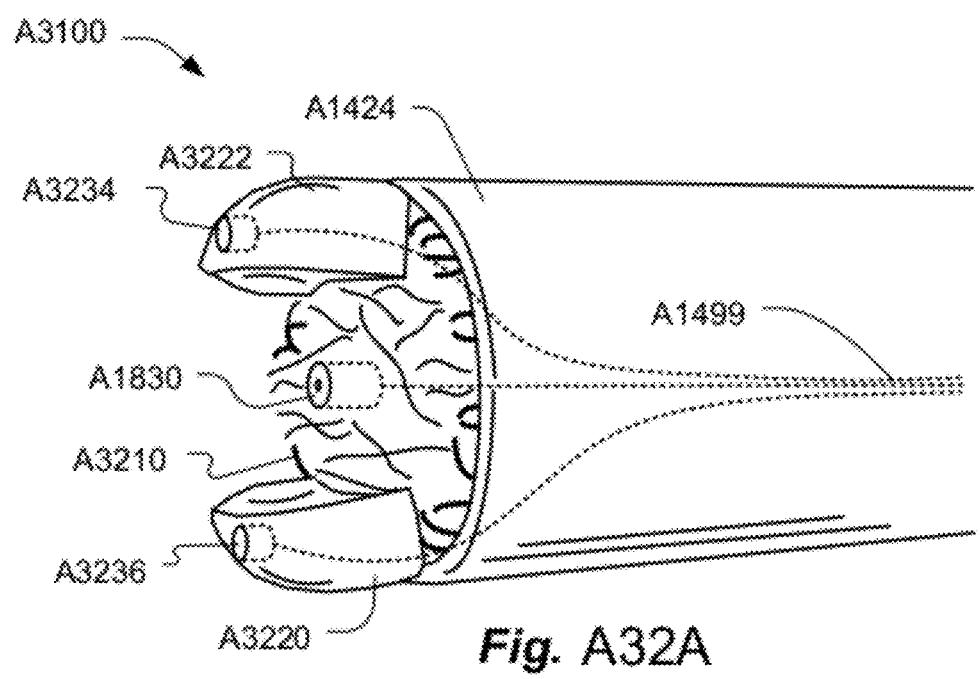
Fig. A32A

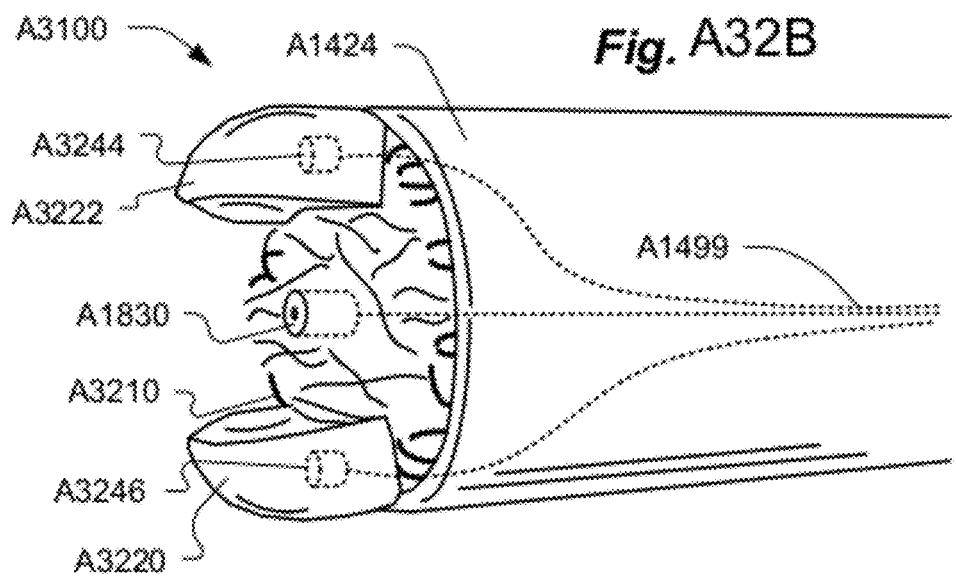
Fig. A32B
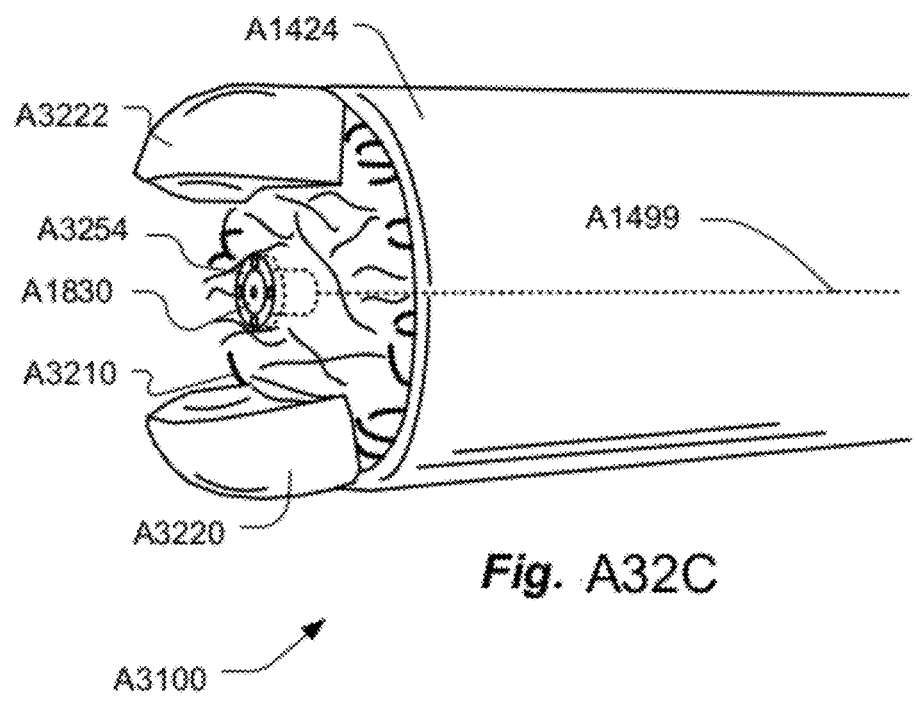
Fig. A32C

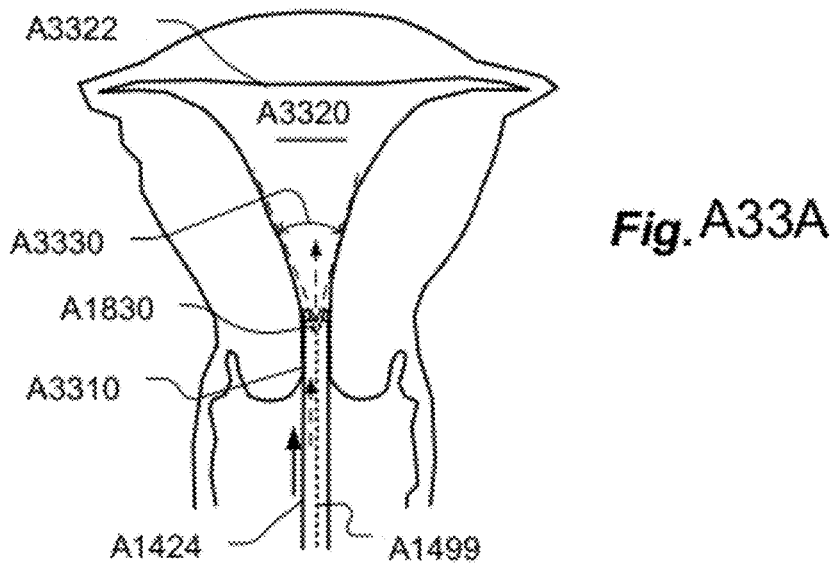
Fig. A33A
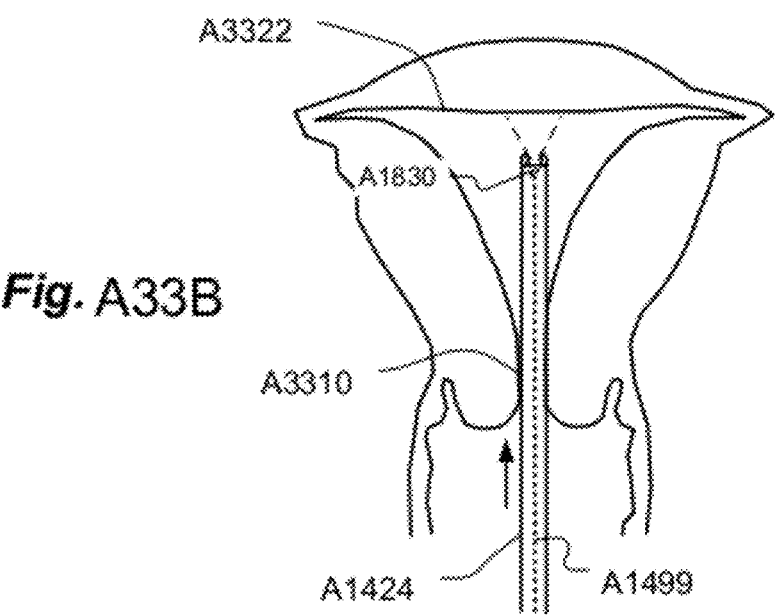
Fig. A33B

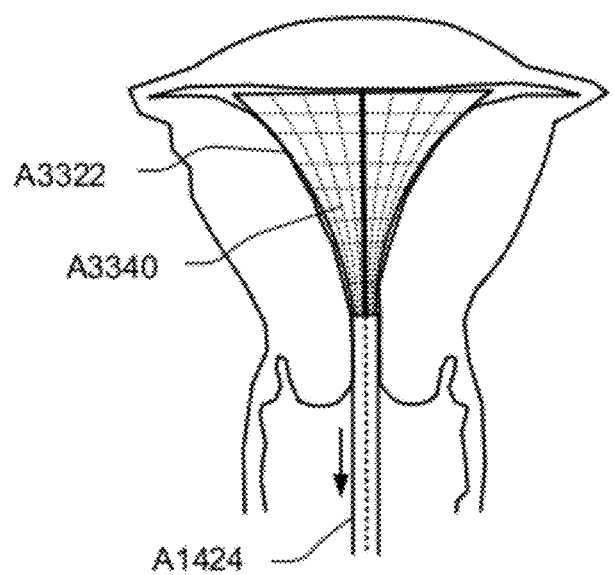
Fig. A33C

METHOD AND APPARATUS FOR HYSTEROSCOPY AND ENDOMETRIAL BIOPSY

CROSS-REFERENCE TO RELATED APPLICATIONS

This patent application is a continuation-in-part of the following international and U.S. non-provisional patent applications and claims the benefit of and incorporates by reference each of the following international applications, the U.S. non-provisional U.S. application the benefit of which the international applications claim, and the U.S. provisional patent applications the benefit of which the international and U.S. non-provisional applications claim:

International Patent Appl. No. PCT/US12/34698 filed Apr. 23, 2012;
International Patent Appl. No. PCT/US11/051,982 filed Sep. 16, 2011;
U.S. Ser. No. 12/911,297, filed Oct. 25, 2010;
U.S. Prov. Ser. No. 61/623,376 filed Apr. 12, 2012;
U.S. Prov. Ser. No. 61/611,182 filed Mar. 15, 2012;
U.S. Prov. Ser. No. 61/600,593 filed Feb. 18, 2012;
U.S. Prov. Ser. No. 61/599,981 filed Feb. 17, 2012;
U.S. Prov. Ser. No. 61/570,816 filed Dec. 14, 2011;
U.S. Prov. Ser. No. 61/556,167 filed Nov. 4, 2011;
U.S. Prov. Ser. No. 61/555,470 filed Nov. 3, 2011;
U.S. Prov. Ser. No. 61/550,391 filed Oct. 22, 2011;
U.S. Prov. Ser. No. 61/544,280 filed Oct. 7, 2011;
U.S. Prov. Ser. No. 61/539,736 filed Sep. 27, 2011;
U.S. Prov. Ser. No. 61/515,092 filed Aug. 4, 2011;
U.S. Prov. Ser. No. 61/506,074 filed Jul. 9, 2011;
U.S. Prov. Ser. No. 61/494,400 filed Jun. 7, 2011;
U.S. Prov. Ser. No. 61/490,029 filed May 25, 2011;
U.S. Prov. Ser. No. 61/485,601 filed May 12, 2011;
U.S. Prov. Ser. No. 61/482,309 filed May 4, 2011;
U.S. Prov. Ser. No. 61/482,200 filed May 3, 2011;
U.S. Prov. Ser. No. 61/476,754 filed Apr. 18, 2011;
U.S. Prov. Ser. No. 61/453,533 filed Mar. 16, 2011;
U.S. Prov. Ser. No. 61/450,115 filed Mar. 7, 2011;
U.S. Prov. Ser. No. 61/444,098 filed Feb. 17, 2011;
U.S. Prov. Ser. No. 61/437,687 filed Jan. 30, 2011;
U.S. Prov. Ser. No. 61/431,316 filed Jan. 10, 2011;
U.S. Prov. Ser. No. 61/429,093 filed Dec. 31, 2010;
U.S. Prov. Ser. No. 61/418,248 filed Nov. 30, 2010;
U.S. Prov. Ser. No. 61/415,771 filed Nov. 19, 2010; and
U.S. Prov. Ser. No. 61/324,961 filed Apr. 16, 2010.

The above-referenced international and U.S. non-provisional and provisional patent applications are collectively referenced herein as "the commonly assigned incorporated applications."

FIELD

The present invention generally relates to a medical device for use in hysteroscopic examinations and sampling of the uterus. More particularly, some embodiments relate to a medical device having integrated visualization and endometrial sampling components.

BACKGROUND

Office-based endometrial biopsy is a standard diagnostic procedure used by gynecologists. While efficacious in detection of cancer, endometrial biopsy frequently will not detect endometrial polyps, submucous myomas, and other endometrial pathology. Hysteroscopy, or direct vision of the inside of the uterus (referred to herein as the "uterine cavity" and/or "endometrial cavity"), has been shown to greatly improve diagnostic accuracy. Few gynecologists do office hysteroscopy, however, because of the complexity and expense of the equipment and supplies required. While it is possible to take tiny biopsies through some hysteroscopes that have operating channels, the surgeon usually needs to remove the hysteroscope and then do an endometrial biopsy with a different instrument. The repeated insertion and removal of multiple instruments into the patient's uterine cavity can be uncomfortable for the patient and/or may prolong the time required to complete the hysteroscopy and endometrial sampling procedures compared to performing both procedures without the repeated insertion and removal of different instruments. And, such use of multiple instruments for the same inspection/biopsy procedure requires the expense and inconvenience of buying, stocking and sterilizing such instruments.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

According to some embodiments, an integrated endoscopic apparatus for examining uterine tissues is described. The apparatus includes: an elongate member having a proximal end, a distal end, and being dimensioned so as to facilitate insertion of the distal end through a patient's cervix and into the uterus; a light delivery system adapted to illuminate the uterine tissues being examined; a side-facing sampling opening in the elongate member located and dimensioned so as to facilitate in collection of endometrial tissues; an electronic imaging module positioned on the distal end of the elongate member; and a distal-facing fluid opening positioned on the distal end of the elongate member so as to improve visual inspection using the electronic imaging module by allowing fluid to flow in a distal direction near the lens thereby reducing debris close to the imaging module. According to some embodiments the elongate member includes separated fluid paths for the side-facing opening and the distal-facing opening and/or internal features to enhance fluid flow from the elongate member through the distal-facing fluid opening. According to some embodiments, the electronic imaging module includes a solid-state CMOS sensor, as well as integrated video processing circuitry substantially co-planar with the sensor, to output standard video signals. According to some embodiments, the apparatus includes a handle and an integrated electronic display monitor.

According to some embodiments, an integrated endoscopic apparatus for examining uterine tissues is described that includes: an elongate member having a proximal end, a distal end, and being dimensioned so as to facilitate insertion of the distal end through a patient's cervix and into the uterus; an LED-based light delivery system positioned near the distal end and adapted so as to emit light from at least two points greater than 1 mm apart thereby illuminating uterine tissues being examined; a side-facing sampling opening in the elongate member located and dimensioned so as to facilitate in collection of endometrial tissues; an electronic imaging module positioned on the distal end of the elongate member; and a fluid opening positioned on the distal end of the elongate member so as to improve visual inspection using the electronic imaging module by allowing fluid to flow in a distal direction near the lens thereby reducing debris close to the imaging module. According to some embodiments, the electronic imaging module includes a centrally positioned aperture through which light enters the imaging module, and the light delivery system includes two LEDs positioned on the distal end at opposite sides of the aperture from one another. According to some embodiments, the light delivery system includes a ring-shaped LED module positioned so as to surround the aperture.

According to some embodiments, an integrated endoscopic apparatus for examining uterine tissues is described that includes: an elongate member having a proximal end, a distal end, and being dimensioned so as to facilitate insertion of the distal end through a patient's cervix and into the uterus, wherein the distal end of the elongate member comprises an at least partially hollow shaft member, and a distal tip member wherein the shaft and tip members are separately formed so as to be mated to one another during assembly; a light delivery system adapted to illuminate the uterine tissues being examined; a side-facing sampling opening in the elongate member located and dimensioned so as to facilitate in collection of endometrial tissues; and an electronic imaging module positioned on the distal end of the elongate member. According to some embodiments, a distal-facing fluid opening is positioned on the distal end of the elongate member so as to improve visual inspection using the electronic imaging module by allowing fluid to flow in a distal direction near the lens thereby reducing debris close to the imaging module. According to some embodiments, the shaft and tip members are separately formed for improved assembly yield. The distal tip uses acrylic and the elongate member uses nylon.

According to some embodiments, a method of manufacturing an integrated endoscopic apparatus for examining uterine tissues is described which includes: forming a distal end tip body that is dimensioned to house a light delivery system adapted to illuminate the uterine tissues being examined, and an electronic imaging module positioned on the distal end of the elongate member, the distal end tip body also being formed so as to provide a side-facing sampling opening in the tip body located and dimensioned so as to facilitate in collection of endometrial tissues; forming an elongate shaft member; and securely attaching the distal tip body to the elongate shaft member thereby forming an elongate member of an integrated endoscope dimensioned so as to facilitate insertion of the distal end through a patient's cervix and into the uterus.

According to some embodiments a user-friendly integrated endoscopic apparatus for examining uterine tissues is described that includes an elongate member having a proximal end, a distal end, and being dimensioned so as to facilitate insertion of the distal end through a patient's cervix and into the uterus; a light delivery system adapted to illuminate the uterine tissues being examined; a side-facing sampling opening in the elongate member located and dimensioned so as to facilitate in collection of endometrial tissues; an electronic imaging module positioned on the distal end of the elongate member; a handle having a low overall off-axis profile so as to facilitate easy rotation and tilting in use, the handle including a plurality of buttons to control a plurality of features of the apparatus; and an integrated touch-sensitive electronic display monitor being in electrical communication with the electronic imaging module. According to some embodiments a brightness control button is included with which a user can make a selection from at least three different illumination levels from the light delivery system. According to some embodiments, the plurality of buttons includes a capture button with which a user can select either capturing a still image, or capturing video images, which are stored in a storage device within the apparatus. According to some embodiments a lighted battery status indicator is provided that indicates battery status information to a user using two or more colors. According to some embodiments, a plurality of display screens can be displayed on the integrated touch-sensitive display monitor including a basic menu screen from which a plurality of other screens can be accessed, and one of the plurality of buttons on the handle can be used by a user to jump directly to the basic menu screen.

According to some embodiments, a method for interacting with a user is described including displaying to a user a plurality of screens on a touch-sensitive electronic display monitor, the monitoring being integrated with an endoscopic apparatus. According to some embodiments, user input on the touch sensitive display is received indicating a selection by the user of a stored captured image file (e.g. a still or video image) that the user would like to view. In response to the received user selection, content from the selected stored image file is displayed on the touch sensitive display.

According to some embodiments, an integrated endoscopic apparatus for examining uterine tissues is described including: an elongate member having a proximal end, a distal end, the distal end including a distal face having a rounded edges so as to facilitate safe insertion of the distal end through a patient's cervix and into the uterus, wherein the edges are rounded to a radius of at least 0.25 millimeters; a light delivery system adapted to illuminate the uterine tissues being examined; an electronic imaging module positioned on the distal end of the elongate member; a handle; and an integrated electronic display monitor, the display monitor being in electrical communication with the electronic imaging module. According to some embodiments the edges of the distal face are rounded to a radius of at least 0.35 millimeters, or at least 0.5 millimeters. According to some embodiments the distal face is convex, so as to decrease collection of inadvertent tissue collection on the distal face which could impair visual examination using the imaging module.

Other features and other embodiments will become apparent from the description of drawings and detailed description of preferred embodiments below.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIG. 1 is a left side view of a device for combined hysteroscopy and endometrial biopsy according to some embodiments;

FIG. 2 is a top plan view of a device for combined hysteroscopy and endometrial biopsy according to some embodiments;

FIG. 3 is a right side view of a device for combined hysteroscopy and endometrial biopsy according to some embodiments;

FIG. 4 is a distal end view of a device for combined hysteroscopy and endometrial biopsy according to some embodiments;

FIG. 5 is a proximal end view of a device for combined hysteroscopy and endometrial biopsy according to some embodiments;

FIG. 8A is a right side view of a distal tip assembly of a device for combined hysteroscopy and endometrial biopsy according to some embodiments;

FIGS. 8B-8E are further views of the distal tip assembly of a device for combined hysteroscopy and endometrial biopsy according to some embodiments;

FIGS. 29 and 30 show further details of a distal tip for a device for combined hysteroscopy and endometrial biopsy, according to some embodiments;

FIGS. 31-33 show a single-use device for combined hysteroscopy and endometrial biopsy, according to various embodiments;

FIGS. 34-39 show a device combined hysteroscopy and endometrial biopsy having a detachable handle, which can be mated with a docking station, according to some embodiments;

FIGS. 36 and 37 are a perspective view and a side view, respectively, of the handle and display docked to a base station, according to some embodiments;

FIGS. 47-48 are side views showing details of the shapes of distal tips of a hysteroscopy device, according to some embodiments.

Figure 6:
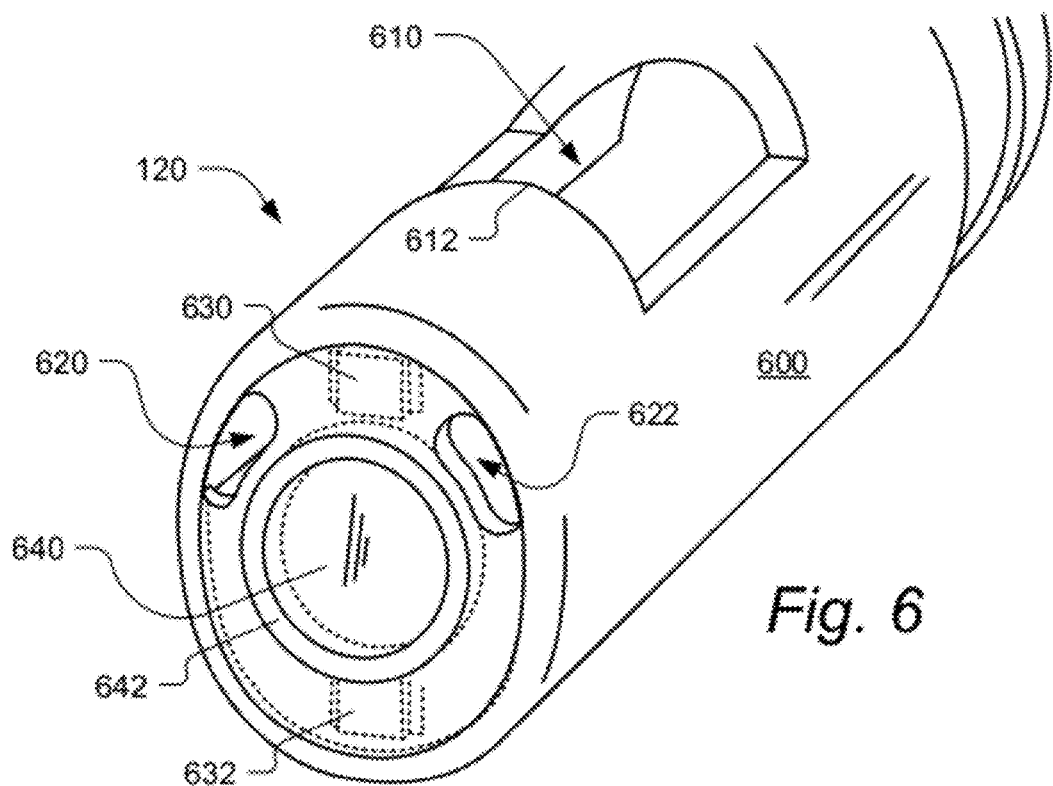
FIG. 6 is a prospective view of a distal tip of a device for combined hysteroscopy and endometrial biopsy according to some embodiments.

FIG. A1 illustrates an example medical device including an endoscope and sampling device, according to some embodiments;

FIG. A2 illustrates an example medical device according to some embodiments;

FIG. A3 illustrates an example medical device according to some embodiments disclosed herein;

FIG. A4 illustrates an example medical device according to some embodiments disclosed herein;

FIGS. A5A-A5C illustrate an example fluid and connector hub for use in a medical device according to some embodiments disclosed herein;

FIGS. A6A-A6B illustrate an example fluid and connector hub for use in a medical device according to some embodiments disclosed herein;

FIGS. A7A-A7C illustrate an example fluid and connector hub for use in a medical device according to some embodiments disclosed herein;

FIG. A8 illustrates an example medical device according to some embodiments disclosed herein;

FIG. A9 illustrates an example medical device according to some embodiments disclosed herein;

FIG. A10 illustrates an example medical device according to some embodiments disclosed herein;

FIG. A11 illustrates a flowchart of an example method of operating the medical device according to some embodiments disclosed herein;

FIG. A12 illustrates a flowchart of an example method of operating the medical device according to some embodiments disclosed herein; and FIG. A13 illustrates a flowchart of an example method of operating the medical device according to some embodiments disclosed herein;

FIGS. A14A-A14D illustrate a device for combined hysteroscopy and endometrial biopsy according to some embodiments;

FIGS. A15A-A15D illustrate a device at respective phases of a method for combined hysteroscopy and endometrial sampling according to some preferred embodiments;

FIGS. A16-A17 illustrate further detail of the handle and display portions of a sampling endoscope, according to some embodiments;

FIGS. A18A-A18D illustrate closer views of the distal end of a device for combined hysteroscopy and endometrial biopsy, according to some embodiments;

FIG. A19 illustrates various factors in optimal sensor design for single use video endoscopes, according to some embodiments;

FIGS. A20A-A20C illustrate details near the distal end of a device having combined hysteroscopy and endometrial sampling capability, according to some embodiments;

FIGS. A21A-A21B illustrate a sampling endoscope having a pistol grip, according to some embodiments;

FIGS. A22A-A22B illustrate an endoscope having optical fiber illumination, according to some embodiments;

FIGS. A23A-A23D illustrate details near the distal end of a device having combined hysteroscopy and endometrial sampling capability, according to some embodiments;

FIGS. A24A-A24B illustrate details near the distal end of a device having combined hysteroscopy and endometrial sampling capability, according to some embodiments;

FIGS. A25A-A25B illustrate details near the distal end of a device having combined hysteroscopy and endometrial sampling capability, according to some embodiments;

FIGS. A26A-A26B illustrate details near the distal end of a device having combined hysteroscopy and endometrial sampling capability, according to some embodiments;

FIGS. A27A-A27B illustrate details near the distal end of a device having combined hysteroscopy and endometrial sampling capability, according to some embodiments;

FIGS. A28A-A28B illustrate details near the distal end of a device having combined hysteroscopy and endometrial sampling capability, according to some embodiments;

FIGS. A29A-A29B illustrate details near the distal end of a device having combined hysteroscopy and endometrial sampling capability, according to some embodiments;

FIG. A30 is a cross sectional view illustrating further detail of a camera module for use with a device having combined hysteroscopy and endometrial sampling capability, according to some embodiments;

FIG. A31 illustrates a device having combined hysteroscopy and endometrial ablation capability, according to some embodiments;

FIGS. A32A-A32C illustrate the distal end of a device having combined hysteroscopy and endometrial ablation capability, according to some embodiments; and FIGS. A33A-A33C illustrate a device at respective phases of a method for combined hysteroscopy and endometrial ablation, according to some embodiments.

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding work, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

FIG. 1 is a left side view of a device for combined hysteroscopy and endometrial biopsy according to some embodiments. Many of the elements of the embodiments of hysteroscope 100 shown in FIG. 1 are the same as or similar to those discussed in the embodiments described in the commonly assigned incorporated applications, and such elements may not be described or may only briefly be described. It will also be appreciated that the aspects of the embodiments described in the commonly assigned incorporated applications may also apply to the embodiments described herein.

The device 100 is particularly advantageous for enabling a physician to perform an efficient combined hysteroscopic examination and an endometrial biopsy, although it is to be appreciated that other uses for hysteroscope 100 are within the scope of the present teachings. The hysteroscope 100 can bring about substantial efficiencies in terms of keeping equipment costs low and keeping the time required to perform the procedure modest, while at the same time providing the opportunity for better endometrial sample quality over conventional "blind" endometrial sample collection methods. Hysteroscope 100 includes a cannula 102, fluid hub 104, sliding connector 106, handle body 108, display mount 112 and display 110. The cannula 102 is made of a distal tip 120 and a shaft 122. The fluid hub includes one or more fluid ports 114 for delivering fluid into the device and thus into the uterus and/or for applying suction to extract fluid and tissue samples from the uterus. As shown the shaft 122 is curved near its distal end, for example having a 25 degree bend as shown. According to some embodiments, a bend of between 15 and 35 degrees near the distal end has been found to be suitable for many applications. The distal tip 120 includes a video camera assembly, lighting elements and fluid ports for in-flow (i.e. out of the device 100 and into the patient) and out-flow (i.e. into the device 100 and out of the patient). A sampling port on the upper side of the distal tip 120 also includes a cutting portion, which aids in tissue sample collection, as described in more detail below. The tip 120 includes a housing body that is made from acrylic, according to some embodiments. The shaft 122 is made from nylon, according to some embodiments. According to some embodiments the display 110 is a touch screen display, and is able to tilt upwards and downwards by, for example, about 45 degrees. According to some embodiments, in FIG. 1 as in other figures herein, various dimensions are shown that have been found to be suitable for many applications, but those skilled in the art may vary those dimensions without departing from the teachings of this patent specification. According to some embodiments, the cannula 102 (including the camera assembly, LED lighting and fluid ports integrated into the distal tip 120), fluid hub 104 and sliding connector 106 are designed for a single-use. According to these embodiments the cannula 102, fluid hub 104 and connector 106 are delivered to the medical practitioner in pre-sterilized package and are intended to be disposed of after a single-use, while the handle 108 and display 110 are designed to be re-used many times.

Figure 41:
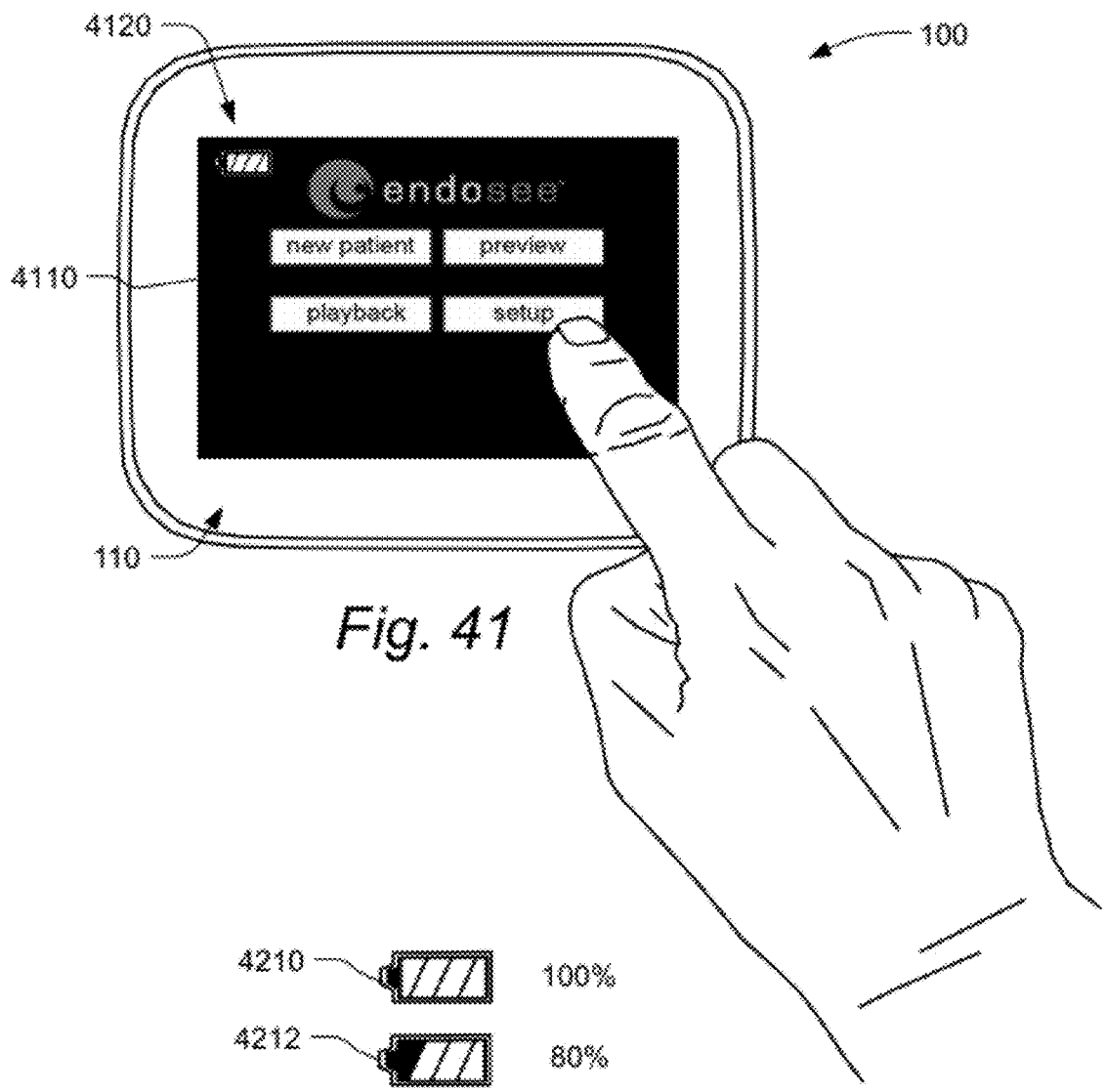
FIG. 41 is shows a display screen user interface for a hysteroscopy device, according to some embodiments.

FIG. 2 is a top plan view of a device for combined hysteroscopy and endometrial biopsy according to some embodiments. In this view, three control buttons are shown on the handle body 108. In particular, ON/OFF button 210 is used to toggle the device 100 on or off. According to some embodiments, the power ON/OFF button 210 is backlit using two differently colored LEDs to indicate the status of rechargeable battery 220 to the user. For example, green backlighting can be used to indicate the battery level is OK and red backlighting can be used to indicate the battery 220 is low (for example, less than 30% capacity remaining, such as used for icon 4218 shown in FIG. 42 infra). According to some embodiments the capacity of battery 220 is about 2500 mAh. According to some embodiments, the LED lighting of button 210 can also be used to indicate battery charging status during re-charging of the battery 220 from an external power source, such as when docked to a base station such as shown in FIGS. 36-37, infra, or when connected to a USB powered source using port 312 shown in FIGS. 3-4 infra. In this case, the backlighting LED shows red while charging the battery and green when the battery 220 is fully charged. According to some embodiments, the ON/OFF button 210 doubles as a "home" button, such that a shorter press, such as 1 second or less, of button 210 brings up a home screen menu on the display 110, as shown in FIG. 41, infra, while a longer press will turn the unit off.

LED brightness control button 212 is used to control the brightness of the LEDs on the distal tip 120. According to some embodiments a total of four different LED illumination levels has been found to be suitable and the single button 212 controls the level by cycling through the levels, changing the illumination level with each button press. The Snap/Video button 214 is used to capture still images and/or video from the camera in tip 120. According to some embodiments, pressing Snap/Video button 214 for three seconds or less captures a single still photo, while pressing button 214 for longer than three seconds starts video recording. When video is being recorded, a single press of button 214 stops video capture. Further details of the user interface which includes the buttons 210, 212 and 214 as well as the interactive touch screen display 110 are described with respect to FIGS. 41-46 infra. According to some embodiments, an audible acknowledgement signal is associated with presses of the buttons 210, 212 and 214. For example, a single "beep" is sounded when any of the buttons (including software buttons such as shown in FIGS. 41 and 43-46 infra.) except for double beeps when either the Snap/Video button 214 or an OK software button is pressed.

FIG. 3 is a right side view of a device for combined hysteroscopy and endometrial biopsy according to some embodiments. On the side of the display 110 is a rubber flap 310 that covers mini-USB port 312 and SD card slot 314. Flap 310 forms a fluid seal around the edge of the opening. Beneath the flap 310, the mini-USB port 312 serves multiple purposes including video-out to an external display, connector to an AC adapter for charging the rechargeable battery 220, and/or as a port to a host PC for downloading and uploading images, video and/or settings, as well as for charging the rechargeable battery 220. The SD card slot 314 is used to accept flash memory cards used to store images, video and/or settings for the device 100. According to some embodiments a standard size high-capacity (SDHC or SDXC) slot is provided, although smaller form factors such as Mini SD or Micro SD cards, or other types of storage media can be used.

FIG. 4 is a distal end view of a device for combined hysteroscopy and endometrial biopsy according to some embodiments. The tip 120 and shaft 122 can be seen, as well as the fluid hub 104, fluid port 114 and handle body 108. The SD card/USB port flap 310 is also shown on the side of the display body. Also shown, according to some embodiments is photo/video processing circuitry 410 that can be used to enhance or otherwise manipulate standard video signals and/or images received from the camera module in tip 120.

FIG. 5 is a proximal end view of a device for combined hysteroscopy and endometrial biopsy according to some embodiments. Touch-sensitive screen 110 is preferably 3.5 inches (diagonally) in size.

FIG. 6 is a prospective view of a distal tip of a device for combined hysteroscopy and endometrial biopsy according to some embodiments. Distal tip 120 includes a tip housing 600 that is made from acrylic, according to some embodiments. On the tip side of the tip 120 is the sampling port 610 used to draw fluid out of the patient's uterus as well as collect tissue. The sampling port 610 includes a cutting edge 612, which is sharp and positioned so as to facilitate collection of the endometrial sample by scraping. On the distal end of the tip 120 is camera assembly 640. Two LEDs 630 and 632 are positioned above and below the camera to evenly illuminate the uterine tissue for visual inspection. A light shield 642 acts a lens hood and shields direct light from the LEDs 630 and 632 from entering the aperture of the camera 640.

One problem in performing visual inspections of endometrial tissues, and particularly in situations where the endometrial medium, consisting of free tissue, loosely attached tissue and/or fluid, is relatively thick, is that light reflected from tissue particles suspended close to the lens can appear overly-bright and therefore impair imaging of other tissue surfaces. According to some embodiments, two forward facing fluid ports, 620 and 622 are provided to allow fluid to exit the tip and tend to push suspended particulate matter away from the camera so as to enhance image and video capture by camera 640. In some cases some tissue debris may collect on the distal surface such that imaging would be impaired in such cases the forward facing ports are useful in clearing away such collected tissue. Also it has been found that the forward facing ports are helpful in aiding insertion of the cannula in many cases as the fluid provides lubrication as well as a partial distending of tissues just ahead of the distal tip during insertion. Since the forward facing ports improve visualization, the risk of accidental damage to the uterus is greatly reduced.

Figure 7:
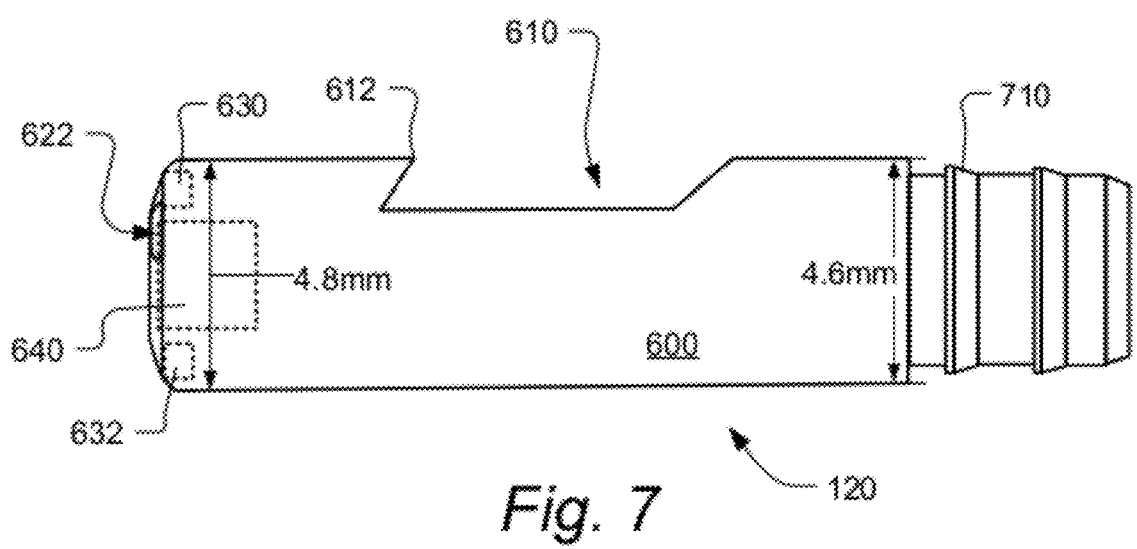
FIG. 7 is a left side view of a distal tip of a device for combined hysteroscopy and endometrial biopsy according to some embodiments.

FIG. 7 is a left side view of a distal tip of a device for combined hysteroscopy and endometrial biopsy according to some embodiments. The acrylic body 600 of the tip 120 preferably includes one or more ridges 710 to aid in securely fastening the tip 120 to the shaft 122 (not shown).

FIG. 8A is a right side view of a distal tip assembly of a device for combined hysteroscopy and endometrial biopsy according to some embodiments. In these embodiments, the forward facing in-flow (out of the device) fluid ports are connected to a separate fluid channel to enhance control over the fluid flowing into and out of the device 100. The tip 120 in this case includes separated fluid channels for fluid in-flow and out-flow. In particular a separate fluid channel 810, which runs along the upper right side, is connected to the front-facing fluid port 620, and another fluid channel, not shown, is connected to the other front-facing fluid port 622, not shown. A central fluid channel 820 is connected to the side sampling port 610.

FIGS. 8B-8E are further views of the distal tip assembly of a device for combined hysteroscopy and endometrial biopsy according to some embodiments. FIG. 8B is a proximal end view of the tip 120 shown in FIG. 8A. The tip body or housing 600 includes two in-flow (out of the device and into the patient) channels 810 and 812 that are fluidly connected to the two in-flow front-facing ports, and a central channel 820 that is fluidly connected to the sampling port 610. The central channel 820 is also used to run a video and control cable from the camera assembly towards the handle and the display. FIG. 8C is a sectional view of the distal tip along the line A-A' shown in FIG. 8A. Note that the tip housing 600 is made of an outer sleeve 830 and a core 832, according to some embodiments. FIG. 8D is a sectional view of the distal tip along the line B-B' shown in FIG. 8A, and shows the connection between the central fluid channel 820 and the sampling port 610. FIG. 8E is a distal end view of the tip assembly 120 shown in FIG. 8A. According to some embodiments, the tip 120 outer dimensions are slightly larger toward the distal end. For example, the tip body 600 measures 3.8 mm×4.6 mm at the proximal end, shown in FIG. 8B, and measures 4.2 mm×4.8 mm at the distal end, shown in FIG. 8E.

Figure 9:
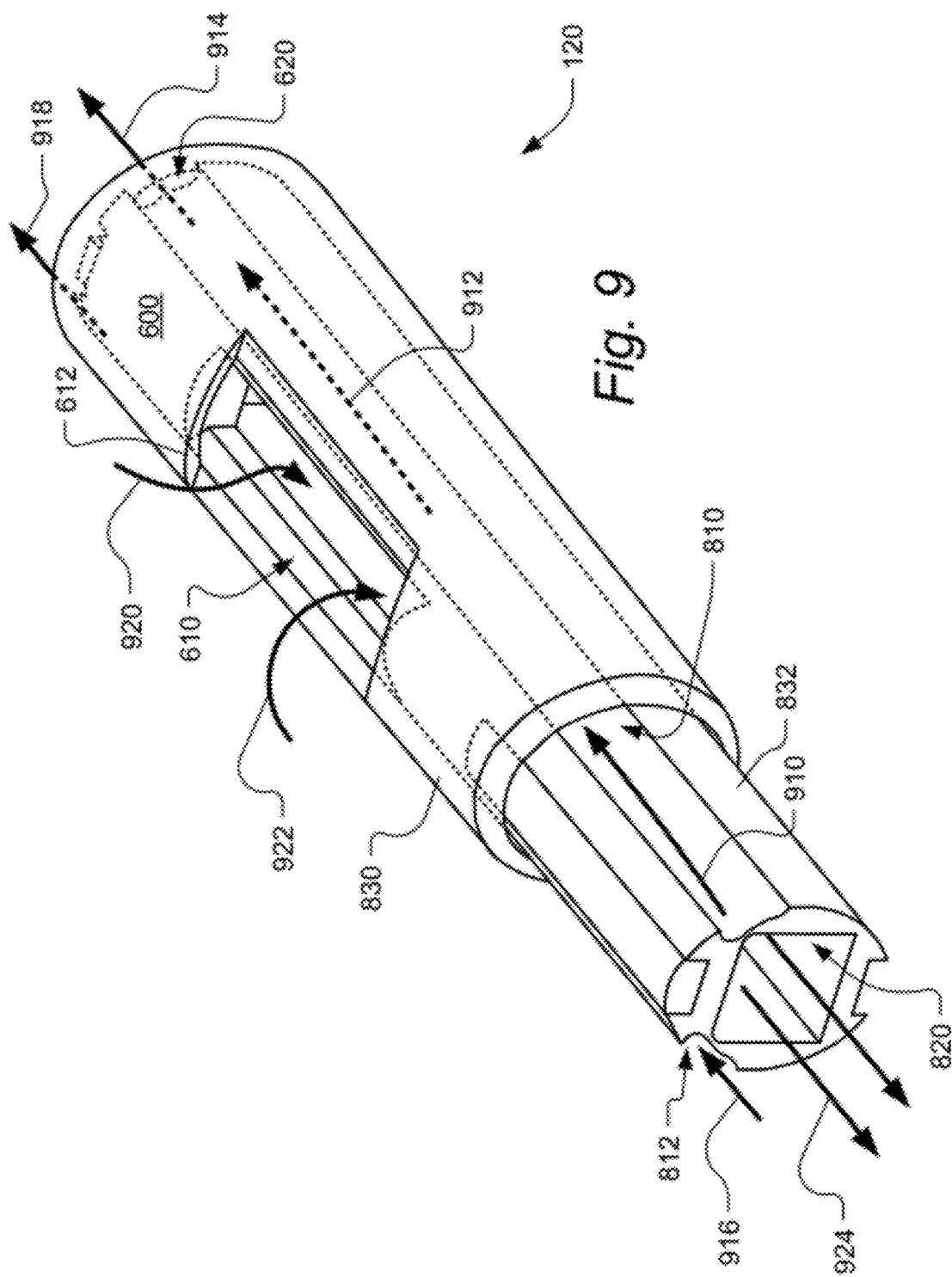
FIG. 9 is perspective view of a distal tip of a device for combined hysteroscopy and endometrial biopsy according to some embodiments.

FIG. 9 is perspective view of a distal tip of a device for combined hysteroscopy and endometrial biopsy according to some embodiments. This view of the distal tip assembly 120 shows fluid direction arrows such as arrows 910, 912 and 914 for fluid flowing through channel 810 and out of front-facing port 620. The arrows 916 and 918, similarly, show the direction of fluid flowing in channel 812. The arrows 920, 922 and 924 show the direction of fluid from sampling port 610 and through the central channel 820.

Figure 10:
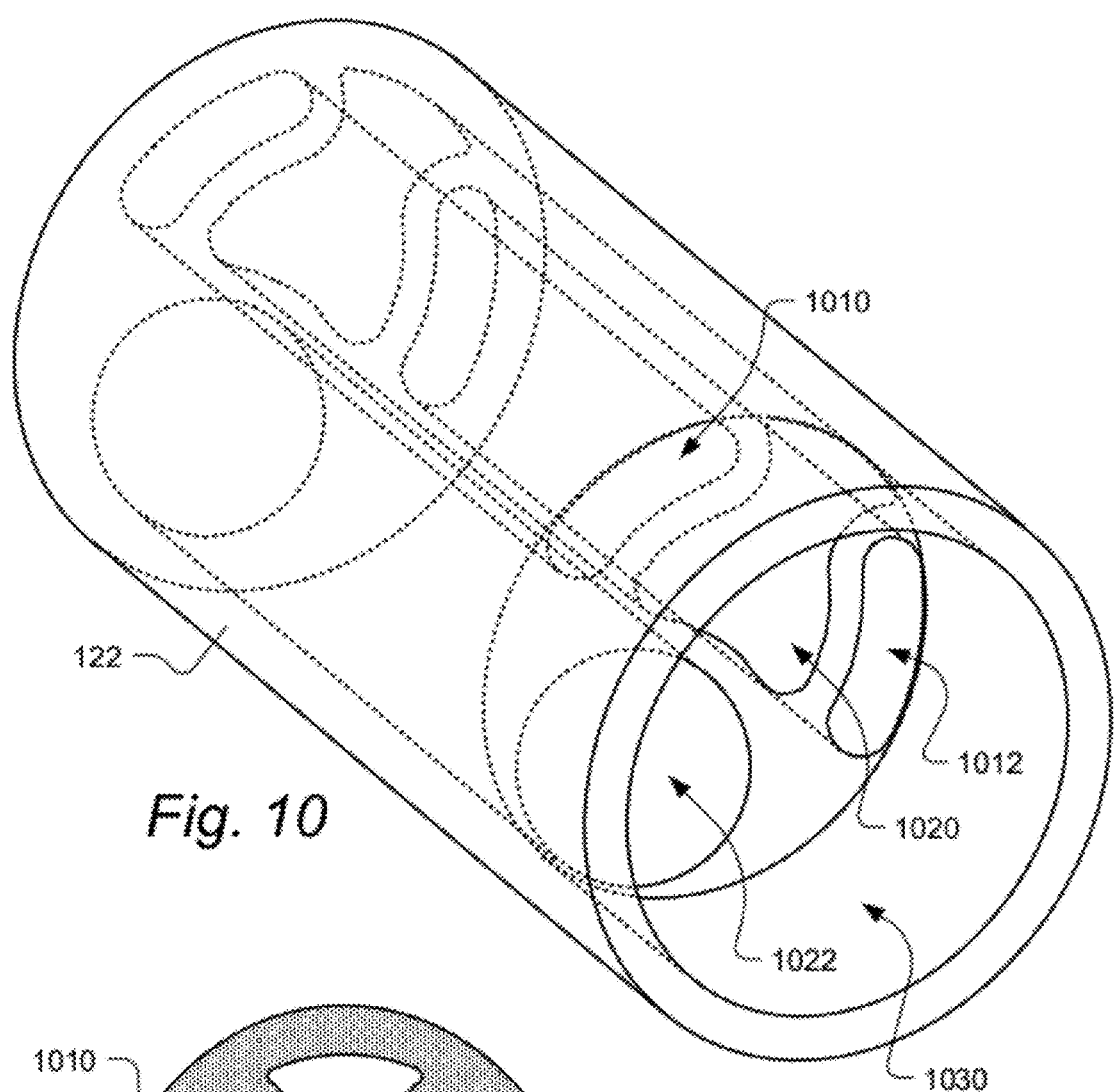
FIGS. 10 and 11 show details of the internal structure of the shaft having separated fluid channels of a device for combined hysteroscopy and endometrial biopsy according to some embodiments.
Figure 11:
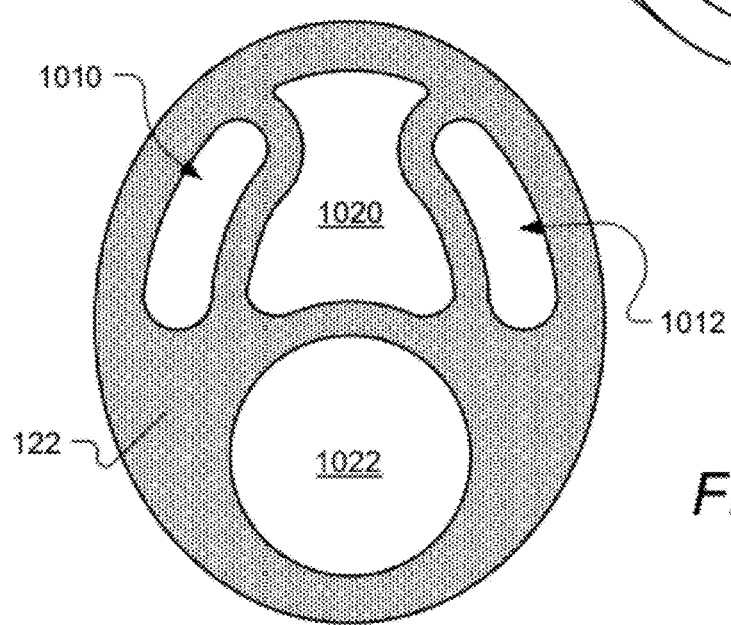

FIGS. 10 and 11 show details of the internal structure of the shaft having separated fluid channels of a device for combined hysteroscopy and endometrial biopsy according to some embodiments. FIG. 10 is a perspective view of the distal end of the shaft 122. The distal end 1030 of the shaft 122 has the internal structure removed so as to be able to mate with the proximate end of the tip 120. The shaft 122 has separate channels 1010 and 1012 that are aligned so as to fluidly mate with channels 810 and 812 respectively on tip 120. The upper central channel 1020 is used for the out-flow fluid (i.e. into the device) for removing fluid from the uterus and/or to provide negative pressure for tissue sample collection. The channel 1020 is thus positioned to fluidly mate with central channel 820. Also included is a separate channel 1022 that is used to house the video and camera control cable, which also passes through the central channel 820 of tip 120. FIG. 11 is a cross section of the shaft 122. According to some embodiments, the shaft 122 is made from extruded nylon.

Figure 12:
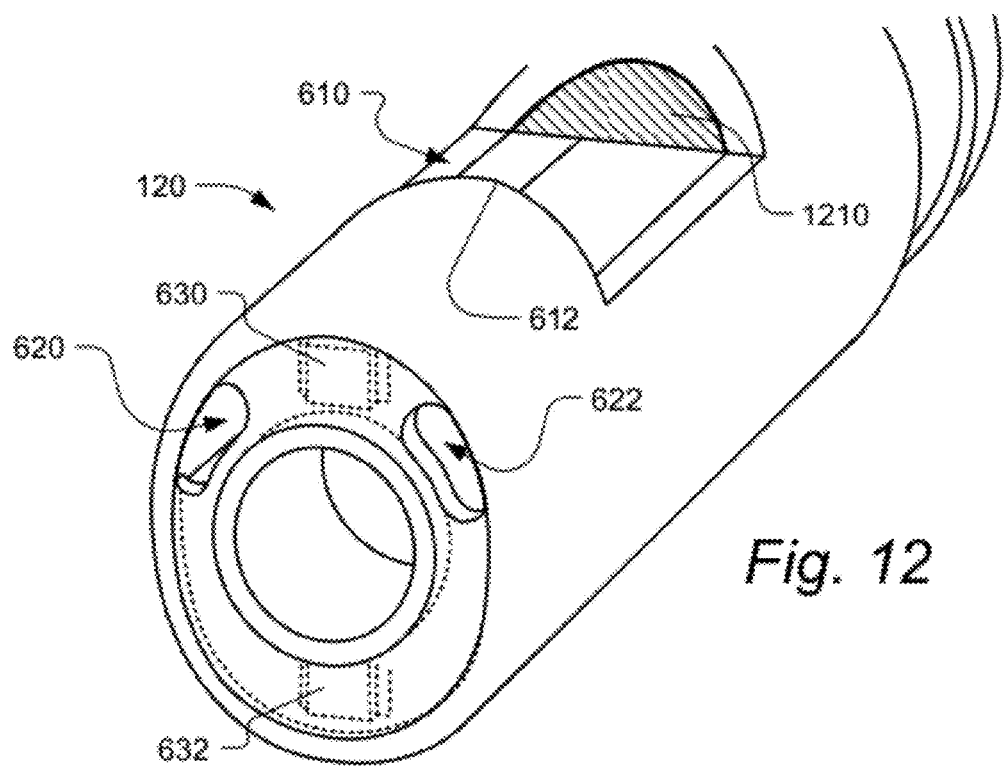
FIGS. 12, 13 and 14 show internal structures of a distal tip of a device for combined hysteroscopy and endometrial biopsy according to some alternate embodiments.
Figure 13:
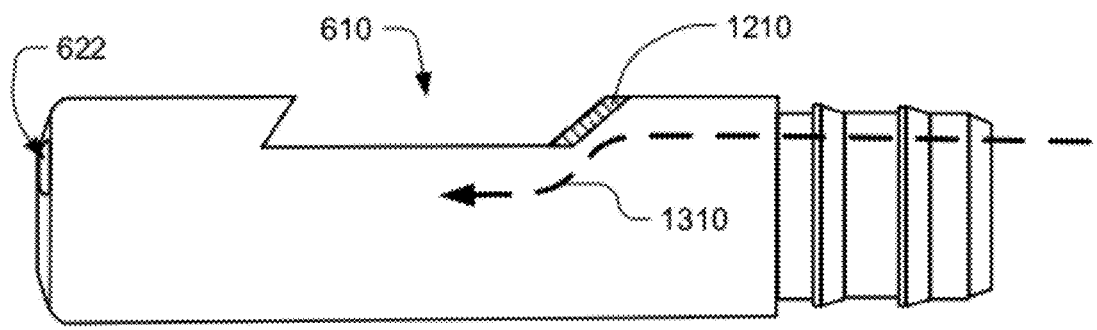
Figure 14:
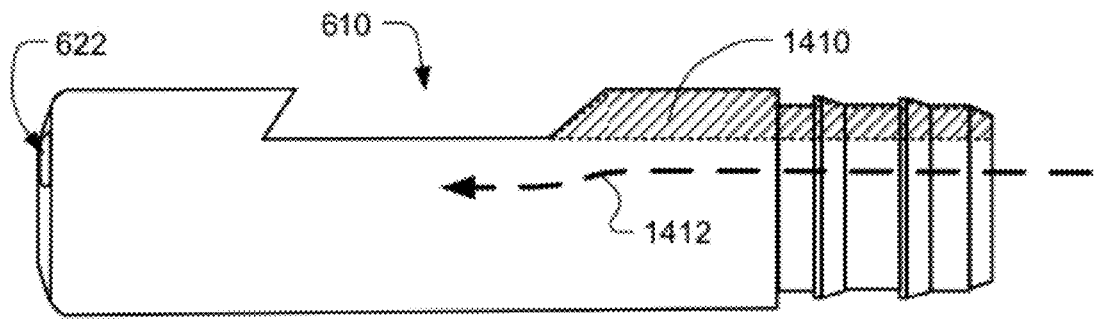

FIGS. 12, 13 and 14 show internal structures of a distal tip of a device for combined hysteroscopy and endometrial biopsy according to some alternate embodiments. FIGS. 12-14 show two embodiments wherein the in-flow and out-flow paths are not separated as in the case of the embodiments of FIGS. 8A-E and 9. In the case where the flow paths are not separated, the tip 120, shaft 122 and fluid hub 104 can be more structurally simplified. However, due to the relative sizes of the forward facing fluid ports 610 and 612 on the one hand and the side-facing port 620 on the other, certain structural elements may be included to ensure adequate fluid flow out of the front facing ports 610 and 612 during times when useful to improve visual inspection. In the case of FIGS. 12 and 13, an element 1210 is included just behind the sampling port 610 to direct the fluid towards the forward-facing ports as shown by arrow 1310 in FIG. 13. In the case of FIG. 14, the upper section 1410 is filled in solid so as to aid in directing the fluid towards the forward-facing ports as shown by arrow 1412.

Figure 15:
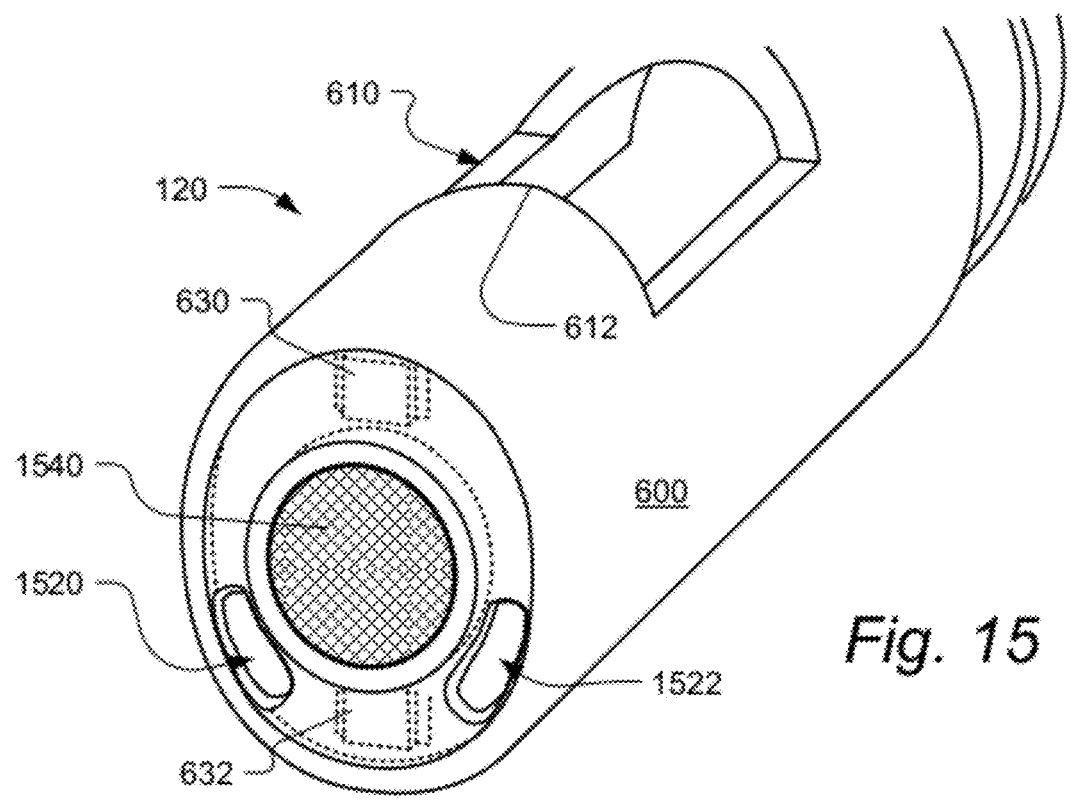
FIGS. 15-16 show a distal tip of a device for combined hysteroscopy and endometrial biopsy according to some alternate embodiments.
Figure 16:
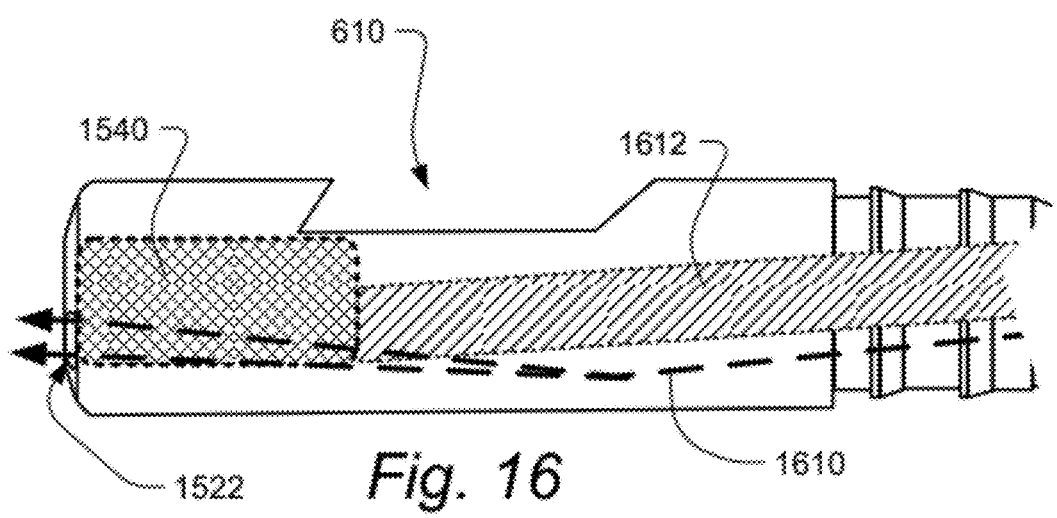

FIGS. 15-16 show a distal tip of a device for combined hysteroscopy and endometrial biopsy according to some alternate embodiments. FIGS. 15-16 show a further embodiment wherein the in-flow and out-flow paths are not separated as in the case of the embodiments of FIGS. 8A-E and 9. In this case, the two forward-facing fluid ports 1520 and 1522 are positioned lower on the distal tip 120 such that the camera module 1540 and the video cable 1612 tend to force the in-flow direction fluid (i.e. out of the tip 120) under the cable 1612 and toward the ports 1520 and 1522 rather than out of the side-facing sampling port 610. The arrows 1610 show example fluid flow paths in the in-flow direction (out of the device). According to other embodiments other internal structures can be provided in addition to or in place of those shown in shown in FIGS. 12-16 to enhance flow through the forward facing ports.

Figure 17A:
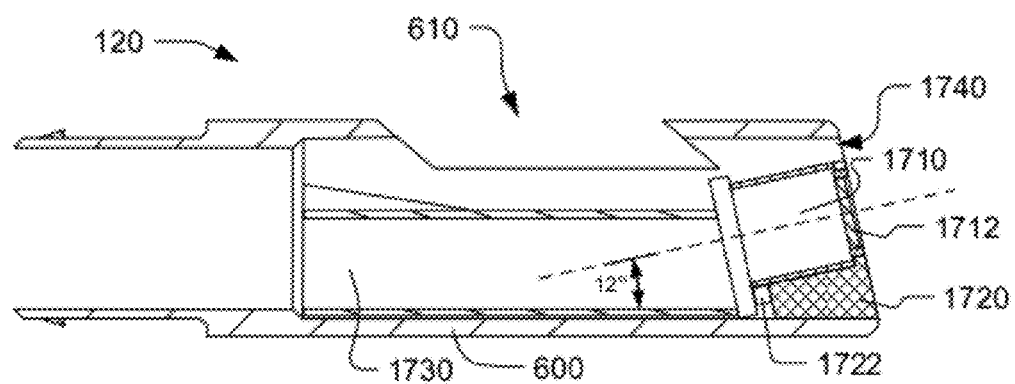
FIGS. 17A-17B show a distal tip of a device for combined hysteroscopy and endometrial biopsy having an up-tilted camera module, according to some embodiments.
Figure 17B:
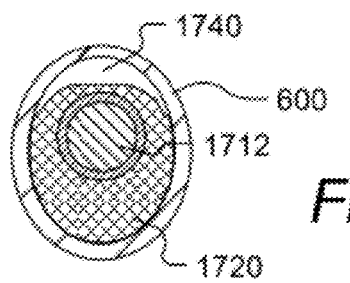

FIGS. 17A-17B show a distal tip of a device for combined hysteroscopy and endometrial biopsy having an up-tilted camera module, according to some embodiments. In FIG. 17A, it can be seen that camera 1710 is tilted up at an angle of, e.g., 12 degrees from the longitudinal axis of the tip body or housing 600. The upwards tilting of the camera increases the effective field of view of the device. Also shown in FIGS. 17A and 17B is a glass cover 1712 of camera module 1710. A light guide 1720 is also used to diffuse light from one or more LEDs, such as LED 1722. The light guide 1720, as shown in FIG. 17B surrounds the camera module 1710. The light guide 1720 can be made of glass or a polymer, for example. Also shown in this example is a forward facing fluid port 1740 which is useful in directing fluid in a forward direction so as to enhance visual inspection.

Figure 18A:
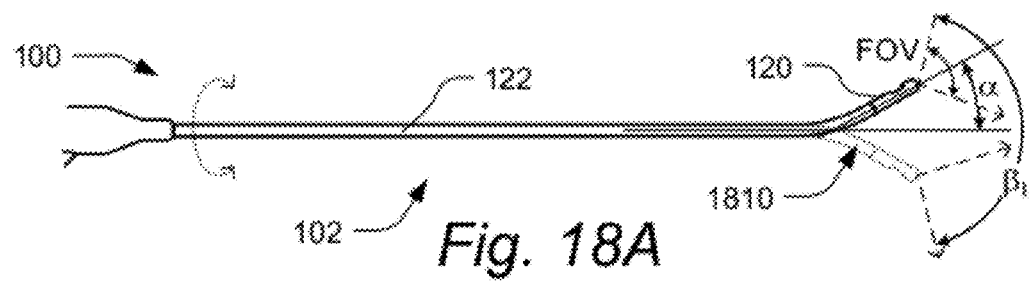
FIGS. 18A-18B illustrate how camera tilting effects effective field of view for a device for combined hysteroscopy and endometrial biopsy, according to some embodiments.
Figure 18B:
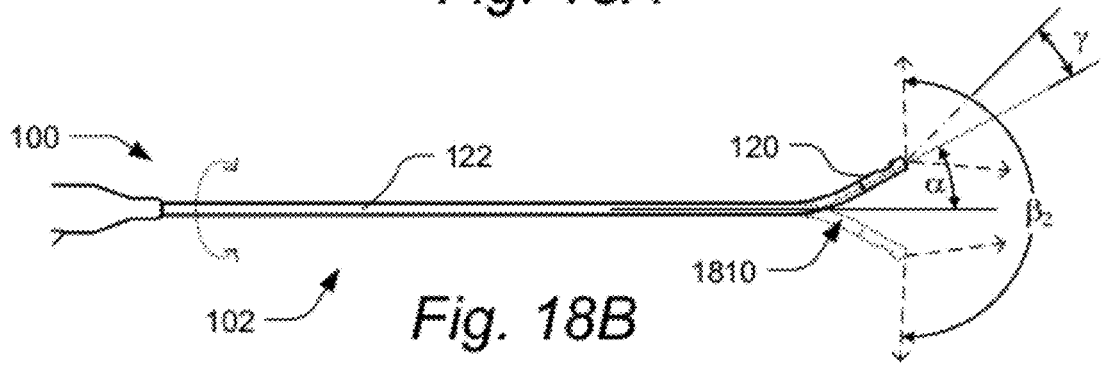

FIGS. 18A-18B illustrate how camera tilting provides a larger effective field of view for a device for combined hysteroscopy and endometrial biopsy, according to some embodiments. During visual inspection of the uterine tissues, the device 100 is rotated about its longitudinal axis by the doctor or medical professional. The position of the cannula 102 when rotated 180 degrees, is shown by the dotted outline 1810. The field of view (FOV) of the camera module in this example is shown which combined with the bending of the shaft 122 by and angle α, results in an effective field of view in the case of FIG. 18A of $\beta_1$. In the case of FIG. 18B, the camera is tilted upwards by an angle of γ, which results in an increase in effective field of view by twice γ, due to the rotation of the device. The effective field of view of the device 100 in FIG. 18B is shown as $\beta_2$.

Figure 19:
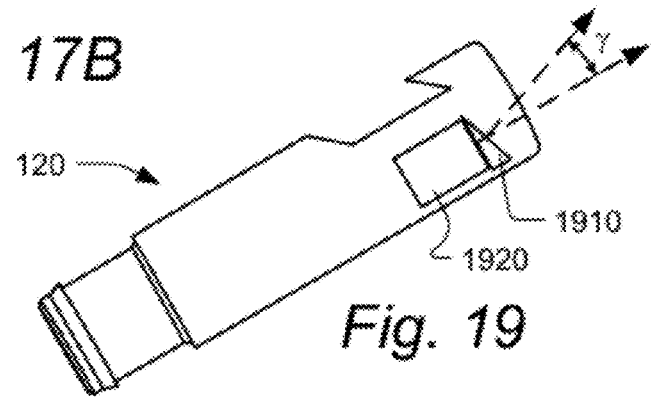
FIG. 19 shows a distal tip of a device for combined hysteroscopy and endometrial biopsy having a prism-aided tilted camera view, according to some embodiments.

FIG. 19 shows a distal tip of a device for combined hysteroscopy and endometrial biopsy having a prism-aided tilted camera view, according to some embodiments. In this case a prism 1910 is used to modify the angle of the camera module 1920 to provide an effective upwards tilting of the field of view of the camera module 1920 by an angle γ, which will result in an increased effective field of view of the device during use by two times γ.

Figure 20A:
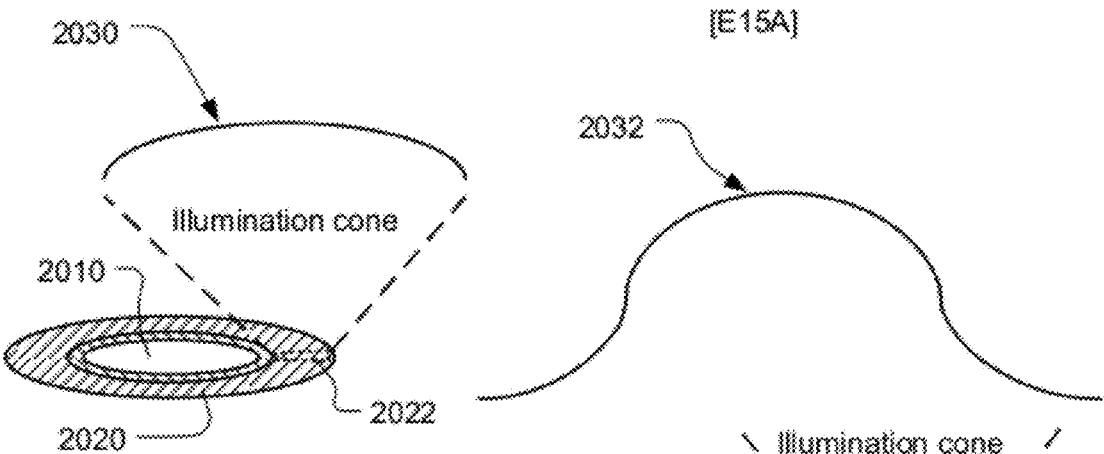
FIGS. 20A-20B and 21A-21B show examples of ring-type LEDs for use with a hysteroscopy device, according to some embodiments.
Figure 20B:
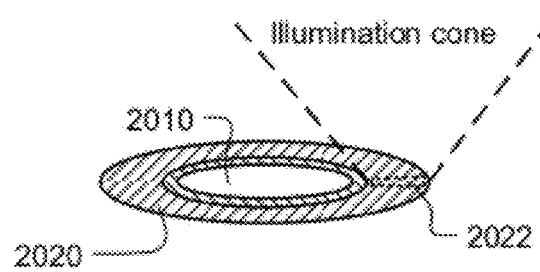
Figure 21A:
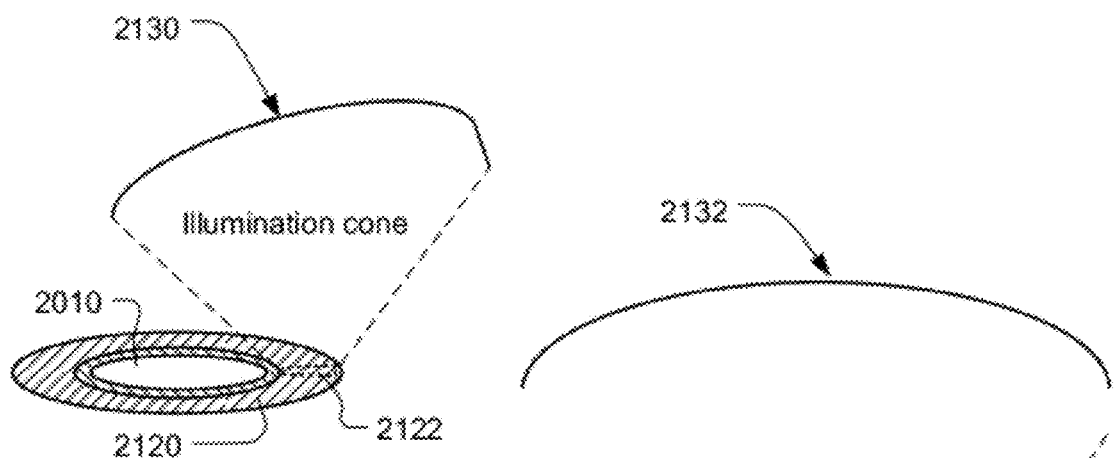
Figure 21B:
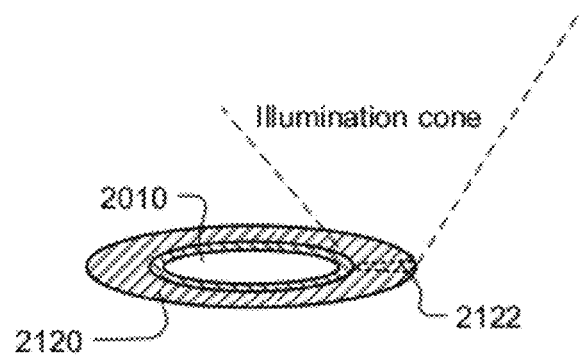

FIGS. 20A-20B and 21A-21B show examples of ring-type LEDs for use with a hysteroscopy device, according to some embodiments. In FIGS. 20A and 20B, a ring-type LED 2020 is shown surrounding a camera module 2010 that is used on the distal tip of a hysteroscopy device, such as device 100 described herein. In FIG. 20A, the illumination intensity distribution curve 2030 represents illumination from a single LED sector 2022 from ring LED 2020. In FIG. 20B, the overall illumination distribution curve 2032 represents the illumination from the entire ring LED 2020. Note that the center is much brighter than the edges, which may be problematic for imaging under some circumstances. According to some embodiments, a more evenly distributed intensity is achieved using an ring-type LED as shown in FIGS. 21A and 21B. In FIG. 21A, the ring type LED 2120 is shown surrounding a camera module 2010 that is used on the distal tip of a hysteroscopy device, such as device 100 described herein. The illumination intensity distribution curve 2130 represents illumination from a single LED sector 2122 from ring LED 2120. Note that the intensity is unevenly distributed towards the outer edge of the ring. The intensity profile is adjusted, for example, by using different thicknesses or orientations of the LED. FIG. 21B shows the resulting overall intensity distribution 2132 from ring LED 2120 where the center is more even with the edges, which results in enhanced imaging quality.

Figure 22:
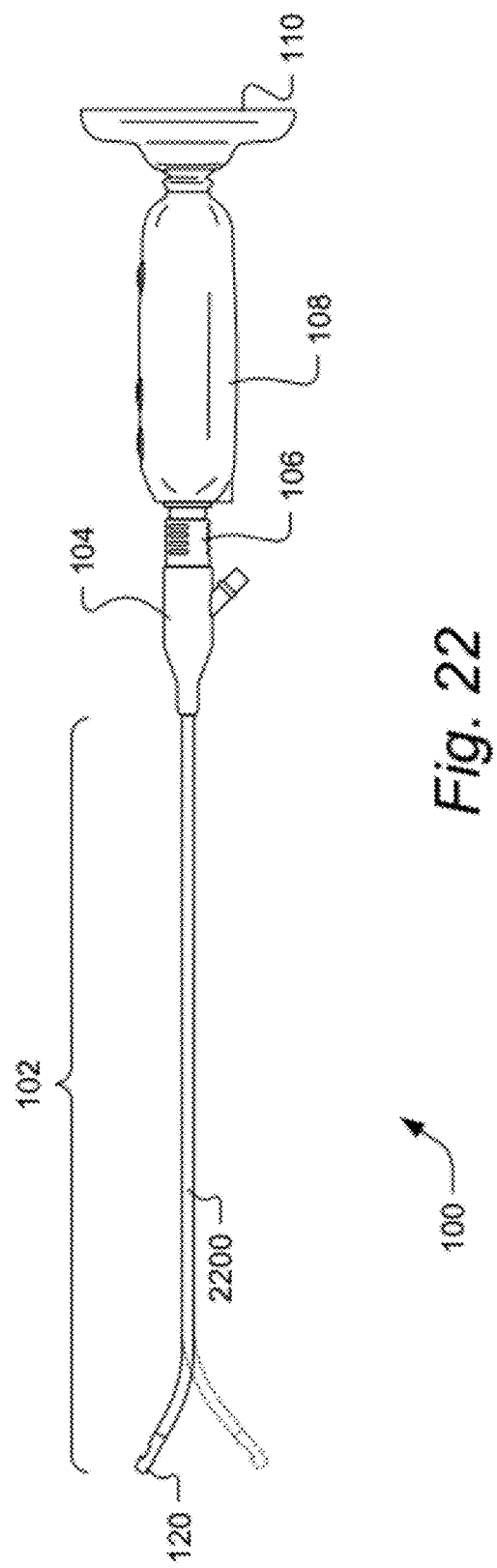
FIG. 22 shows a device for combined hysteroscopy and endometrial biopsy having malleable shaft, according to some embodiments.

FIG. 22 shows a device for combined hysteroscopy and endometrial biopsy having malleable shaft, according to some embodiments. In this example, cannula 102 includes a malleable shaft 2200. The shaft 2200 is malleable at the time of usage to aid reaching and visualizing recessed portions of the uterine cavity. The shaft 2200 can be made malleable, for example, by using a flexible nylon that includes one or more bendable metal wires running along the inside length of the shaft housing.

Figure 23:
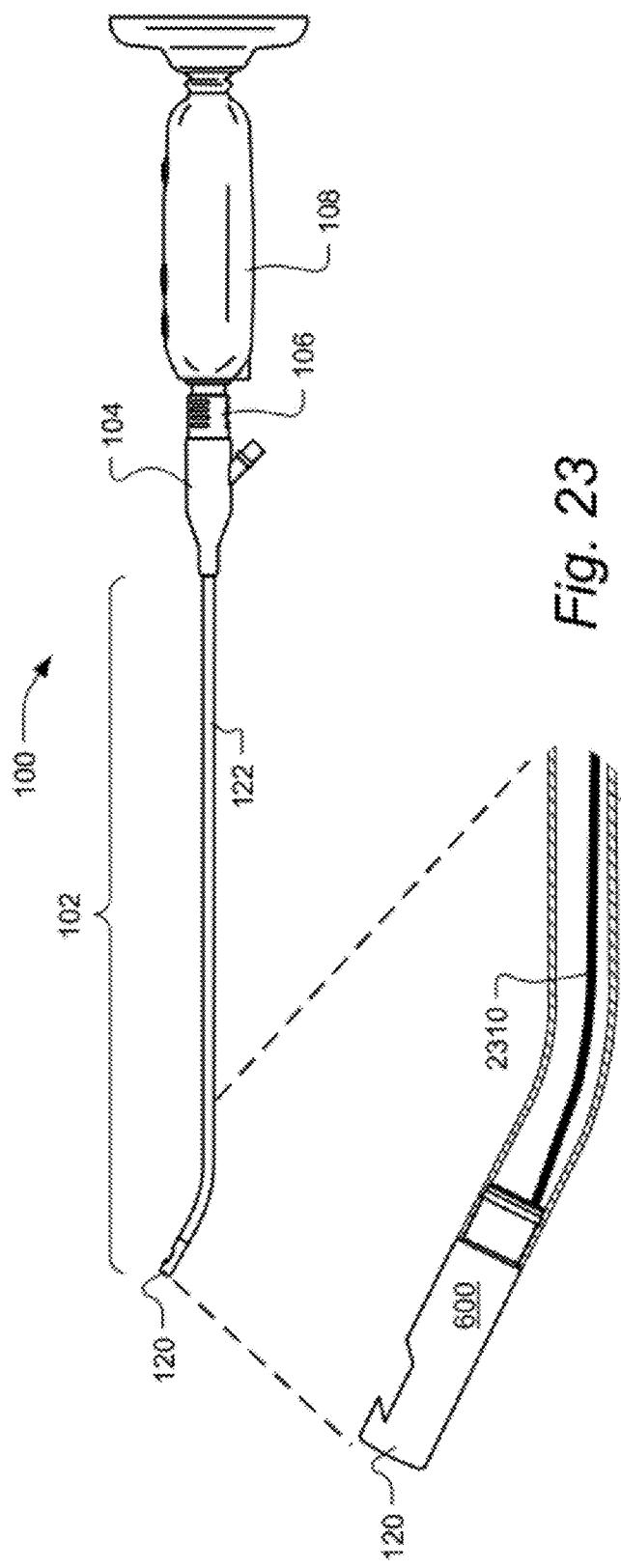
FIGS. 23 and 24 show details of the a device for combined hysteroscopy and endometrial biopsy having separate tip and shaft assemblies, according to some embodiments.
Figure 24:
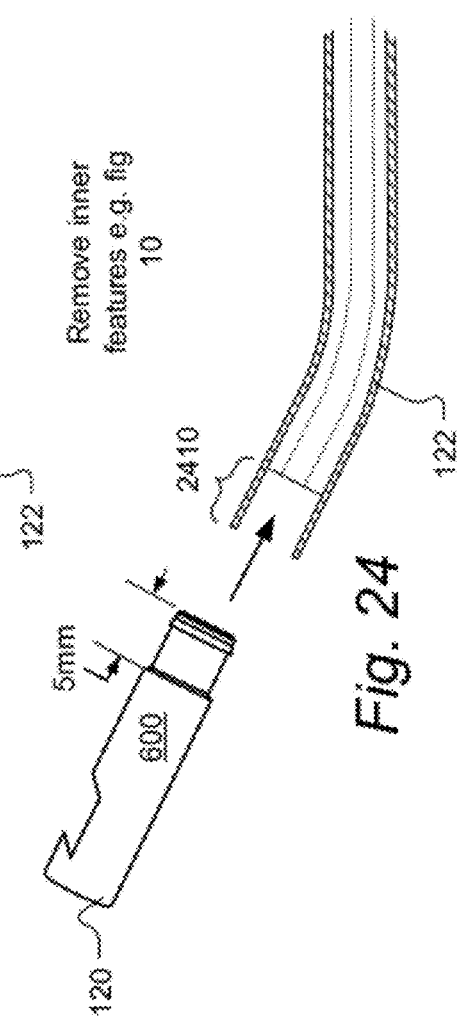

FIGS. 23 and 24 show details of a device for combined hysteroscopy and endometrial biopsy having separate tip and shaft assemblies, according to some embodiments. The cannula 102 of device 100 is made up of a tip 120 and a shaft 122. The tip 120 includes a molded acrylic tip housing 600 that houses the camera module, LEDs and other elements as described herein. The shaft 122 is made from extruded nylon, such as nylon 6, and may have internal structure such a shown in FIGS. 10, 26-28. According to some embodiments, shaft 122 can be made of another suitable material, such as Provista Copolymer. In FIG. 23 a video cable 2310 is also shown running along the inside of shaft 122 which carries video signals as well as control signals for the camera module and/or the LEDs in the tip 120. FIG. 24 shows how the tip assembly 120 is attached to the shaft 122. According to some embodiments, about 5 mm or more of the tip 120 is inserted into the shaft 122. If there are internal structures such as shown in FIGS. 10, and 26-28, they are spaced inwardly from the distal end of the shaft 122 so that proper mating can be achieved. Through the implementation of separately manufactured tip and shaft pieces, as shown, it has been found that the manufacturing cost can be decreased, and yield can be increased because the shaft is extruded while the acrylic tube is molded to provide sophisticated structure. Furthermore, the separate tip and shaft design allows for greater flexibility in forming the internal structures within both the tip and shaft.

Figure 25:
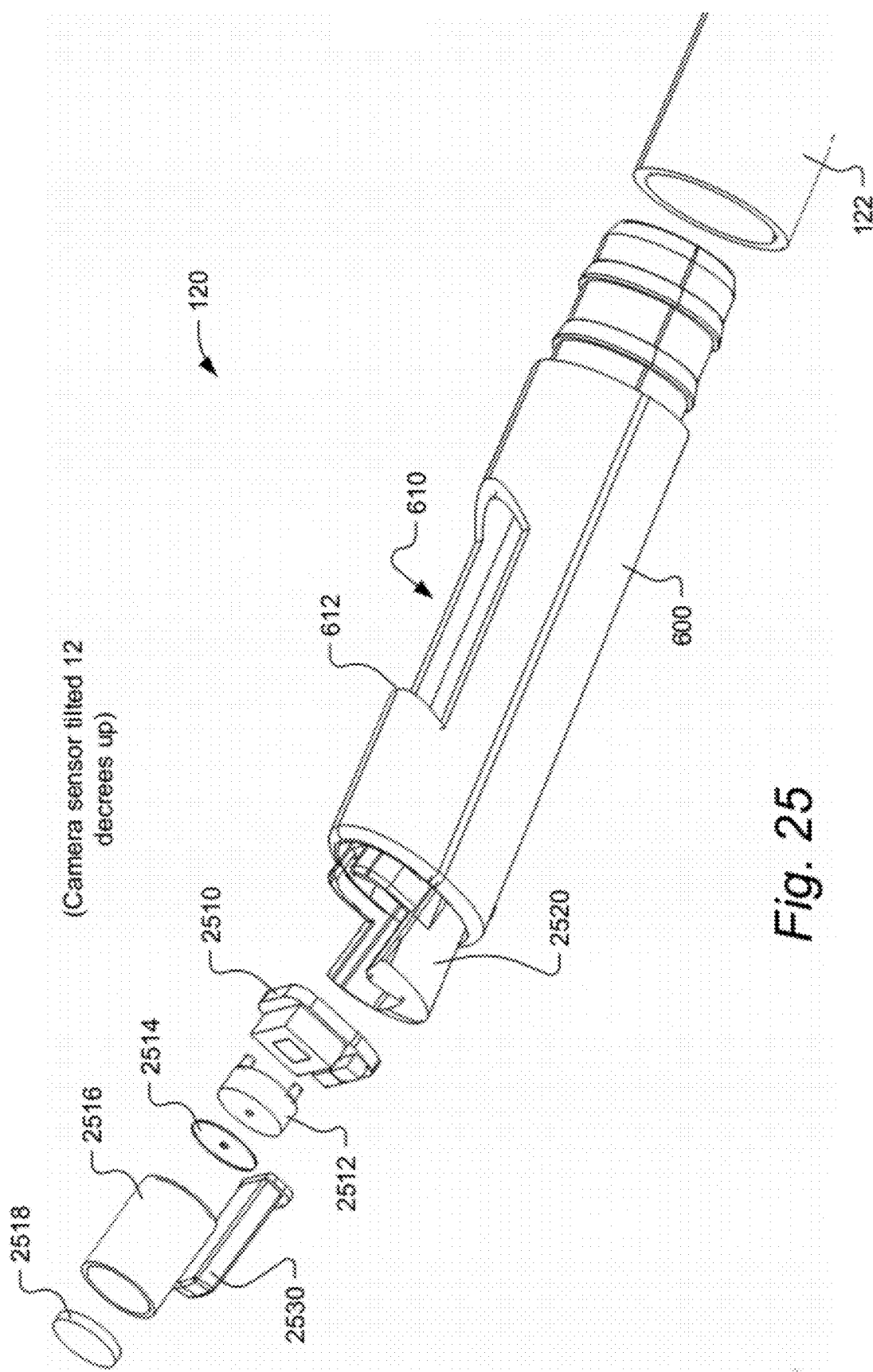
FIG. 25 is an exploded view of some internal components of a distal tip of a device for combined hysteroscopy and endometrial biopsy, according to some embodiments.

FIG. 25 is an exploded view of some internal components of a distal tip of a device for combined hysteroscopy and endometrial biopsy, according to some embodiments. In this example, tip assembly 120 is shown with various parts of the camera module separated for ease of viewing. The camera module includes CMOS sensor module 2510, lens 2512, iris 2514, shield 2516 and glass cover 2518. The CMOS sensor module 2510 includes a low voltage color CMOS image sensor core, image sensor processing and image output interface circuitry on a single chip such as the OmniVision 7675. By providing integrated digital video processing within sensor module 2510, all video processing can be performed directly on the same PCB as the CMOS sensor, or on the same substrate in which the CMOS is formed such that the imaging plane of the CMOS and the plane along which the video processing circuits extend substantially coincide. In this example, the video signal from sensor module 2510 can be in any suitable video format, such as NTSC, PAL, or another common video format, so that no further video processing would be required to drive widely available displays for common video formats such as TV displays, tablets, computers and hospital workstations. Also shown in FIG. 25 are one or more LEDs 2530. According to some embodiments another LED can be used mounted above the camera module. The holder 2520 retains the camera module and LEDs. According to some embodiments, the holder 2520 holds the camera module at an up-tilted angle of for example 12 degrees from the longitudinal axis of the tip housing 600.

Figure 26:
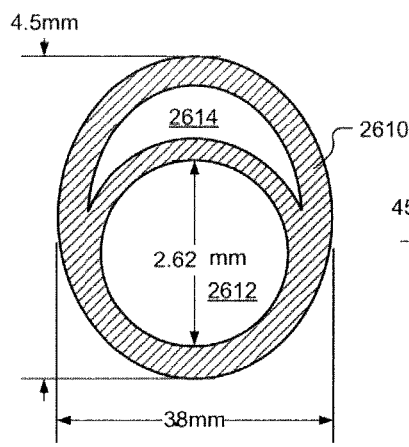
FIGS. 26-28 are cross sections showing examples of different internal shaft structures within a cannula for a device for combined hysteroscopy and endometrial biopsy, according to some embodiments.
Figure 27:
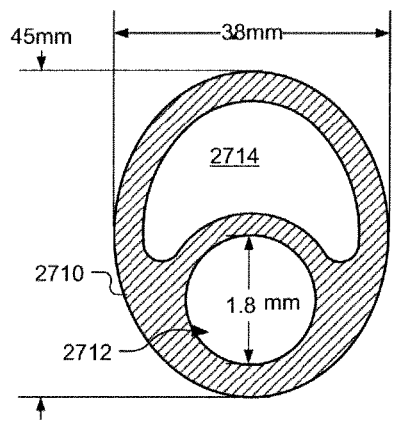
Figure 28:
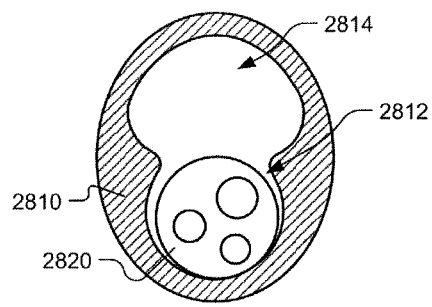

FIGS. 26-28 are cross sections showing examples of different internal shaft structures within a cannula for a device for combined hysteroscopy and endometrial biopsy, according to some embodiments. In FIG. 26, shaft 2610 includes a separate channel 2612 for the cable used for video and control signals as well as LED power. The upper channel 2614 is used for as the fluid channel for both in-flow and out-flow directions. Similarly, in FIG. 27, shaft 2710 includes a separate channel 2712 for the cable, while an upper channel 2714 is used for as the fluid channel for both in-flow and out-flow directions. In the example of FIG. 28, a partially separated internal structure is used. The shaft 2810 includes an upper lobe 2814 used for fluid flow and a lower lobe 2812 that primarily holds the cable 2820 used for LED power, video signals and control signals for the camera. The structure of FIG. 28 allows for simplified assembly since it is easier to position the cable 2810 in the lower lobe than to thread or fish it through a separate channel.

FIGS. 29 and 30 show further details of a distal tip for a device for combined hysteroscopy and endometrial biopsy, according to some embodiments. FIG. 29 is a perspective view of the distal tip 120 and distal end of shaft 122, according to some embodiments. As in some other described embodiments, the tip 120 includes a tip housing body 600 that is made from molded acrylic, for example a single molded piece of transparent acrylic. The tip 120 includes a side facing sampling port 610 and front facing fluid port 2940. A forward facing camera module includes a glass cover 1712 and in this case an acrylic camera module housing shell 2910. Two forward facing LEDs 2920 and 2922 are positioned just below the glass cover 1712. The cable 1612 used for LED power, video signals and control signals for the camera is also shown running down the shaft 122. FIG. 30 is a cross section of the tip and shaft shown in FIG. 29.

Conventional endoscopes are typically tethered and cumbersome to use. They require skilled staff to operate and maintain. This makes it especially difficult in time critical locations such as an emergency room, operating room, and other areas of a medical facility where multiple devices and instruments are being used simultaneously. According to some embodiments, the device 100 shown for example in FIGS. 1-5 is a hand-held, compact single use endoscope. In these cases, endoscope 100 is provided in a sterile package, so is ready for immediate use without requiring any preparation for diagnostic or therapeutic procedures. According to some embodiments the single use device 100 needs no sophisticated connectors such that the entire endoscope is supplied in a sterile package ready for use.

Figure 31:
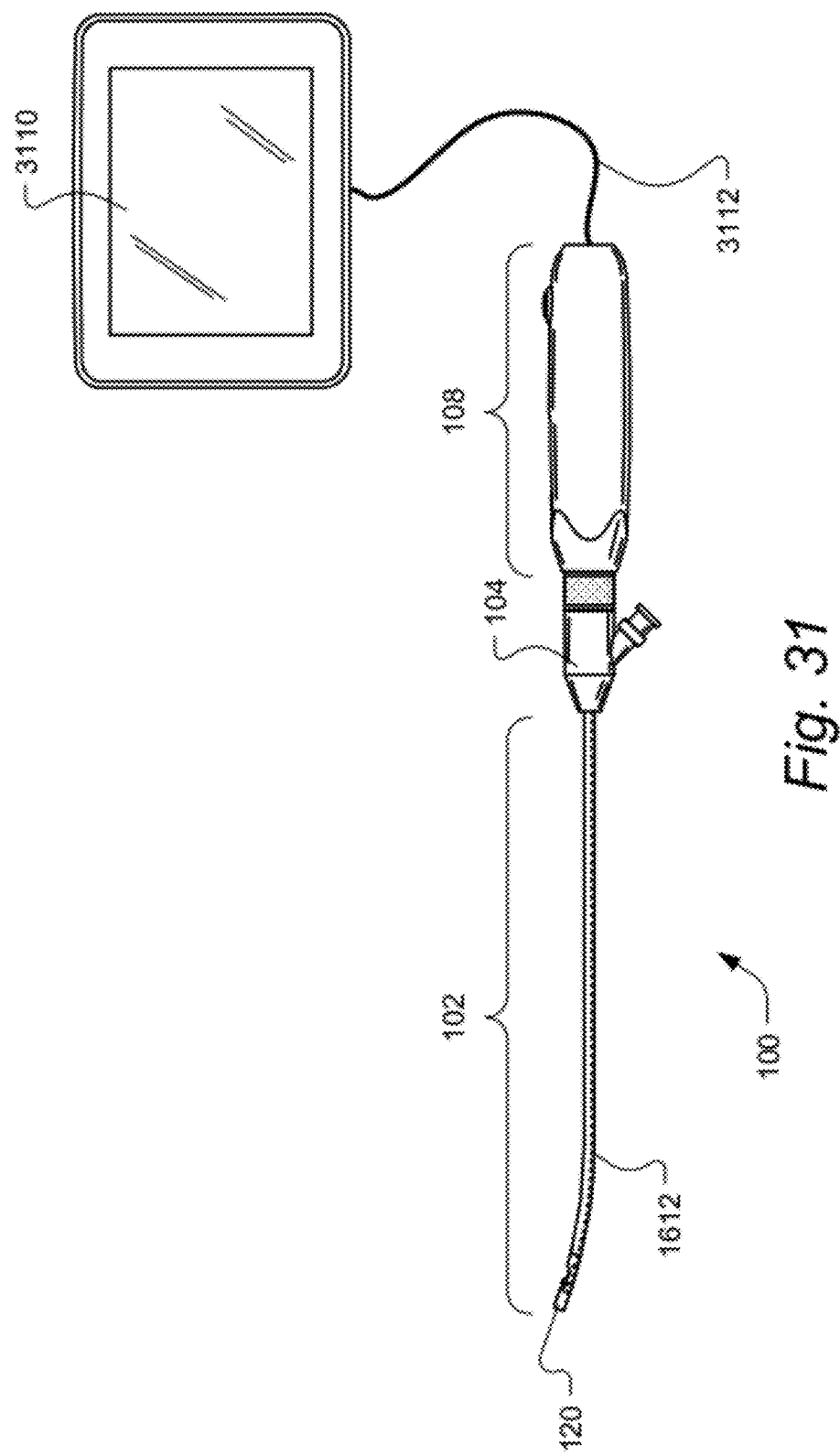

FIGS. 31-33 show a single-use device for combined hysteroscopy and endometrial biopsy, according to various embodiments. In the case of FIG. 31, device 100 includes an external monitor 3110 for viewing the images and/or video. A sterile cord 3112, which transmit the images and video to the external monitor, is attached to and is packaged with the device 100.

In the case of device 100 of FIG. 32, the images and video are transmitted by a wireless connection. The handle 100 includes a wireless transmitter 3212 and the eternal monitor 3210 includes a wireless receiver. According to some embodiments Wi-Fi technology is used. According to some embodiments, a device such as a smart phone 3220, a tablet computer 3222, a mobile computer, or other mobile device having wireless and display capabilities are used to view the images and/or video.

In the case of FIG. 33, the device 100 includes a gyroscopic module 3310 embedded to provide constant reference of orientation. A video processor is used to register the displayed images upright on the devices such as devices 3210, 3110, 3220 and 3222.

Figure 34:
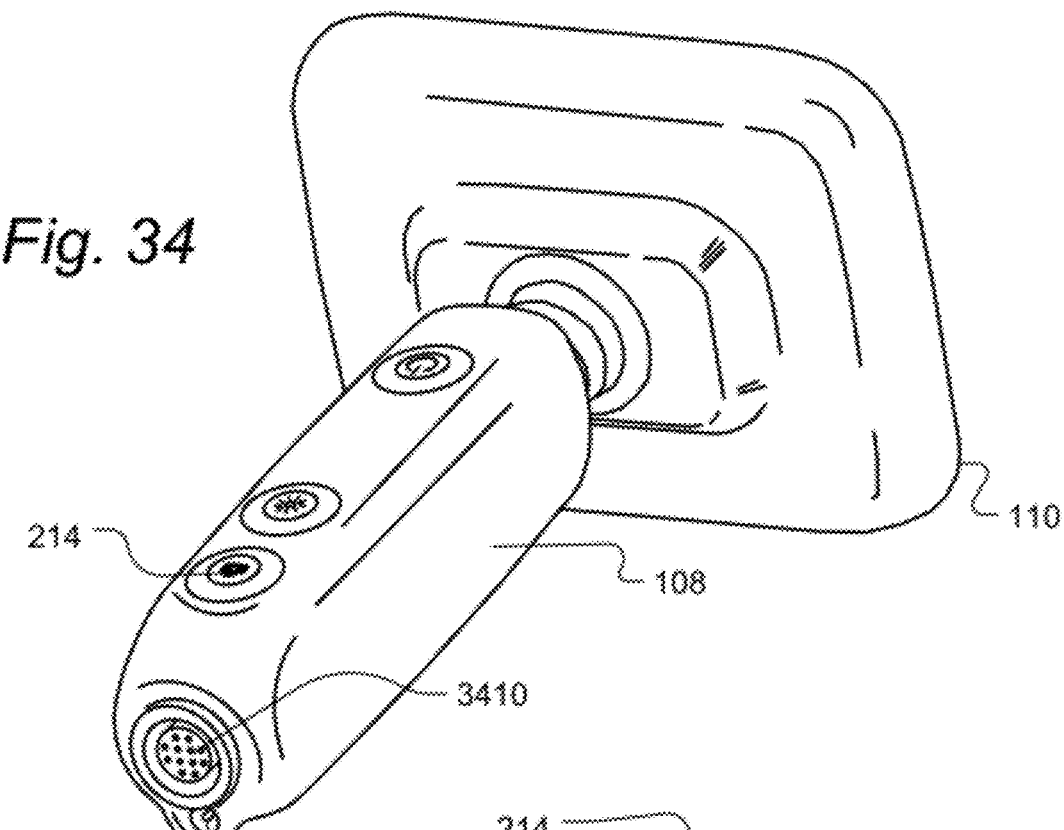
Figure 35:
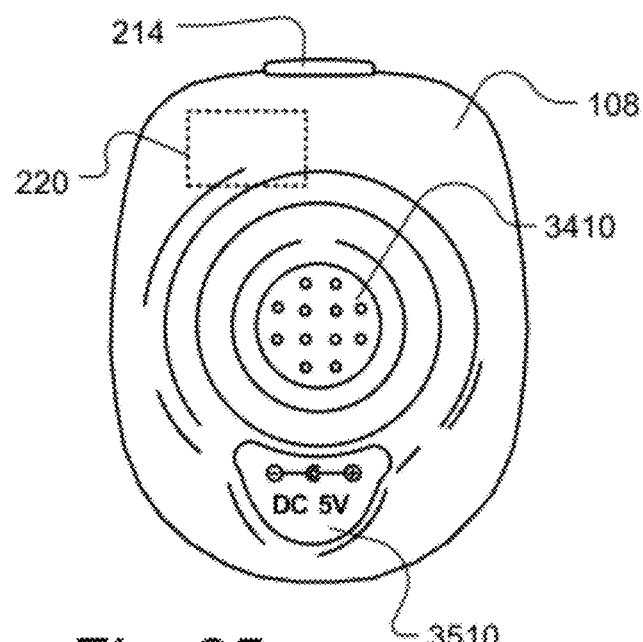

FIGS. 34-39 show a device for combined hysteroscopy and endometrial biopsy having a detachable handle, which can be mated with a docking station, according to some embodiments. FIGS. 34 and 35 show details of the handle and display detached from the fluid hub and cannula, according to some embodiments. FIG. 34 is a perspective view wherein handle 108 and display 110 are detached from the sliding connector 106 of the fluid hub 104 such as shown in FIG. 1. The distal end of the handle body 108 includes connector 3410 that has pin sockets that are used both for communicating and supplying power to the cannula when connected as well as to transmit video and control signals and settings to and from a base station or docking station when docked. The handle 108 also includes a recessed DC connector 3412 that is used to supplying power to the handle 108 when docked, for example to recharge the battery 220 and/or to prevent battery drain when downloading or viewing images and video and/or uploading settings to the unit. FIG. 35 is a distal end view of the handle 108, and shows the rubber flap 3510 that seals the DC power connector 3412 when not being used such as during docking with a docking station.

Figure 38:
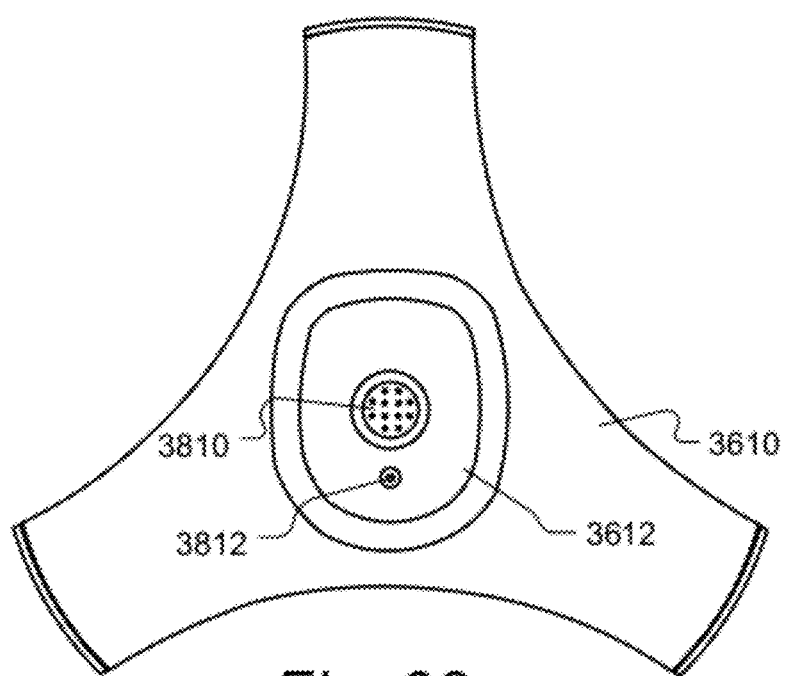
Figure 39:
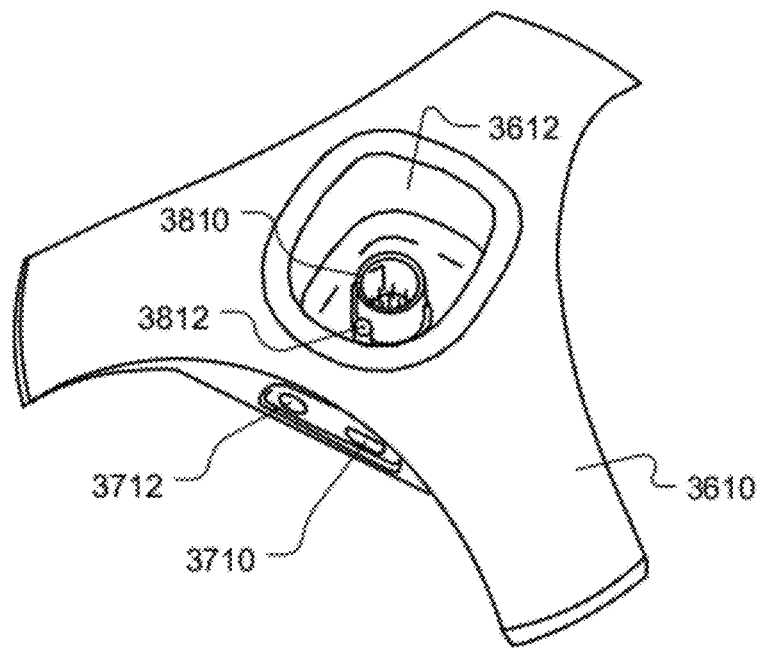

FIGS. 36 and 37 are a perspective view and a side view, respectively, of the handle and display docked to a base station, according to some embodiments. The handle 108 and display 110 are shown mated, or docked with base station 3610. The distal portion of the handle 108 is inserted into the opening, lined with a rubber liner 3612. When inserted in the base station 3610, the handle and display are well supported protected as shown. In addition to providing a stable base for the handle and display, the base station 3610 can also be used to supply power to handle and display, such as for recharging the battery and/or for viewing images and video on the display 110. For this purpose, an external power supply can be connected to the base station 3610 via the DC power connector 3712. The base station can also be used to communicate with the handle and display, such as to view and or download images or video, as well as to view and modify settings. The mini-USB connector 3710 can be used for this purpose, as well as to supply power to the base station (as well as to the handle and display when docked). According to some embodiments, the base station 3612 includes wireless communication circuitry, such as Wi-Fi, for communicating with devices such as a smart phone 3220, a tablet computer 3222 (as shown in FIG. 32), a mobile computer, or other mobile device having wireless and display capabilities are used to view the images and/or video. FIGS. 38 and 39 are a plan view and perspective view of the base station 3610 without the handle inserted. As can be seen a mating connector 3810 is provided which mates with the connector 3410 as shown in FIGS. 34 and 35. Also provided is a DC power connector 3812 that mates with the DC power connector 3412 as shown in FIG. 34. Additional storage and/or processing can be provided for still or video images from the device 100, such as storage in PACS or other archival storage systems of the type commonly used in hospitals and clinics for patient records and medical images and/or processing in work stations commonly used for processing and viewing of medical images in hospitals and clinics. The still and/or video images from the device 100 can be formatted as needed for a commonly used format, such as DICOM in one example, in the base station 3610, or one or more of the devices 3220 and 3222, or a mobile computer, or a computing device connected to the base station 3610. The formatted still and/or video images then can be transmitted in accordance with the selected format to a PACS or other storage system, and/or to a workstation where they can be further processed as is known in the art, e.g., to enhance certain aspects of images or to carry out CAD (computer aided detection) processes, and can be displayed alone or together with images from other modalities or prior images of the same patient for diagnostic or other purposes. According to some embodiments the base station as shown in FIGS. 36-39 are particularly useful when the cannula 102, fluid hub 104 and connector 106 are intended to be disposed of after a single-use, while the handle 108 and display 110 are designed to be re-used many times. In this case the handle and display are conveniently stored on the base station while a supply of single-use cannula/hub assemblies are kept in pre-sterilized packages ready for use.

Figure 40:
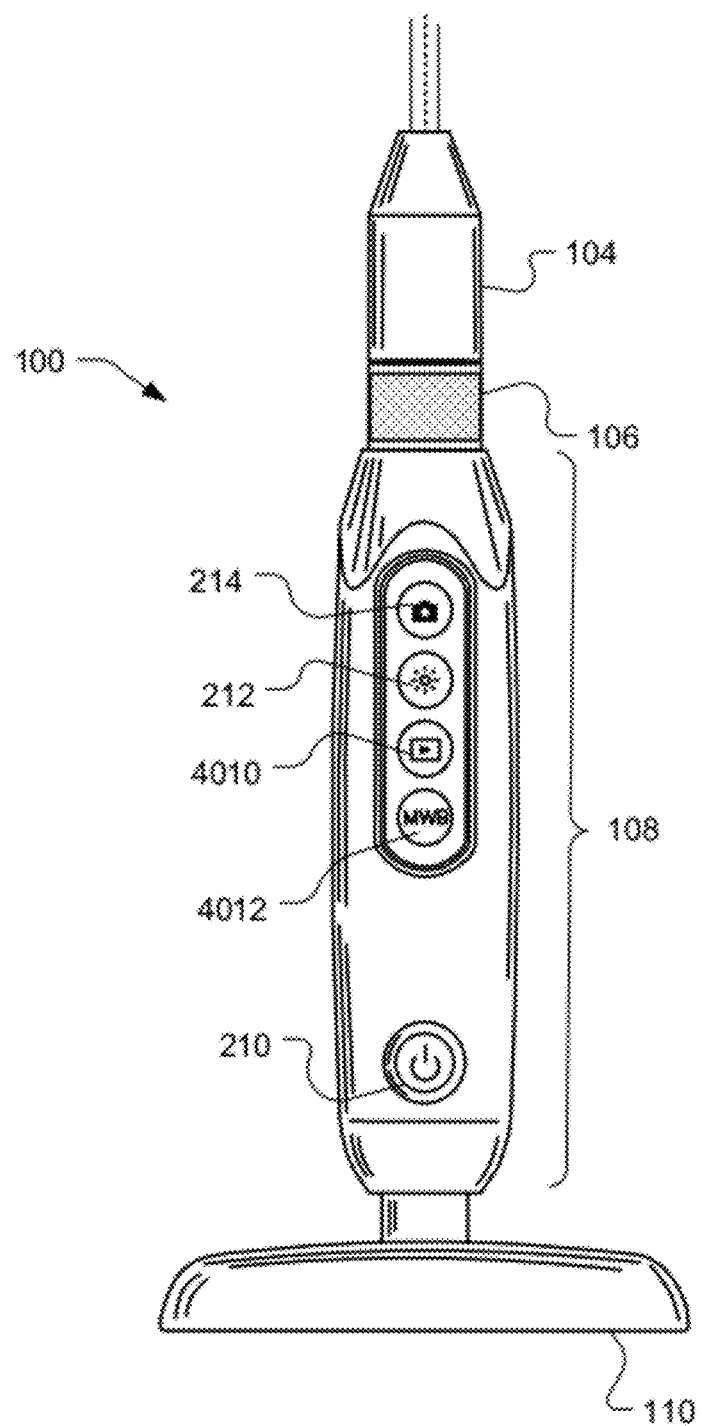
FIG. 40 is a top view of a device for combined hysteroscopy and endometrial biopsy having additional buttons on the handle, according to some embodiments.

FIG. 40 is a top view of a device for combined hysteroscopy and endometrial biopsy having additional buttons on the handle, according to some embodiments. As shown, in addition to the ON/OFF button 210, LED brightness control button 212, and Snap/Video button 214 as described in FIG. 2, the handle 108 includes a playback button 4010 and a manual white balance button 4012. The playback button 4010 is used to re-play snapshots and/or video taken during the procedure such that medical personnel can later review the images or video on the display 110. The manual white balance button 4012 is used to cycle through several pre-set white balance levels so that the user can quickly and easily select a suitable white balance for the particular case.

FIG. 41 shows a display screen user interface for a device for combined hysteroscopy and endometrial biopsy, according to some embodiments. The touch-screen display 110 of hysteroscopy device 100 is shown with home screen 4110. According to some embodiments, the display is 3.5 inches in size. The home screen 4110 includes four options that can be selected by a user by touching the screen. A battery status icon 4120 is shown in the upper left corner. The home screen 4110 includes four user-selectable menu options (or soft-buttons) that are labeled as shown: new patient, preview, playback and setup. According to some embodiments, pressing the power ON/OFF button 210 for 1 second or less is used as a "home button" on the device 100 such that the home screen 4110 is displayed.

Figure 42:
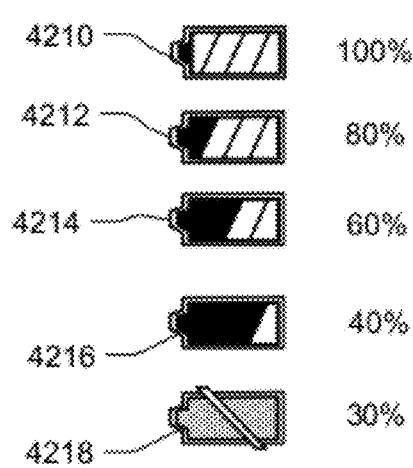
FIG. 42 shows details of some elements of a user interface for a hysteroscopy device, according to some embodiments.

FIG. 42 shows details of some elements of a user interface for a device for combined hysteroscopy and endometrial biopsy, according to some embodiments. Five levels of battery status can be displayed to the user in these examples on a display associated with the device, such as display 110. Icons 4210, 4212, 4214, 4216 and 4218 are used for 100%, 80%, 60%, 40% and 30% capacity remaining in rechargeable battery 220 respectively. According to some embodiments, a red color and/or flashing is used for the icon 4218 to further draw the attention of the user.

Figure 43:
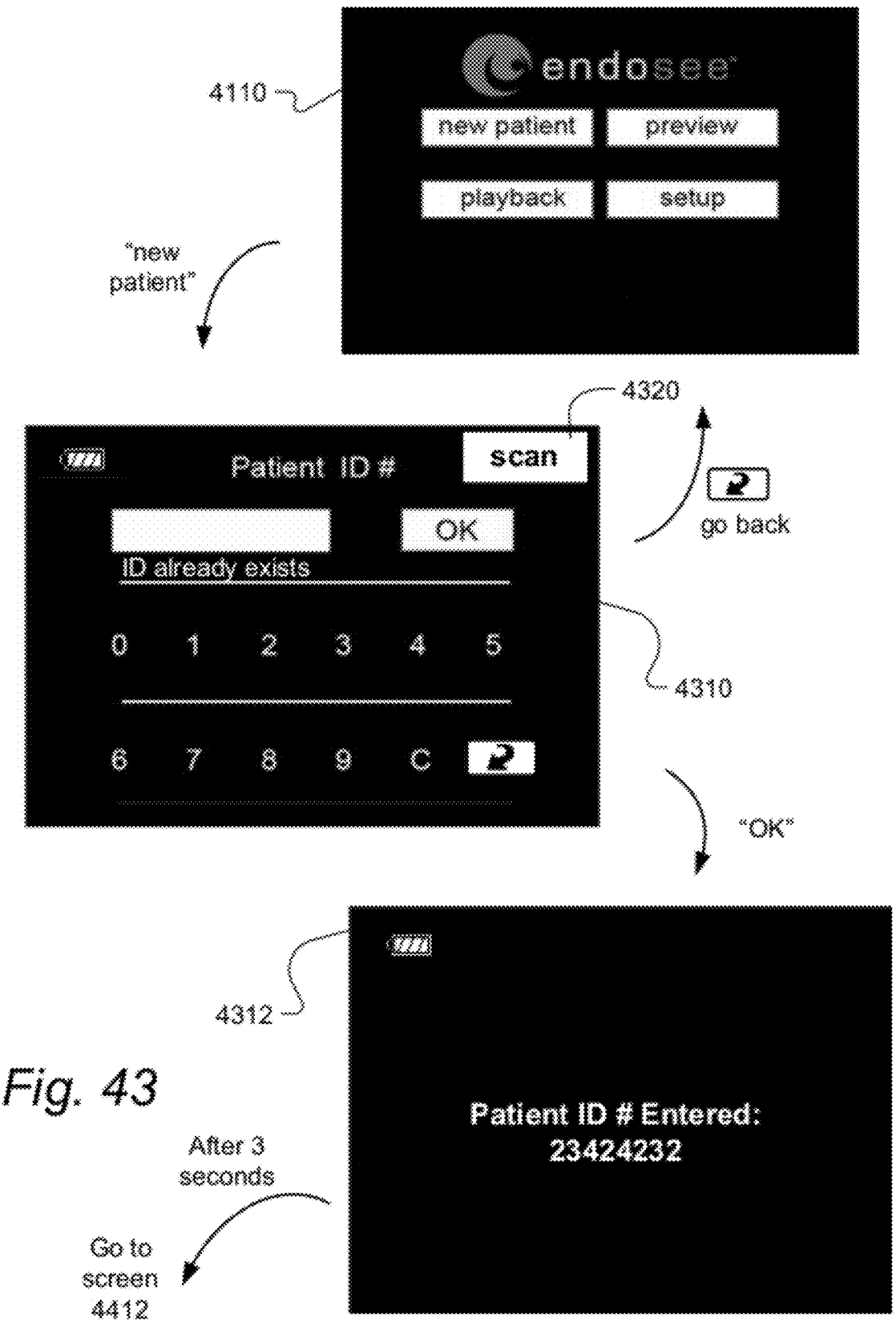
FIG. 43 is a flow chart showing aspects of a user interface for a hysteroscopy device relating to entering new patient information, according to some embodiments.

FIG. 43 is a flow chart showing aspects of a user interface for a device for combined hysteroscopy and endometrial biopsy relating to entering new patient information, according to some embodiments. From home screen 4110 on a display such as 110, when the user selects "new patient" screen 4310 is displayed, allowing the user to enter a new patient ID number. After entering the new number using the number buttons provided (e.g., a soft button), pressing "OK" confirms the user's entry. If the ID already exists, the message "ID already exists" is displayed prompting the user to enter a different number. A "go-back" button is also provided in the lower right corner, and in many other screens shown herein, that allows the user to return to the previous screen. According to some embodiments, the camera module on the distal tip of the device 100 can be used to enter patient information as a barcode scanner for barcodes and/or matrix barcodes such as a QR Code, which may already be on the patient's file or paperwork, to quickly and accurately enter a patient ID number. In this case a "scan" button 4320 is included on screen 4310. After successfully entering a new patient ID number, the confirmation screen 4312 is displayed for a fixed duration, for example 3 seconds, after which a transition is automatically made to the preview screen 4412 in FIG. 44 infra, such that live video from the camera module of device 100 is displayed.

Figure 44:
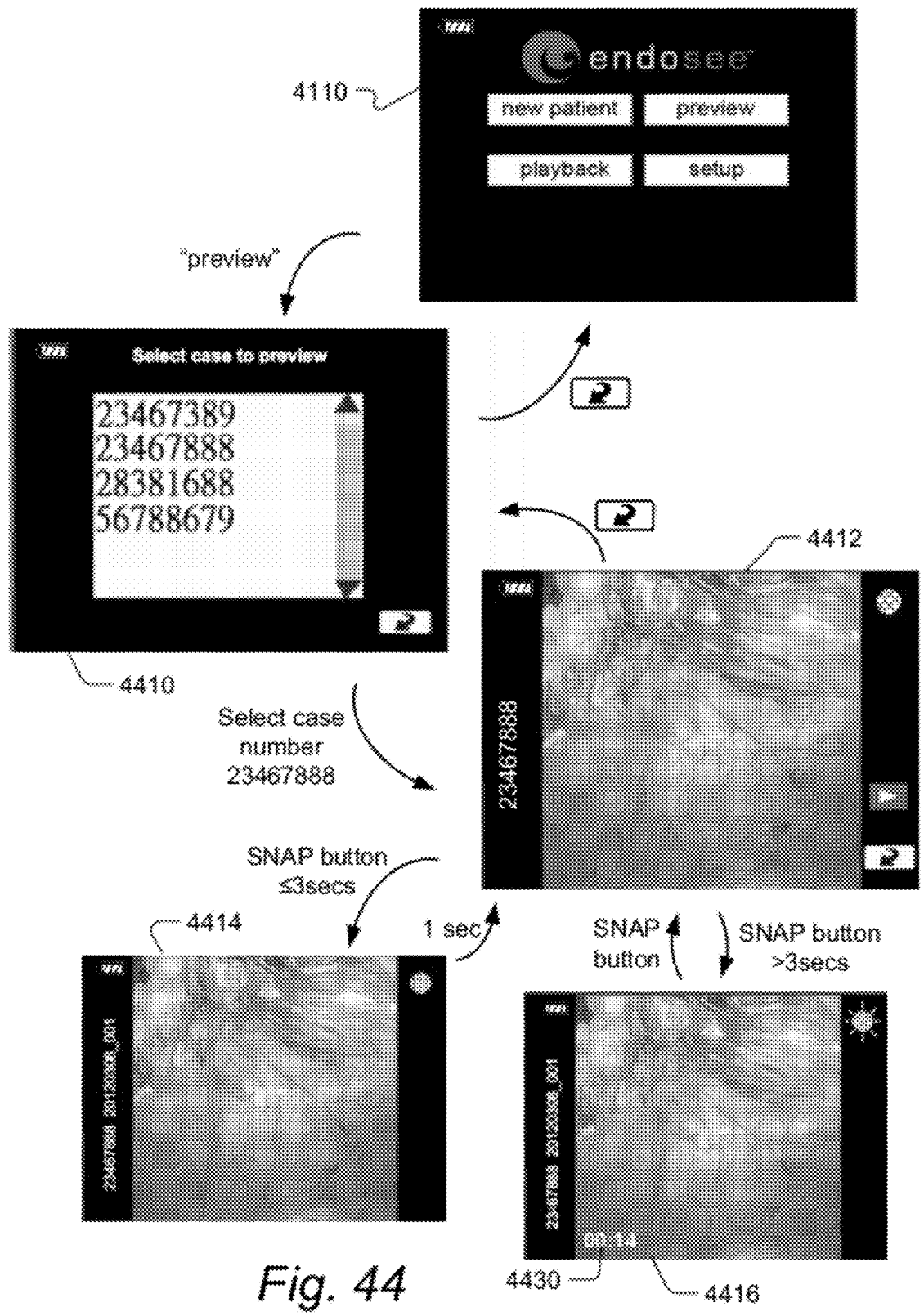
FIG. 44 is a flow chart showing aspects of a user interface for a hysteroscopy device relating to previewing images and video, according to some embodiments.

FIG. 44 is a flow chart showing aspects of a user interface for a device for combined hysteroscopy and endometrial biopsy relating to previewing images and video, according to some embodiments. From home screen 4110 on a display such as 110, when the user selects "preview" screen 4410 is displayed, allowing the user to select from among a list of cases, or patients, to use. Touching directly on one of the numbers highlights the number, such with yellow highlighting. Touching the up and down arrows on the scroll bar on the right side scrolls through the list (or scrolls the colored highlight field through the list). According to some embodiments touch and drag gestures such as is known with smartphone and tablet computer interfaces can be used for scrolling through lists of numbers or images. When a highlighted number is pressed again, then screen 4412 is displayed, in which live video from the distal mounted camera of device 100 is shown to the user. The live preview screen 4412 also includes the patient ID number on the left side as well as a green disk icon in the upper right corner to indicate to the user that live preview is being displayed. Pressing the go-back button returns to the previous screen. A playback button on the right side allows the user to re-play a predetermined length of video, such as 3-5 seconds. Pressing the snap button 214 for 3 seconds or less causes capture of a single photo, as shown in screen 4412. A solid red disk icon is displayed in the upper right corner. The single capture image is displayed for 1 second (or other fixed length of time) after which the live preview screen 4412 is returned to. Additionally, or in addition to displaying the image, an audible photo shutter sound can be played and/or a brief transition to white or black can be used to indicate to the user that a still image has been captured, according to some embodiments. If the snap button 214 is pressed for longer than 3 seconds, video is captured, as shown in screen 4416. In this case the video being captured is displayed while the red disk icon in the upper right corner blinks to indicate that video is being captured. Video capture begins and continues until the snap button is pressed again. According to some embodiments a timer 4430 can also be provided showing the length of video captured.

Figure 45A:
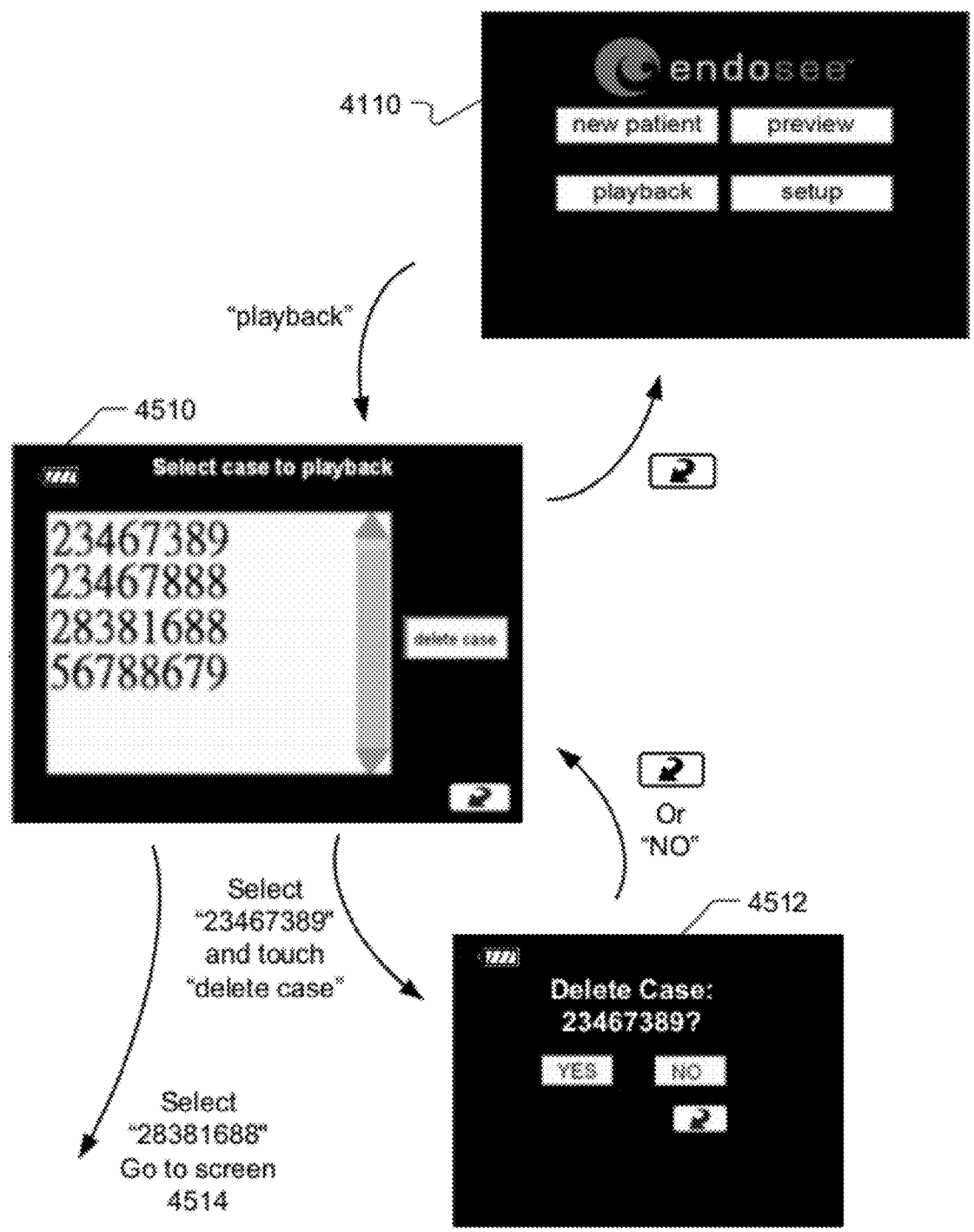
FIGS. 45A-45B are a flow chart showing aspects of a user interface for a hysteroscopy device relating to playback of saved images and video, according to some embodiments.
Figure 45B:
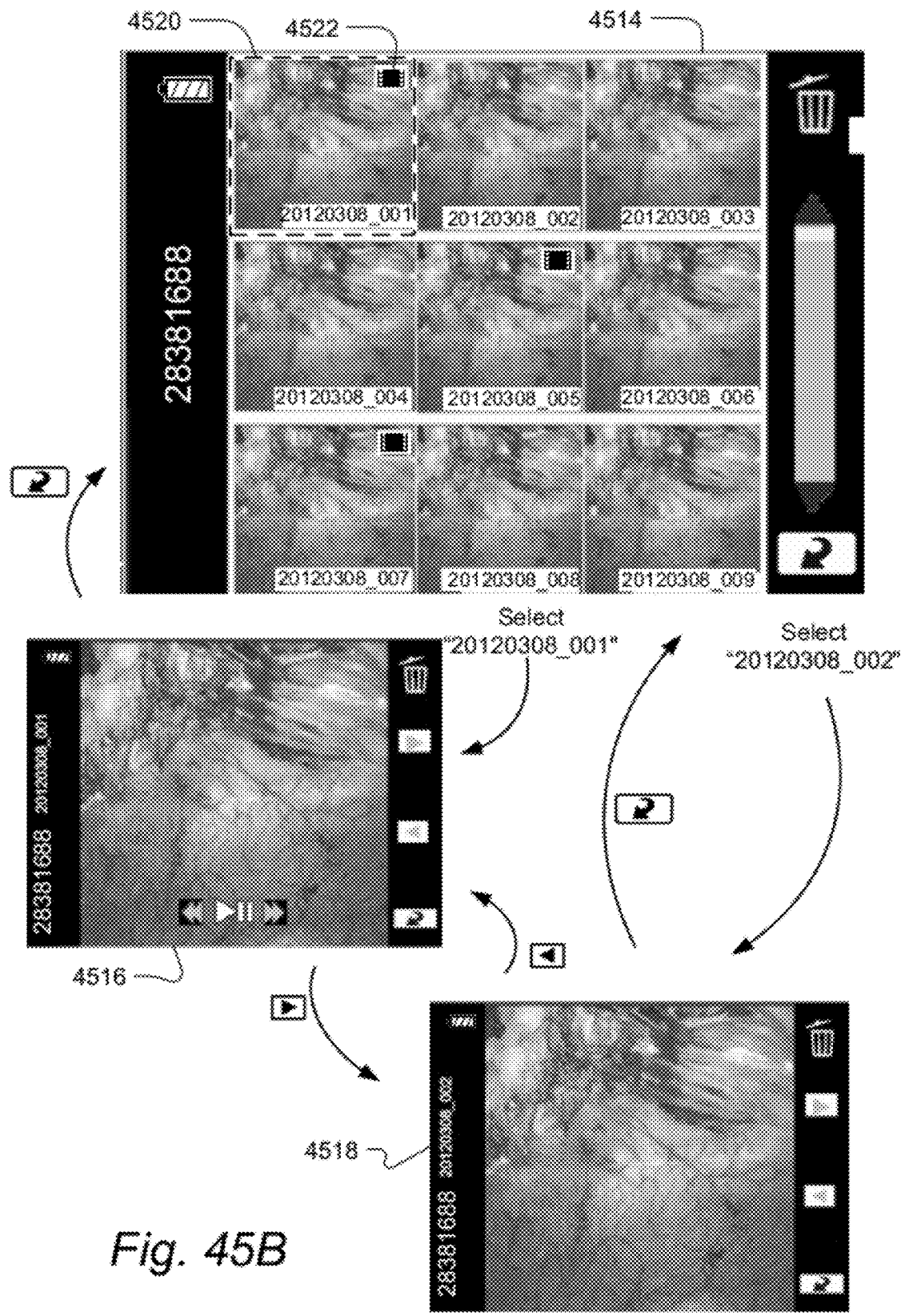

FIGS. 45A-45B are a flow chart showing aspects of a user interface for a device for combined hysteroscopy and endometrial biopsy relating to playback of saved images and video, according to some embodiments. In FIG. 45A, from home screen 4110 on a display such as 110, when the user selects "playback" screen 4510 is displayed, allowing the user to select from among a list of cases, or patients, to playback. As in screen 4410, yellow highlighting is used to first select a case. If the user selects "delete case" then the highlighted case will be deleted after a confirmation screen 4512. If a case is highlighted and then selected, screen 4514 in FIG. 45B is displayed. Screen 4514 includes thumbnail images of all of the captured still images and video, which can be scrolled through (using the scroll bar, or using a swipe gesture). A particular image or video is highlighted, such as will yellow, as indicated by the dashed line 4520. The thumbnail images include the file number, as well as a movie icon 4522 when the file is video rather than a still image. Screen 4514 also shows the patient ID on the left margin, as well as a delete icon and go back button on the right margin. The delete icon can be used to delete an individual highlighted file, after user confirmation. Selecting a highlighted video file, such as image "20120308_001" caused playback screen 4516 to be displayed. The user can control the video playback using the play/pause, rewind and fast forward buttons. The user can also move to the next or previous file using the arrow buttons in the right margin. Screen 4518 shows an example of displaying a still image.

Figure 46:
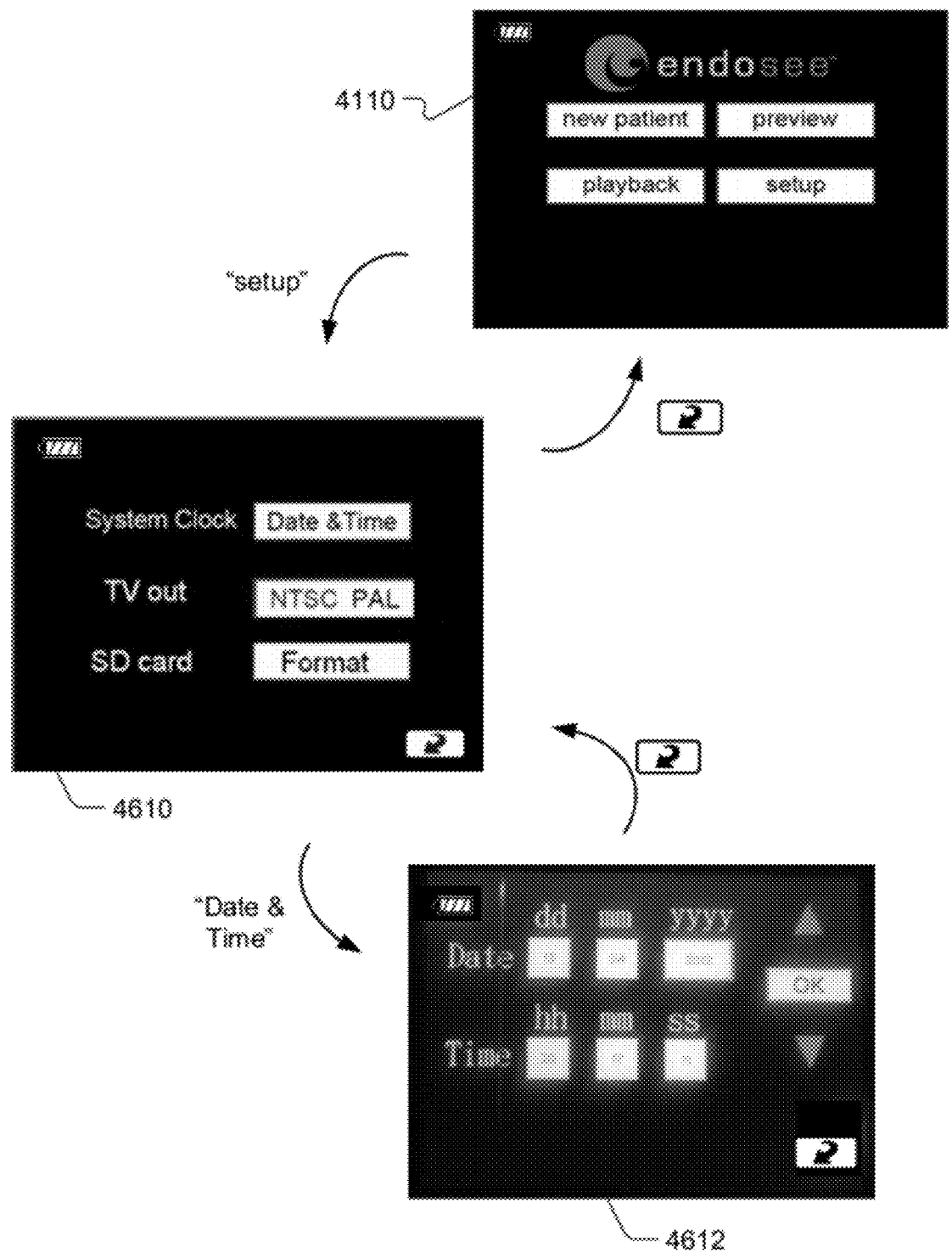
FIG. 46 is a flow chart showing aspects of a user interface for a hysteroscopy device relating to settings, according to some embodiments.

FIG. 46 is a flow chart showing aspects of a user interface for a device for combined hysteroscopy and endometrial biopsy relating to settings, according to some embodiments. From home screen 4110 on a display such as 110, when the user selects "setup" screen 4610 is displayed, allowing the user to view and modify various device settings. Examples of such settings are the system clock, which can be modified using the screen 4612, as well as the TV out format and formatting the internal flash memory card. According to some embodiments, many other settings can be programmed by the user using the interface shown.

FIGS. 47-48 are side views showing details of the shapes of distal tips of a device for combined hysteroscopy and endometrial biopsy, according to some embodiments. It has been found that the distal tip of the device preferably should be rounded for several reasons. First, the tip roundness greatly lowers the risk of accidental damage to the uterus, such as piercing or puncturing delicate uterine tissues during use. Secondly, the distal tip roundness affects the resistance of the distal tip to collecting matter that can clog the tip and blocking the view of the camera. It has been found that the edges of the tip should preferably be rounded by at least a radius of 0.25 mm. In the example shown in tip 120 of FIG. 47, the edges of the distal tip such as shown in region 4702 are rounded to a radius of 0.5 mm. Additionally, it has been found that there is benefit to the front face of the distal tip to be rounded as well. By making the front face 4710 convex the tip is much less likely to collect tissue debris or other matter that might occlude the field of view or make it more difficult to obtain clear images from the camera module. In the example of FIG. 47, the front face 4710 is preferably rounded to a radius of about 10 mm. In the example of FIG. 48, the distal tip 120 preferably has a substantially flat central portion 4810, surrounded by an outer region 4812 that is rounded to a radius of about 2.5 mm. The edge portion 4802 is rounded to a radius of about 0.44 mm. It has been found that making substantially flat the central portion 4810 (which is less than about 30% of the total frontal area in this example) can be useful in reducing distortion in the images captured by the camera module while the substantial curved portions 4812 and 4802 provide enough rounding to avoid tissue collection and reduce tissue damage risks. According to some embodiments, it has been found that the outer region making up at least 50% of the frontal area should be substantially rounded.

Figure 49:
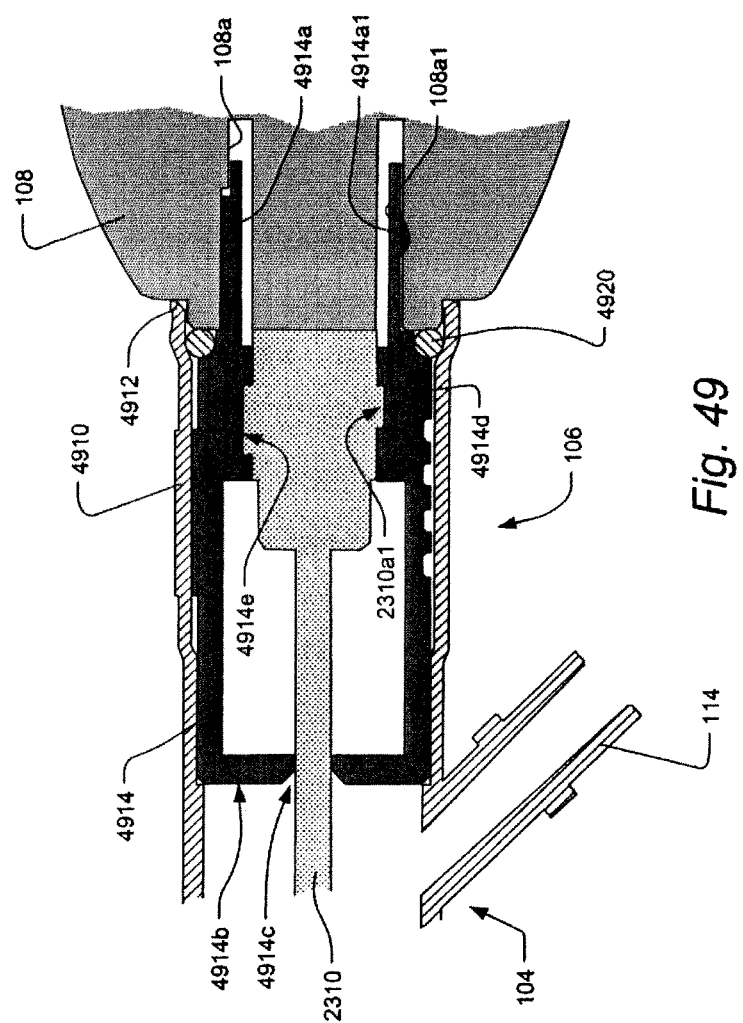
FIGS. 49-51 illustrate further details and embodiments.

FIG. 49 is a cross section showing details of a sealed sliding connector 106 for a device for combined hysteroscopy and endometrial biopsy, according to some embodiments. The sliding connector 106 is shown here with an outer shell 4910 that includes a lip 4912 that fits over an o-ring seal 4920 and a portion of the handle assembly 108 so as to provide a suitable seal between the fluid hub 104 and the handle assembly 108. Multiple similar seals can be provided along the length of connector 106 to further isolate handle 108 from patient matter when the cannula assembly of the device is disposable but handle 108 is reusable. An additional connector (not shown) can be inserted between connector 106 and handle 108 for further insulation, and can be made in a way to allow the additional connector to be sterilized before used for another patient (as it only has to provide an electrical connection between the cannula and the handle). Fluid hub 104 comprises a sealed sliding connector 106 that fits inside an outer shell 4910 of hub 104. Sliding connector 106 envelops a cable 2310 that that has an enlarged cross-section at its proximal end, from which cable 2310 extends distally to the camera module and the LEDs at distal tip 120 to carry video signals and control signals. Sealed sliding connector 106 comprises a barrier 4914 fitted tightly inside outer shell 4910. Barrier 4914 terminates at its proximal end in an extension 4914a that fits into a closed channel 108a in handle 108 such that an outwardly facing bump 4914a1 releasably fits into an inwardly facing depression 108a1 in channel 108a. Barrier 4914 further includes a distal portion that terminates in a first seal 4914b having an opening 4914c through which cable 2310 passes. An intermediate portion of barrier 4914 provides an additional seal by including an inner indentation 4914e tightly enveloping a radial projection 2310a1 of the proximal portion of cable 2310. Barrier 4914 further includes at its proximal portion a lip 4914d that helps form another additional seal by bearing against o-ring 4920 to further help ensure that fluid and tissue samples will not reach interior portions of handle 108 when the instrument is in use.

Figure 50:
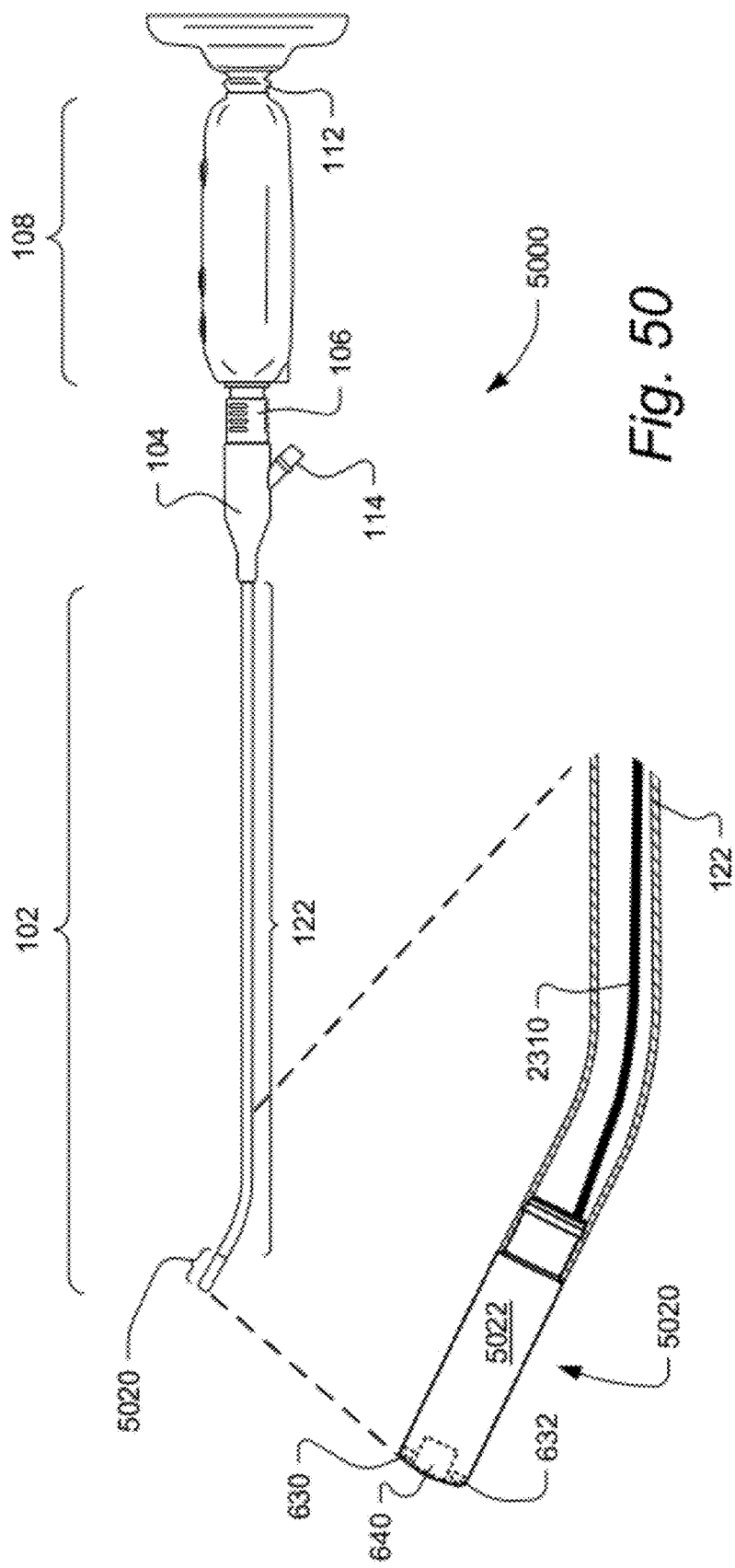

FIG. 50 shows a hysteroscope, according to some embodiments. The hysteroscope 5000 can be identical or similar to the device 100 described herein (including, for example, the user-interface described in FIGS. 41-46), except that it is intended only for hysteroscopy and not endometrial biopsy. As such the distal tip assembly 5020 does not have a side-facing sampling port and does not make use a separate fluid channel for sampling (as shown in FIGS. 8A-E and 9). However, a separate channel coupled to a side port or another forward facing port can be provided if desired to both deliver fluid to the uterus and withdraw fluid (and other matter) from the uterus, for example distend and relax the uterus or to flush the uterus. The assembly 5020 includes a tip body 5022, camera assembly 640 and LEDs 630 and 632. According to some embodiment, as with the device 100, the cannula 102 (including distal tip 5020), fluid hub 104 and sliding connector 106 are designed for a single-use, while the handle 108 and display 110 are designed to be re-used many times. Thus, the hysteroscope 5000 includes many of the same features and benefits from many of the same advantages as the combined hysteroscopy and biopsy device 100.

Figure 51:
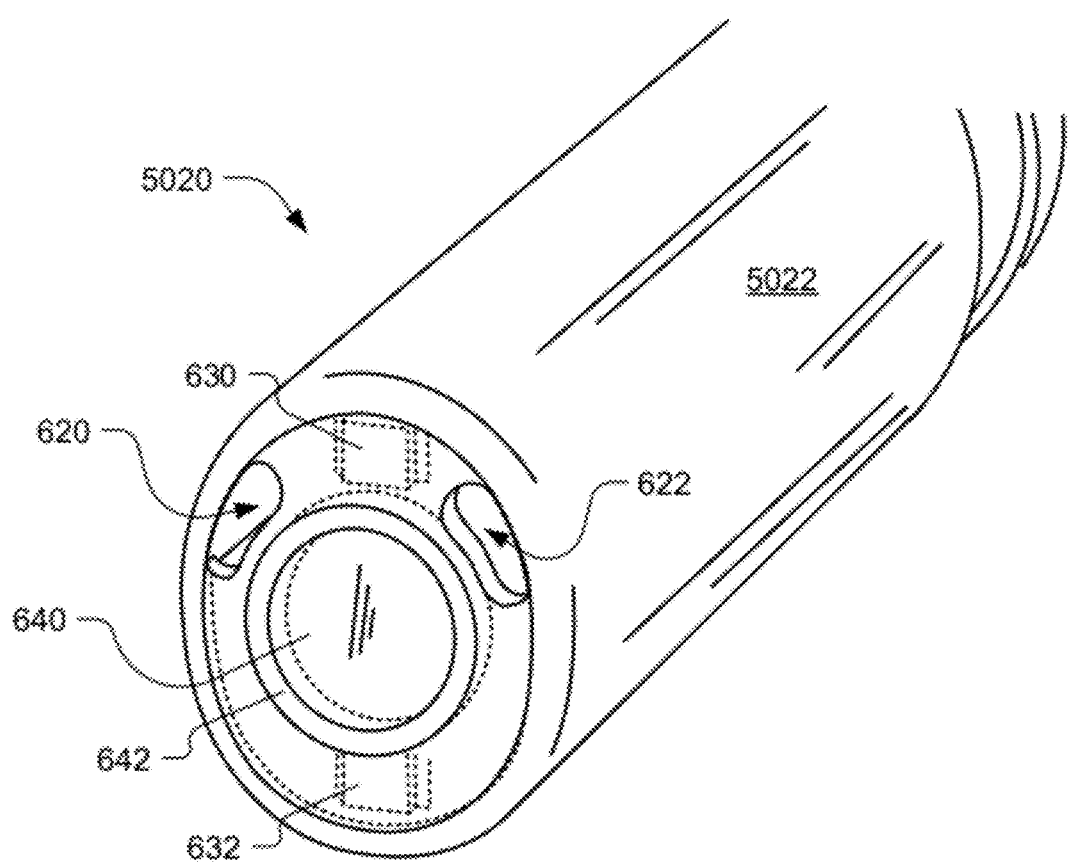

FIG. 51 shows details of a distal tip for a hysteroscope such as shown in FIG. 50. The distal tip assembly 5020 is shown with the tip body 5022 including two forward facing fluid ports 620 and 622, two LEDs 630 and 632, as well as camera assembly 640.

Figure 52:
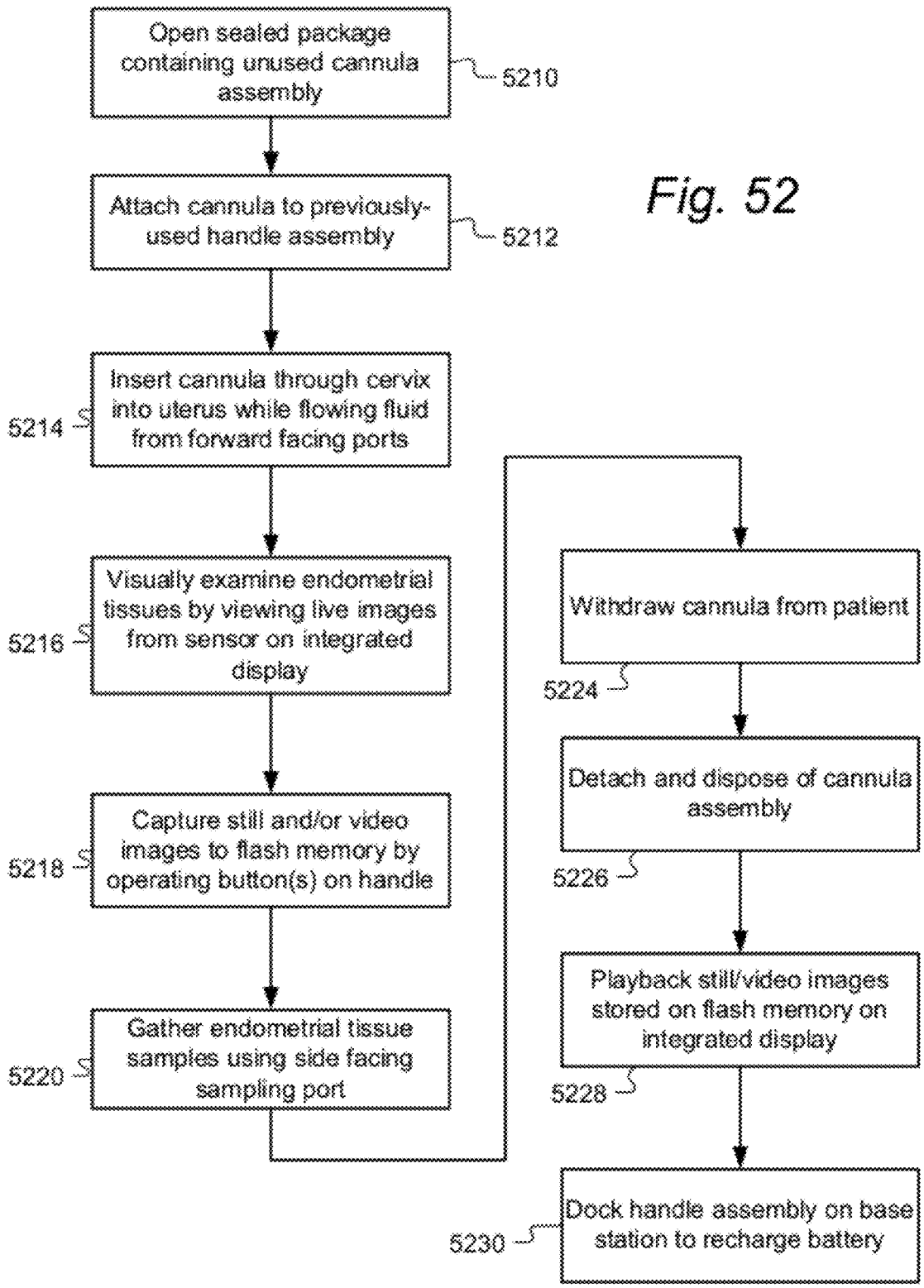
FIG. 52 is a flowchart illustrating examples of steps in using certain embodiments.

FIG. 52 is a flow chart illustrating an example use of a hysteroscopy device having the disposable cannula and re-usable handle and display, according to some embodiments. In step 5210, an unused cannula assembly, which for example includes cannula 102, fluid hub 104 and connector 106 as shown in FIG. 1 or in FIG. 50, is removed from a sterile package and in step 5212 the connector is attached to a previously used handle assembly, which for example includes a handle 108 and a display 110 as shown in FIG. 1 or in FIG. 50. Although the handle assembly has been previously used, it is cleaned and disinfected according to known standard practices, such as with rubbing alcohol or other disinfectant such as Cidex. Note that the example shown in FIG. 52 is for a previously used handle assembly, but the same steps would also apply to the case of a brand new handle assembly. In step 5214, the cannula is inserted through the cervix into the uterus, while flowing fluid from forward facing ports, such as ports 620 and 622 shown and described supra. Note that according to some embodiments, the sterile package is opened but not removed from the cannula assembly in step 5210. In this case the package is only opened the proximal end of the cannula, namely the end with the connector such that the connector can be attached to the handle. Then just prior to use, the remainder of the packaging is removed from the cannula. In step 5216 the user visually examines the endometrial tissue by viewing live images on the display 110. Lighting can be adjusted, for example using a control button on the handle. If the user wishes, still and/or video images can be captured using a control button on the handle. In step 5220, in the case where the device is for combined hysteroscopy and endometrial biopsy, tissues can be gathered using the side facing sampling port (such as port 610) without having to withdraw the cannula. In some cases steps 5216, 5218 and/or 5220 may be repeated as needed. Note that fluid induced distending and un-distending as described in some of the commonly assigned incorporated applications also is carried out to aid in examination and tissue collection, according to some embodiments. In step 5224 the cannula is withdrawn. In step 5226 the cannula assembly is disconnected, by detaching the connector from the handle, and the entire cannula assembly is disposed of. In step 5228 stored images are played back on the display, for example using a touch-screen interface as described supra. In step 5230 the handle assembly is docked to a base station for battery recharging and/or for transferring images and patient information out of the handle to other storage/processing facilities. According to some embodiments, a standard cleaning procedure is performed on the handle prior to docking on the base station. Note that the step 5228 of playing back the images can happen at any time after capturing in step 5218. For example, play back can be done before gathering samples, in step 5220, after withdrawal but prior to detaching the cannula in step 5226, or while the handle assembly is docked in the base station such that steps 5228 and 5230 are performed in parallel. In the case of viewing playback images while docked in a base station, tilting of display 110, as described with respect to FIG. 1, has been found to be useful in some situations.

Recent advances have enabled small, miniature and disposable endoscopes. Some embodiments disclosed herein innovatively combine a miniature endoscope with a modified endometrial sampling device in an integrated medical device. The integrated medical device combines a hysteroscope sheath with an endometrial sampling device, allowing the gynecologist or other healthcare provider to perform the dual function of hysteroscopy and endometrial sampling without the need of conventional cumbersome hysteroscope device such that hysteroscopy and the endometrial sampling may be done in a single procedure without the need for a separate medical device FIG. A1 illustrates a medical device combining an endoscope and endometrial sampling device, according to some embodiments. Medical device A100 includes a processor module A102, a sampling portion A104, a balloon A106 and imaging module A108. In some embodiments, the processor module A102 has a battery A110 or is otherwise connected to a power source, and further includes various video processing electronics A112 that control the operation of various components of the medical device A100.

The processor module a102 further includes a first connector A114 that is complementary to and configured to receive a second connector A116 on a proximal end A118 of a semi-rigid endoscope A120 included in the sampling portion A104. The first and second connectors A114, A116 provide a mechanical and electrical interface between the processor module A102 and the endoscope A120. According to some embodiments, the endoscope A120 is substantially cylindrical with an outer diameter of less than about 2.8 millimeters ("mm").

The imaging module A108 is attached to a distal end A122 of the endoscope A120. In some embodiments, the imaging module A108 may include at least one of each of a lens A108A, illumination device A108B and imaging device A108C (illustrated in FIG. A8, infra.). According to some embodiments, the imaging or photon-sensing device is positioned directly behind the lens and contained within the housing. The illumination device A108B may be a light emitting diode ("LED") or other suitable optical illumination delivered by optical fiber from light sources inside the endoscope A120 or processor module A102. That is, the illumination device A108B may be LEDs located at the distal end A126 or it may LEDs in the proximal end A118 or the processor module A102 whose light is transmitted to the distal end A126 of a sampling sheath A124 via optic media or fibers that are embedded in the walls of the sampling sheath A124 or embedded in the endoscope A120. The imaging device may be a complementary metal-oxide-semiconductor ("CMOS") image sensor, a charge-coupled device ("CCD"), or other suitable image sensor.

The sampling portion A104 further includes the sampling sheath A124. In the illustrated embodiment, the sampling sheath A124 has a substantially hollow cylindrical shape open on both ends for receiving the endoscope A120. An outer diameter of the sampling sheath A124 is less than about 4.6 mm in some embodiments and an inner diameter of the sampling sheath A124 is sufficiently large to accommodate the endoscope A120. The distal end A126 of the sampling sheath A124 and/or the distal end A122 of the endoscope A120 that contact tissue within the patient are smooth or blunt shaped in some embodiments and/or may be hydrophilically coated. Optionally, one or both of the endoscope A120 or sampling sheath A124 is a single-use device intended for use on a single patient during a single procedure, after which the endoscope A120 or sampling sheath A124 is intended to be discarded.

The balloon A106 is secured near a distal end A126 of the sampling sheath A124. Although not required in all embodiments, in the illustrated embodiment the sampling sheath A124 includes one or more holes A127 formed near its distal end A126 which can be used to obtain endometrial samples as explained in greater detail below.

The sampling sheath A124 includes a first fluid line A128 in communication with the balloon A106. A port A130 attached to the first fluid line A128 provides an interface for connecting the first fluid line A128 to a syringe or other suitable inflating/deflating device. In operation, the syringe is filled with a fluid that is forced into or out of the balloon A106 through the first fluid line A128 to inflate or deflate the balloon A106.

The sampling sheath A124 also includes a second fluid line A132 in communication with the hollow interior of the sampling sheath A124. The second fluid line A132 permits fluid such as a saline solution or other suitable fluid to be delivered, e.g., from a syringe A134, through the second fluid line A132 to the sampling sheath A124 and out of the distal end A126 of the sampling sheath A124 for distention or other purpose at the site of the procedure. A fluid stopper A136, such as a rubber nipple or O-ring, is positioned in a proximal end A138 of the sampling sheath A124. The fluid stopper A136 forms a seal around the endoscope A120 at the proximal end A138 of the sampling sheath A124 to prevent the fluid from exiting the sampling sheath A124 through the proximal end A138. It will be appreciated that the various fluid stoppers A136 described herein, which may include O-rings and duckbill valves as will be discussed in more detail to follow prevent fluid leakage. In addition, the fluid stoppers A136 prevent air intrusion during sample gathering. Excess air getting pulled in proximally may reduce the suction at the distal end of the medical device A100.

According to some embodiments, the medical device A100 permits a hysteroscope and endometrial sampling to be performed during a single procedure without removing the sampling sheath A124 and/or endoscope A120 from within the patient between the hysteroscope and endometrial sampling. According to these and other embodiments, and in operation, the endoscope A120 is inserted from the proximal end A138 of the sampling sheath A124 through the sampling sheath A124 to its distal end A126. According to some preferred embodiments, the endoscope A120 is pre-assembled with the sampling sheath A124 in one single piece. The fluid stopper A136 forms a seal around the endoscope A120 to prevent fluid from exiting through the proximal end A138 of the sampling sheath A124. A healthcare provider inserts the distal end A122/A126 of the medical device A100 through the vagina and cervix of a patient and into the patient's uterus. The term "healthcare provider" as used herein should be construed broadly and includes physicians, nurses, technicians and other users of the medical device A100.

The patient's uterus is distended by filling the uterus with fluid via the second fluid line A132 and sampling sheath A124. The balloon A106 is inflated via the first fluid line A128 to occlude the patient's cervix should leakage of fluid prevent adequate uterine distention.

The healthcare provider performs the hysteroscopy by operating and manipulating the medical device A100 to obtain images of the interior of the patient's uterus (and/or cervix and vagina) via, e.g., the imaging module A108. As indicated in FIG. A1, data representing the images thereby obtained is output to a video display (not shown in FIG. A1) separate from the medical device A100.

After performing the hysteroscopy, in some embodiments the endoscope A120 is removed from the sampling sheath A124 while the sampling sheath A124 remains in place within the patient. In other embodiments, the endoscope A120 need not be removed. The fluid stopper A136 at the proximal end A138 of the sampling sheath A124 is sealed. The syringe A134 is removed from the second fluid line A132 and suction is applied, e.g., via an empty syringe, to the second fluid line A132, to collect an endometrial sample via the sampling sheath A124. In more detail, suction applied to the second fluid line A132 creates suction at the distal end A126 and at the holes A127 of the sampling sheath A124. When the distal end A126 and/or holes A127 of the sampling sheath A124 are sufficiently close to the endometrium of the patient's uterus, the suction removes a sample of the endometrium. The sampling sheath A124 can then be removed from the patient.

FIG. A2 illustrates a medical device combining an endoscope, endometrial sampling device and integrated display, according to some embodiments. The medical device A100 of FIG. A2 is identical in many respects to the medical device A100 of FIG. A1 and reference can be made above for a description of the identical components. In contrast to the medical device A100 of FIG. A1, however, the medical device A100 of FIG. A2 includes an integrated display A140 attached to the processor module A102. The integrated display A140 is configured to receive data representing the images obtained during operation of the medical device A100 and to generate and display the images to the healthcare provider or other user of the medical device A100. Optionally, the data representing the images can additionally be output to an external display as indicated in FIG. A2. In some embodiments, the data representing the images can be output and displayed on both the integrated display A140 and an external display. In this way, the healthcare provider performing the procedure may view the displayed images at the same time that a person such as another healthcare provider or a family member of the patient may also view the images even if they are not close to where the procedure is taking place.

FIG. A3 illustrates additional aspects of a medical device combining an endoscope and endometrial sampling device, according to some embodiments. As previously described, the medical device A100 includes a processor module A102 and a sampling portion A104 that include the various elements previously discussed. In some embodiments, the processor module A102 is configured to be reusable while the sampling portion A104 is configured to be used only once. As will be appreciated, since most of the electronics involved with the medical device A100 are located in the processor module A102, the processor module A102 is the most expensive part of this example of the medical device A100. Accordingly, configuring the processor module A102 to be reusable advantageously saves on the cost of the medical device A100. It will be appreciated that the processor module A102 may include the integrated display A140, although this is not required.

As will also be appreciated that since the sampling portion A104 is inserted into the patient's uterus, it will generally not be sanitary to reuse in another procedure. However, since the sampling portion may be primarily made of relatively inexpensive plastics, it is generally economical to use a different sampling portion A104 for each patient.

In operation, the healthcare provider or other medical device 100 user may connect and disconnect the processor module 102 and the sampling portion 104 using connectors 114 and 116 as previously described when a hysteroscopy or other medical procedure is to be performed.

FIGS. A4A-A4B illustrate a medical device combining an endoscope and endometrial sampling device, according to some embodiments. Many of the elements of the embodiment shown in FIGS. A4A-A4B are the same as or similar to those discussed in the previously described embodiments, such elements will not be described or only briefly described. It will also be appreciated that the aspects of the embodiments previously described may also apply to the present embodiment. For example, although FIG. A4A does not show the balloon A106, the fluid line A128, and the port A130, it will be understood that these elements may be included in the embodiment of FIG. A4A if desired.

As illustrated, the present embodiment includes a processor module A102 that includes the battery A100 and the endoscope electronics A112. The processor module A102 may also include the connector A114 for connecting to the sampling portion A104. In this embodiment, the processor module A102 may be about 4 inches long and have an inner diameter of about ¾ inches. Of course, other dimensions for the processor module A102 are also contemplated. The processor module A102 may also include an integrated display A140, although this is not required. In the present embodiment, the integrated display A140 may be an LCD display with a thickness of about ½ inch or less and a diagonal dimension of less than about 4 inches. It will be appreciated that other dimensions are also contemplated for the integrated display A140.

As also illustrated, the medical device A100 of the present embodiment includes the sampling portion A104 including the endoscope A120 and the sampling sheath A124. In this embodiment, the sampling sheath A124 may have a length of around 6½ inches, an outer diameter of less than about 4.6 mm, and an inner diameter of greater than about 3.4 mm. As with the above embodiments, the inner dimension is sufficiently large to accommodate the endoscope A120. Of course, other dimensions may also be used. As also illustrated, in this embodiment the sampling sheath A124 has an angle or curvature A129 at the distal end A126, which in turn causes the endoscope A120 to also be slightly curved at the distal end A122. In the present embodiment, the angle or curvature A129 is greater than about 15 degrees, although other angles or curvatures are also contemplated. Having the sampling sheath A124 angled or curved at the distal end along with the sampling sheath being only moderately stiff allows for easier insertion into the uterus of the patient.

As illustrated, the medical device A100 includes one or more ports A127 for endometrial sampling. Referring to FIG. A4B, an example embodiment of the ports A127 is shown. In FIG. A4B, two ports A127A and A127B are included for endometrial sampling. As shown, these ports are near the distal end A126 and are included in the angled portion A129 of the sampling sheath A124.

Returning again to FIG. A4A, the medical device A100 includes a fluid and connector hub A105. As shown, the fluid and connector hub A105 includes the connector A116 that connects the sampling portion A104 to the processor module A102. In addition, the fluid and connector hub A105 includes a connector or opening A103 that connects the fluid line A132 to the sampling portion A104. Further, the fluid and connector hub A105 includes a connector or opening A106 for connecting the sampling sheath A124 to the fluid and connector hub A105, includes the fluid stoppers A136, and fluid flow channels or chambers. Specific embodiments of the fluid and connector hub A105 will now be explained.

FIGS. A5A-A5C illustrate portions of a fluid and connector hub A105 for use in a medical device combining an endoscope and endometrial sampling device, according to some embodiments. The one piece embodiment A200 of the fluid and connector hub A105 may be a single molded piece of plastic or metal, although any reasonable material and production method may be used to create the one piece embodiment A200.

As illustrated in FIG. A5A, which shows an exterior view of the one piece embodiment A200, the one piece embodiment A200 includes the connector A116 that connects the sampling portion A104 to the processor module A102. In embodiment A200, the connector A116 includes retention features A201 that act to align the connector A116 when connecting with matching features on the connector A114 of the processor module A102. In addition, the connector A116 includes an electric plug A202 for connecting with the endoscope electronics A112 of the processor module A102. The electric plug A202 allows for electric and/or optic signals to be sent from the endoscope electronics A112 to the imaging module A108 in the distal end of the endoscope A120.

FIG. A5B shows various pieces of the medical device A100 that are either included in the one piece embodiment A200 or that attach to the one piece embodiment A200. For example, FIG. A5B shows that a fluid stopper A136, which in this embodiment is an O-ring, although other fluid stoppers may be used, is inserted into the one piece embodiment A200. Further, a cylindrical connector piece A213 is used to connect the one piece embodiment A200 at connection A106 with the sampling sheath A124. Finally, the fluid line A132 includes a connector A211 that connects with a connector piece A212 for connecting the fluid line A132 to the one piece embodiment at the connector A103. It will be appreciated that the pieces A211, A212, and A213 may be made of a plastic or metal and may be molded or machined in any reasonable manner.

FIG. A5C shows an interior view of the one piece embodiment A200. As shown, the one piece embodiment includes a hollow cylindrical chamber that is large enough to hold the endoscope A120 and the sampling sheath A124. As shown, the endoscope A120, may be inserted into connector opening 106 and may connect with the electric connector A202. In some embodiments, the electrical connector 202 may be part of the endoscope A120.

The sampling sheath A124 may also be connected to the one piece embodiment A200 by the connector A213. Further, as shown, the fluid stopper A136 may be inserted to prevent fluid from reaching the processor module A102 when the module is connected to the one piece embodiment A200. As further shown, the connector A212 is inserted into the connector or opening A103 to connect the fluid line A132 to the one piece embodiment A200.

FIGS. A6A-A6B illustrates portions of a fluid and connector hub for use in a medical device combining an endoscope and endometrial sampling device, according to some other embodiments. In particular, FIGS. A6A and A6B illustrate a two piece embodiment A300 of the fluid and connector hub A105. The two piece embodiment A300 of the fluid and connector hub A105 includes a first piece A301 that connects to a second piece A302. The first and second pieces A301 and A302 may both be a single molded piece of plastic or metal, although any reasonable material and production method may be used to create the first and second pieces A301 and A302. Please note that some of the elements shown in FIGS. A6A and A6B have previously been described in relation to other embodiments disclosed herein and may not be described for the present embodiment.

As shown in FIGS. A6A and A6B, the first piece A301 and the second piece A302 are connected together to form the two piece fluid and connector hub A300. The pieces A301 and A302 may be attached with any reasonable attaching means such as, but not limited to, an epoxy or glue. In one embodiment, the first piece A301 and the second piece A302 are attached to one another during an assembly process that is done prior to the two piece fluid and connector hub A300 being shipped to the healthcare provider or other user of medical device A100. In other embodiments, the first piece A301 and the second piece A302 may be attached together by the healthcare provider or other user of medical device A100.

As shown in the figures, first piece A301 includes a first chamber A311, a second chamber A312 and a third intervening chamber A313. The first chamber A311 has a larger diameter than the other two chambers. Inside this chamber A311 is placed a duckbill valve A310. The duckbill valve A310 provides fluid stoppage while allowing the endoscope A120 to pass through and may therefore be considered a fluid stopper. In those embodiments where the first piece A301 and the second piece A302 are attached to one another during an assembly process that is done prior to the two piece fluid and connector hub A300 being shipped, the duckbill valve is placed in chamber A311 during the assembly process. The chamber A312 typically has a larger diameter than the chamber A313 and has a counter bore that helps trap the imaging module A108 distally but allows the imaging module A108 to be removed from the sampling sheath A124 proximally.

The second piece A302 includes a chamber A315 that connects with the chamber A311 upon assembly of the two pieces. The chamber A315 (as well as the chambers A311, A312, and A313) has at least a diameter large enough to hold the endoscope A120 and the sampling sheath A124. As shown, the sampling sheath A124 connects with the second piece A302 at the connection or opening A106. As with the one piece embodiment A200, a cylindrical piece A213 is inserted into the chamber A315 to help connect the sampling sheath A124 with the second piece A302.

Since the chamber A315 includes the fluid path from the fluid line A132, a fluid stopper A136, which in the present embodiment may be an O-ring, is placed in the chamber A315 to prevent liquid from reaching the endoscope electronics A112. As with the one piece embodiment A200, the connector A212 is used to connect the second piece A302 with the fluid line A132 at the connector or opening A103.

FIGS. A7A-A7C illustrate portions of a fluid and connector hub for use in a medical device combining an endoscope and endometrial sampling device, according to some other embodiments. In particular, FIGS. A7A-A7C illustrate a three piece embodiment A400 of the fluid and connector hub A105. The three piece embodiment A400 of the fluid and connector hub A105 includes a first piece A401 that connects to a second piece A402. The second piece A402 in turn connects to a third piece A403. The first, second and third pieces A401, A402, and A403 may be single molded pieces of plastic or metal, although any reasonable material and production method may be used to create the first, second and third pieces A401, A402, and A403. The three piece embodiment A400 allows the imaging module A108 to remain in the sampling sheath A124 for the entire medical procedure. In other words, there is no need to remove the imaging module A108 when the endometrial samples are collected. Of course, the imaging module A108 can be removed during the procedure if more space is needed for fluid flow. Please note that some of the elements shown in FIGS. A7A-A7C have previously been described in relation to other embodiments disclosed herein and may not be described for the present embodiment.

As shown, the first piece A401 includes a Touhy Borst seal A420 as part of the connector A116. The Touhy Borst seal A420 is used to attach the fluid and connector hub A400 with the processor module A102 when in use and provides both fluid and air sealing and helps to fix the position of the optics module A108 in the distal end. As further shown, the first piece A401 includes a chamber A421 that includes a threaded end A422. The chamber A421 will typically be large enough to hold the endoscope A120 and/or any electrical or optical connection between the imaging module A108 and the processor hub A102.

The second piece A402 includes a chamber A411 that is sized to receive the threaded end A422 of the first piece A401. The chamber A411 includes grooves A413 that mate with threaded end A422 to connect the first and second pieces A401 and A402 together. In some embodiments, an additional adhesive such as an epoxy or glue may also be used to help connect the first and second pieces A401 and A402 together.

Inside the chamber A411 is placed a duckbill valve A410. The duckbill valve A410 provides fluid stoppage while allowing the endoscope A120 to pass through. In those embodiments where the first piece A401 and the second piece A402 are attached to one another during an assembly process that is done prior to the three piece fluid and connector hub A400 being shipped, the duckbill valve is placed in chamber A411 during the assembly process.

The third piece A403 includes a chamber A426 that receives an end A412 of the second piece A402 when the pieces A402 and A403 are connected during the assembly process. The chamber A426 will be large enough to receive the end A412. The second and third pieces may be secured using an epoxy, a glue, or any other reasonable means.

The third piece A403 also includes a chamber A425 that has at least a diameter large enough to hold the endoscope A120 and the sampling sheath A124. As shown, the sampling sheath connects with the third piece A403 at the connection or opening A106. In some embodiments, the cylindrical piece A213 (not shown) is inserted into the chamber A425 to help connect the sampling sheath A124 with the third piece A403. Since the chamber A425 includes the fluid path from the fluid line A132, the connector A212 is used to connect the third piece A403 with the fluid line A132 at the connector or opening A103.

FIG. A8 illustrates portions near the distal end of a medical device combining an endoscope and endometrial sampling device, according to some embodiments. Note that the embodiment shown in FIG. A8 may be practiced in the embodiments of medical device A100 previously described, therefore the elements previously described may not be described in relation to the present embodiment. FIG. A8 shows a close-up view of the distal end A126 of the sampling sheath A124. As previously described, the distal end A26 includes the imaging module A108, which may include a lens set A108A, illumination device A108B and imaging device A108C.

As will be appreciated, during a medical procedure, the lens A108A may become dirty due to body fluids and the like. In addition, the illumination device A108B, which may be one or more LEDs, may become hot during use. Accordingly, the embodiment of FIG. A8 includes a curved protrusion A810 that is created on one side of the sampling sheath A106 at the distal end opening A126. During use of the medical device A100, the curved protrusion A810 forces at least some the saline fluid or other suitable fluid from the fluid line A132 to wash over the lens A108A and/or the illumination device A108B. In this way, the saline fluid or other suitable fluid is able to wash the surface of the lens A108A. In addition, the fluid is able to cool the illumination device A108B in case it gets overheated.

The curved protrusion A810 may be created during the manufacturing process of the sampling sheath A124 and may be created using plastic molding techniques, although other techniques may also be used. As will be appreciated, the curved protrusion A810 will typically be large enough and curved enough to force the saline fluid to wash over the lens the A108A and/or the illumination device A108B while not blocking the field of view by lens A108A and illumination A108B.

FIG. A9 illustrates a medical device combining an endoscope and endometrial sampling device, according to an additional embodiment. The embodiment shown in FIG. A9 may be practiced in the embodiments of medical device A100 previously described. The embodiment of FIG. A9 shows that the fluid line A132 is connected to a second fluid line A133. The fluid lines A132 and A133 may be connected to the medical device A100 at the fluid and connector hub A105 or may be connected to the sampling sheath A124 as shown in FIG. A1. In some embodiments, the fluid lines A132 and A133 connect with the fluid and connector hub A105 at different opening of the fluid and connector hub A105. The fluid line A132 may be connected to the distal end opening A126 and the one or more side sampling holes A127 while the fluid line A133 may be connected to the one or more side sampling holes A127.

During a medical procedure, the saline solution or other suitable solution may be injected into the fluid line A132 by the syringe A134. A valve or clamp A910 may be placed in or over the portion of the fluid line A133 that connects with the fluid line A132 to prevent any in-flow of the saline solution to the fluid line A133.

During the out-flow process, when suction is applied to the tube A132 to collect endometrial samples as previously described, the valve or clap A910 may be opened or removed to allow out-flow from both the fluid line A132 and the fluid line A133. In this way, a greater amount of endometrial samples may be collected. It will be appreciated that separate syringes A134 may be used for the in-flow and out-flow process or the same syringe A134 may be used for both.

FIG. A10 illustrates a medical device combining an endoscope and endometrial sampling device, according to an additional embodiment. The embodiment shown in FIG. A10 may be practiced in the embodiments of medical device A100 previously described. As shown, the medical device in this embodiment includes the fluid line A132 and a second fluid line A133. The fluid lines A132 and A133 may be connected to the medical device A100 at the fluid and connector hub A105 or may be connected to the sampling sheath A124 as shown in FIG. A1. In some embodiments, the fluid lines A132 and A133 connect with the fluid and connector hub A105 at different opening of the fluid and connector hub A105. The fluid line A132 may be connected to the distal end opening A126 while the fluid line A133 is connected to the one or more side sampling holes A127.

During a medical procedure, the saline solution or other suitable solution may be injected into the fluid line A132 by the syringe A134 to create an in-flow. Suction may then be applied to the tube A133 by a syringe A134 to collect endometrial samples as previously described. In this way, a flow through process is created that may result in collected continuous flow of fluid through the uteral cavity. It will be appreciated that the same syringe may be used for both fluid lines 132 and 133 if circumstances warrant. A fluid bag that hanged over the patient may also be used for fluid inflow.

As previously described in the various embodiments disclosed, the medical device A100 may include the sampling portion A104 that includes the sampling sheath A124, the fluid and connector hub A105, and the optics module A108. As previously discussed, these separate parts may be connected in the various manner previously described. However, according to some embodiments the sampling portion A104, the fluid and connector hub A105, and the optics module A108 may all be integrated as a single piece at manufacturing time. This may remove the need for the various O-rings, duckbill valves, and Touhy Borst connections previously described. Thus, according to these embodiments, there is just one electro/mechanical connection with the processor module A102 and one single fluid channel and connector to the syringe A134. Advantageously, this embodiment provides for a minimum of attaching and detaching parts during a medical procedure and reduces manufacturing costs.

FIG. A11 is a flow chart showing a method of operating a device having a combined endoscope and endometrial sampling device, according to some embodiments. The method A1100 begins at step A1105 after the patient is suitably positioned for the procedure, e.g., the patient may be situated on an exam room table.

At step A1110, a sterile package including the endoscope A120 and/or a sterile package including the sampling sheath A124 are opened. Alternately, the endoscope A120 and sampling sheath A124 are both included in a single package that is opened at step A1110. In some embodiments, at step A1110 the endoscope A120 may be inserted into the sampling sheath A124, while in other embodiments the endoscope A120 is inserted into the sampling sheath A124 prior to being placed in the single sterile package.

At step A1115, the endoscope A120 is connected to the processor module A102. At step A1120, the processor module A102 is turned on and a manual white balancing procedure is undertaken. At step A1125, the second fluid line A132 is connected to the syringe A134 or other supply of saline or other suitable fluid.

At step A1130, the patient's cervix is disinfected, local anesthetic is optionally applied, and the distal end A122/A126 of the medical device A100 is inserted through the patient's vagina and cervix and into the patient's uterus. During step A1130, the imaging module A108 may be relaying images to the processor module A102 for display on the integrated display A140 and/or an external display to provide direct vision during insertion. Further, saline or other fluid is infused during step A1130 via the second fluid line A132 and sampling sheath A124 to distend the patient's uterus.

In those embodiments that include the balloon A106, at step A1135, after the distal end A122/A126 of the medical device A100 has been received within the patient's uterine cavity, the balloon A106 is inflated via first fluid line A128 to occlude the patient's cervix should leakage of fluid prevent adequate uterine distention. As shown by the dashed line, in those embodiments that do not include the balloon A106, step A1135 is skipped.

At step A1140, the patient's uterine/endometrial cavity is inspected using the endoscope A120. At step A1145, the endoscope A120 is removed while the sampling sheath A124 remains within the patient. In those embodiments that include the balloon A106, the balloon A106 is also deflated during step A1145.

At step A1150, the fluid stopper A136 at the proximal end A138 of the sampling sheath A124 is occluded and suction is created at the distal end A126 and/or at the holes A127 of the sampling sheath A124 by applying suction on the second fluid line A132 using, e.g., an empty syringe. Alternately, the second fluid line A132 is occluded and suction is applied at the proximal end A138 of the sampling sheath A124 to create suction at the distal end A126 and/or holes A127 of the sampling sheath A124.

At step A1155, the sampling sheath A124 is moved in and out while being rotated and while the suction is applied to the second fluid line A132 to obtain an endometrial sample.

At step A1160, the sampling sheath A124 is withdrawn from the patient and the endometrial sample is collected. The procedure is completed at step A1165.

FIG. A12 is a flow chart showing a method of operating a device having a combined endoscope and endometrial sampling device, according to some embodiments. The method A1200 begins at step A1205 after the patient is suitably positioned for the procedure, e.g., the patient may be situated on an exam room table.

At step A1210, a sterile package including the endoscope A120 and/or a sterile package including the sampling sheath A124 are opened. Alternately, the endoscope A120 and sampling sheath A124 are both included in a single sterile package that is opened at step A1210. In some embodiments, at step A1210 the endoscope A120 may be inserted into the sampling sheath A124, while in other embodiments the endoscope A120 is inserted into the sampling sheath A124 prior to being placed in the single sterile package.

At step A1215, the endoscope A120 is connected to the processor module A102. At step A1220, the processor module A102 is turned on and a manual white balancing procedure is undertaken. At step A1225, the fluid line A132 is connected to the syringe A134 or other supply of saline or other suitable fluid.

At step A1230, the patient's cervix is disinfected, local anesthetic is optionally applied, and the distal end A122/A126 of the medical device A100 is inserted through the patient's vagina and cervix and into the patient's uterus. During step A1230, the imaging module A108 may be relaying images to the processor module A102 for display on the integrated display A140 and/or an external display to provide direct vision during insertion. Further, saline or other fluid is infused during step A1230 via the fluid line A132 and sampling sheath A124 to distend the patient's uterus.

At step A1235, the patient's uterine/endometrial cavity is inspected using the endoscope A120. At step A1240, the fluid stopper A136 at the proximal end A138 of the sampling sheath A124 is occluded and suction is created at the distal end A126 and/or at the holes A127 of the sampling sheath A124 by applying suction on the fluid line A132 using, e.g., an empty syringe. Alternately, the fluid line A132 is occluded and suction is applied at the proximal end A138 of the sampling sheath A124 to create suction at the distal end A126 and/or holes A127 of the sampling sheath A124. According to some preferred embodiments, the sheath and endoscope are preassembled as one piece, and the endoscope does not need to be withdrawn, and there is no opening at the proximal end that needs to be plugged.

At step A1245, the sampling sheath A124 is moved in and out while being rotated and while the suction is applied to the fluid line A132 to obtain an endometrial sample. At step A1250, the sampling sheath A124 is withdrawn from the patient and the endometrial sample is collected. The procedure is completed at step A1255.

FIG. A13 is a flow chart showing a method of operating a device having a combined endoscope and endometrial sampling device, according to some embodiments. The method A1300 begins at step A1305 after the patient is suitably positioned for the procedure, e.g., the patient may be situated on an exam room table.

At step A1310, a sterile package including the endoscope A120 and/or a sterile package including the sampling sheath A124 are opened. Alternately, the endoscope A120 and sampling sheath A124 are both included in a single sterile package that is opened at step A1310. In some embodiments, at step A1310 the endoscope A120 may be inserted into the sampling sheath A124, while in other embodiments the endoscope A120 is inserted into the sampling sheath A124 prior to being placed in the single sterile package.

At step A1315, the endoscope A120 is connected to the processor module A102. At step A1320, the processor module A102 is turned on, and a manual white balance procedure is carried out. At step A1325, the fluid line A132 is connected to the syringe A134 or other supply of saline or other suitable fluid.

At step A1330, the patient's cervix is disinfected, local anesthetic is optionally applied, and the distal end A122/A126 of the medical device A100 is inserted through the patient's vagina and cervix and into the patient's uterus. During step A1330, the imaging module 1A08 may be relaying images to the processor module A102 for display on the integrated display A140 and/or an external display to provide direct vision during insertion. Further, saline or other fluid is infused during step A1330 via the fluid line A132 and sampling sheath A124 to distend the patient's uterus.

At step A1335, the patient's uterine/endometrial cavity is inspected using the endoscope A120. In those embodiments implemented using the medical device A100 described above in relation to FIG. A9, at step A1340, the clamp or valve A910 is opened to unlock the fluid line A133. Suction is created at the distal end A126 and/or at the holes A127 of the sampling sheath A124 by applying suction on the fluid line A132 using, e.g., an empty syringe to create outflow in both fluid lines A132 and A133. The method may then proceed to step A1350 as shown in FIG. A13.

In those embodiments implemented using the medical device A100 described above in relation to FIG. A10, the method may skip step A1340 and go to step A1345. At step A1345, suction is applied to fluid line A133 using syringes A134A. This creates a flow-through of the saline liquid and rinses our blood and debris. The method may then proceed to step A1350 as shown in FIG. A13.

At step A1350, the sampling sheath A124 is moved in and out while being rotated and while the suction is applied to the fluid line A132 or fluid line A133 to obtain an endometrial sample.

At decision block A1355, it is determined if an option exists to withdraw the endoscope A120. If yes, then at step A1360, the endoscope A120 is removed while the sampling sheath A124 remains within the patient. At step A1365, the fluid stopper A136 at the proximal end A138 of the sampling sheath A124 is occluded and at step A1370 suction is created at the distal end A126 and/or at the holes A127 of the sampling sheath A124 by applying suction on the fluid line A132 or fluid line A133 using, e.g., an empty syringe.

At step A1375, the sampling sheath A124 is withdrawn from the patient and the endometrial sample is collected. The procedure is completed at step A1380.

If it is determined at decision block A1355 that the endoscope is not to be withdrawn or the option to withdraw the endoscope does not exist, the method goes to step A1375 and A1380 where the sampling sheath A124 is withdrawn from the patient, the endometrial sample is collected and the procedure is completed.

FIGS. A14A-A14D illustrate a device A1400 for combined hysteroscopy and endometrial biopsy according to some embodiments. Many of the elements of the embodiment shown in FIGS. A14A-A14D are the same as or similar to those discussed in the previously described embodiments, and such elements may not be described or may only briefly be described. It will also be appreciated that the aspects of the embodiments previously described may also apply to the present embodiments. FIG. A14A is a left-side view; FIG. A14B is a right side view; FIG. A14C is a top view; and FIG. A14D is a bottom view of the device A1400, according to some embodiments. The device A1400 is particularly advantageous for enabling a physician to perform an efficient diagnostic outpatient office or clinic procedure for a female patient who is reporting abnormal uterine bleeding, the procedure combining a hysteroscopic examination with an endometrial biopsy, although it is to be appreciated that other uses for the device A1400 are within the scope of the present teachings. The device A1400 can bring about substantial efficiencies in terms of keeping equipment costs low and keeping the time required to perform the procedure modest, while at the same time providing the opportunity for better endometrial sample quality over conventional "blind" endometrial sample collection methods.

Device A1400 comprises a handle portion A1401 and a sampling portion A1404 that detachably couples to the handle portion A1401. Preferably, the sampling portion A1404 is a single-use-only disposable item, whereas the handle portion A1401 is reusable. The handle portion A1401 comprises a handle body A1402 that houses a rechargeable battery and the various electrical components discussed supra, as well as a video display A1440 that is integrally formed therewith. According to one embodiment, the handle body may have a longitudinal dimension "b" of about 4 inches and a diameter of about three-fourths of an inch, while the video display A1440 can be a 3-inch diagonal LCD screen having a thickness "a" of about one inch in the longitudinal direction. The video display A1440 is generally oriented in a plane that is transverse to the longitudinal direction such that it can be viewed by the physician who is performing the procedure while the sampling portion is extended into the patient's vagina and uterus. According to some embodiments display A1440 is tiltable upwards and downwards so as to improve ergonomic performance under some circumstances. FIG. A14A shows an example of an upward tilt angle a of display A1440. According to some embodiments the display A1440 is tiltable upwards by about 45 degrees and downwards by about 45 degrees.

Sampling portion A1404 comprises a sampling sheath A1424, an imaging head A1408, and a fluid and connector hub A1405 configured as illustrated in FIGS. A14A-A14D. Sampling sheath A1424 forms a single hollow lumen extending along its length, within which lumen is contained a narrow electrical cable A1499 (shown dotted-line) that provides the required electrical connectivity between the handle portion A1401 and the imaging head A1408. By way of example and not by way of limitation, the sampling sheath A1424 may have an outer diameter of 3.1 mm, an inner diameter of 2.6 mm, and a length "d" of at least 6.5 inches, and has a firm yet partially flexible mechanical nature. The sampling sheath A1424 is preferably made of an optically clear material so that the fluid(s) therein, including the endometrial sample itself near end of the procedure, can be easily viewed by the physician. The electrical cable A1499 preferably has a diameter that is about 1 mm or less if needed.

According to one example embodiment, sheath A1424 has a total length of about 233 mm, made up of a straight portion which is about 172 mm long, and an upwardly curved portion which is about 20.7 degrees at having a radius of about 174 mm. The curved portion raises the tip 15.6 mm as shown in FIG. A14A. According to some embodiments, the connector hub A1405 can have a length "c" of 1.25 inches. Preferably, the imaging head A1408 comprises camera optics having an angular field of view of at least 100 degrees.

A sampling port A1427 is formed in the sampling sheath A1424 near the distal end and according to some embodiments, has a penny whistle-type shape configured to facilitate endometrial sample collection when moved along a tissue surface in a scraping motion.

FIGS. A18A-A18D illustrates closer views of the distal end of the sampling portion A1404 including the sampling port A1427, according to some embodiments. In particular, FIG. A18A is an end view; FIG. A18B is a cross section; and FIG. A18C is a perspective view. For one embodiment, the general dimensions (e.g., length, inner and outer diameter), the material type, the general mechanical characteristics (e.g., stiffness, smoothness), and the nature and dimensions of the sampling port A1427 of the sampling sheath A1424 may be similar to corresponding components of the MedGyn Endosampler Model 22720 (3 mm) available from MedGyn Products, Inc. of Lombard, Ill., with the exception that there is the imaging module A1408 integrated into its distal tip, and the thin electrical wiring cable A1499 running down its length.

According to some embodiments, the sheath A1427 has an oblong cross section so as to allow room for a forward facing port A1824 which allows fluids flowing into the uterine cavity (in-flow fluids) to pass out of the distal end near the camera A1830. The camera block A1830 includes an aperture A1838 through which the video images are obtained. By providing an in-flow port on the distal end of sheath A1427 the video quality can be increased. In addition to providing room for the in-flow port A1824, the oblong cross section allows the sampling port A1427 to be positioned closer to the distal end of the sheath A1427. According to one embodiment, the outer dimension of the sheath A1424 is about 4.6 mm by 3.8 mm, and the inner dimension is about 3.8 mm by 3.0 mm. Also shown are LEDs used for illumination, such as LED A1834. The space surrounding camera A1830 that is not used for the in-flow port A1824 is filled in using a suitable glue filler A1814. As shown in FIG. A18B, the distal end A1816 of the sheath A1824 is preferably beveled.

Talon shaped opening A1427 allows for more efficient collection of endometrial tissue samples. Sharp tip A1820 of opening A1427 allows for scraping of endometrium. According to one embodiment, suitable dimensions for the opening A1427 for a sheath having the dimensions shown in FIG. A18A are shown in FIG. A18B. Shown in FIG. A18C are dashed arrows illustrating fluid flowing between the multi-purpose fluid channel A1812 within the sampling sheath A1424 and the ports A1427 and A1824.

FIG. A18D shows a front view of the distal end having a ring-shaped LED A1836, according to some embodiments. The LED A1836 is formed in a recessed ring-shaped area surrounding the aperture A1838 as shown. In general the LED or LEDs can be placed as close a possible to the aperture of the camera so long as the LED or LEDs do not block the field of view of the camera. According to some embodiments, a ring-shaped LED mounting ring is used such as shown and described with respect to FIGS. A29A and A29B.

Referring again to FIG. A14A-A14D, according to some embodiments, the handle portion A1401 is provided with a relatively minimal set of external controls buttons or knobs. In particular, a hardware button A1456 is used for power control (on/off button), an two hardware buttons A1452 and A1454 are used for manual gain control of the LCD screen A1440. According to some embodiments third and fourth hardware buttons A1453 and A1455 are used for manual white balance and to capture still images from the video camera for later viewing, respectively. According to some embodiments, programmable buttons can be provided in place of some or all of the hardware buttons, and hardware or programmable buttons can be provided to control other video features such as zoom-in, zoom-out and manual white balance.

In addition to providing the required electrical connections between the handle portion A1401 and the electrical cable A1499, the fluid and connector hub A1405 is configured to provide a multi-purpose fluid channel between a fluid coupling opening A1403 and the port or ports at the distal end (such as sampling port A1427 and the in-flow port). During a hysteroscopic phase of the procedure, the multi-purpose fluid channel between the opening A1403 and the distal ports is used to carry a fluid (such as saline solution) that is infused under positive pressure from an external source, such as a syringe A1435a coupled to the opening A1403, toward and outward from the distal end ports (such as in-flow port A1824 shown in FIGS. A18A and 18C, and sampling port A1427) to distend the uterus. Other examples of distending fluids that may be suitable according to some embodiments include: carbon dioxide gas, electrolyte-poor fluid, and electrolyte-containing fluid. The multi-purpose fluid channel (channel A1812 shown in FIG. A18C) is then used to drain the uterus upon application of a negative pressure (suction), such as can be provided by the external syringe, to the opening A1403. Subsequently, during a sample collection portion of the procedure, the multi-purpose fluid channel continues to provide suction to the sampling portal A1427 such that sample tissue is sucked thereinto and stored. The use of the same fluid channel to perform these different functions during different phases of the combined procedure provides an advantageous balance of device functionality and simplicity of device manufacturing.

Notably, the presence of the narrow electrical cable A1499 within the sampling sheath A1424 does not substantially disturb the operation of the multi-purpose fluid channel nor does it negatively affect the quality of the acquired endometrial sample. At the same time, placement of the narrow electrical cable A1499 within the multi-purpose fluid channel serves to enhance the simplicity of the device and lower the manufacturing costs. However, it is to be appreciated that it is not outside the scope of the present teachings for the electrical cable A1499 to be disposed within a separate second lumen formed in the sampling sheath A1424, or alternatively to be adhered along its length to the outside surface of the sampling sheath A1424, although these configurations are not believed to be quite as advantageous as the embodiment of FIGS. A14A-A14D in which the narrow electrical cable A1499 shares the hollow lumen of the sampling sheath A1424 with the multi-purpose fluid channel.

According to some embodiments a data-transfer port A1433, in the form of a USB port is provided on the exterior of handle A1402. The USB port A1433 can be used to transfer data such as video or still captures stored in memory A1437 from the device A1400 to a computer or other system. The USB port A1433 can also be used to calibrate, setup and/or change settings on the device A1400 or otherwise communicate with processor A1439. According to some embodiments, the USB port can be used to supply power to the device A1400 either for operation or for charging of rechargeable battery A1435.

FIGS. A15A-A15D illustrate the device A1400 at respective phases of a method for combined hysteroscopy and endometrial sampling according to some preferred embodiments. For clarity of presentation, the fluid and connector hub A1405 is illustrated in FIG. A15A as a dotted line, such that a fluid stopper A1536 is visible that is configured to prevent fluid from flowing further toward the handle portion A1401, while at the same time allowing the electrical cable A1499 to pass onward toward the handle portion A1401. Also shown in FIG. A15A is an external syringe A1534 including a plunger A1535 for manipulation by an assistant during the combined hysteroscopy and endometrial sampling procedure, the syringe A1534 being in fluid communication with the opening A1403 (through a fluid tube A1532) that establishes a multi-purpose fluid channel with the sampling port A1427 at the distal end. The physician, whose eye is shown by the graphical symbol "E" in FIG. A15A, directs the distal tip of the device toward the cervix under the full or partial guidance provided on the video display A1440. Advantageously, the physician does not need to turn his/her head away in order to look at the video display.

As illustrated in FIG. A15B, once the distal end has been inserted into the uterus, positive pressure is placed on the plunger A1535 to cause distention fluid "F" to flow into the uterus through the sampling portal A1427, which causes a positive pressure to distend the uterus. The physician then performs a hysteroscopy by looking at the video display A1440 while manipulating the device to look around the uterus at different locations and viewing angles.

Depending on patient-specific factors, there might be very little leakage of the fluid "F" from the uterus during the hysteroscopy (a relatively tight seal of the cervix around the sampling sheath A1424), or alternatively there might be substantial leakage of the fluid "F" from the uterus during the hysteroscopy (a relatively loose seal or space between the cervix and the sampling sheath A1424). For the latter case (i.e., loose seal or no seal), uterine distention can be maintained for the necessary viewing time interval (usually between one minute and several minutes) by maintaining an inflow of replacement fluid from the sampling portal A1427 into the uterus as the fluid "F" leaks out from the cervix. If necessary, the assistant can refill the syringe with fluid if it runs out. Alternatively or in conjunction with a manually controlled syringe, any of a variety of automated external fluid pumping systems can be used to introduce, maintain, and/or evacuate the uterine distention fluid "F" including, but not limited to, the handle-mounted fluid pumping scheme that is included in FIGS. A21A-A21B infra.

As illustrated in FIG. A15C, upon completion of the hysteroscopy phase of the procedure, a negative pressure is applied to the multi-purpose fluid channel within the sampling sheath A1424, such as by an outward pulling on the plunger A1535 of syringe A1534, thereby causing a drainage of the fluid "F" outward from the uterine cavity and back into the syringe (which can be accompanied by leakage-type drainage of the fluid "F" out of the cervix, depending on patient-specific factors as described above). By virtue of the drainage of the distention fluid "F", the uterus collapses around the sampling sheath A1424.

As illustrated in FIG. A15D, an endoscopic biopsy phase of the procedure is then carried out by moving the sampling sheath A1424 in an inward and outward motion several times, with the assistance of further negative pressure maintained by continued pulling of the plunger A1535 of the syringe A1534, an endometrial sample "S" thereby being scraped off the internal uterine surface by virtue of the shape of the sampling portal A1427 and sucked into the multi-purpose fluid channel within the sampling sheath A1424 by virtue of the negative sucking pressure. Advantageously, the endoscopic biopsy phase of the combined procedure can be carried out immediately subsequent to the hysteroscopy phase without requiring the retraction and reinsertion of any instruments, thereby streamlining the procedure from a time and complexity standpoint. Advantageously, the device A1400 brings about the ability for only a single insertion to be required in achieving the dual goals of hysteroscopy and endometrial biopsy. The simplicity of the device allows for use in a regular office setting (rather than a surgical setting) and decreased physician time. The device allows for the ability to perform a hysteroscopy in the doctor's office in addition to an endometrial biopsy, with only very modest additional time and equipment required in comparison to a non-hysteroscopic "blind" endometrial biopsy that would be performed in that same setting, but being much more effective than the simple "blind" biopsy because much common pathology is diagnosed by visual appearance, such as submucous fibroids and polyps, which would be missed by blind biopsy.

An additional advantage provided by the device A1400 and the method of FIGS. A15A-A15D is that the physician's observations made during the hysteroscopy portion of the procedure can be used in providing a more directed endoscopic biopsy procedure, which can yield better sample quality in comparison to "blind" endoscopic biopsy procedures. More particularly, according to an embodiment, the physician may notice a particular area of interest on the interior uterine surface during the hysteroscopy phase, whereupon the physician may then "steer" the sampling port A1427 toward that particular area of interest during the endoscopic sampling phase. This can be particularly advantageous in for cases in which the uterus contains relatively small lesions or polyps whose cancerous tissue might otherwise be missed or diluted in a "blind" procedure. By way of example, the longitudinal axis of the device A1400 may be thought of as the center of a clockface coordinate system when viewed from an axial direction by the physician, and the uterus can be conceptually divided into quarter sections in that clockface coordinate system. For a patient in a conventional supine position, an anterior portion of the uterus on the patient's left side would correspond to clockface positions between 12 o'clock and 3 o'clock. A posterior portion of the uterus on the patient's left side would correspond to clockface positions between 3 o'clock and 6 o'clock. A posterior portion of the uterus on the patient's right side would correspond to clockface positions between 6 o'clock and 9 o'clock, and, finally, an anterior portion of the uterus on the patient's right side would correspond to clockface positions between 9 o'clock and 12 o'clock. In one example scenario, the physician may notice during the hysteroscopy that there is a particular area of interest between 6 o'clock and 9 o'clock in the above-described coordinate system, such as a small polyp. Advantageously, the physician may then turn the device 1400 to the appropriate angle (using, for example, a fiducial marker system provided on the exterior of the device, or an intrinsic fiducial marker system provided by virtue of the shape of the device) to perform most or all of the endometrial sampling phase with the sampling port A1427 facing angles between 6 o'clock and 9 o'clock. In this manner, it is more likely that the endometrial sample will contain the potentially cancerous tissue than if a "blind" endometrial biopsy were taken.

FIGS. A16-A17 illustrate further detail of the handle and display portions of a sampling endoscope, according to some embodiments. As can be seen the dimensions of the handle A1402 and display A1440 are provided according to a sample embodiment. The various buttons A1452, A1452, A1455 and A1456 are also shown as described with respect to FIGS. A14A-A14D.

Thus, according to some embodiments, a handheld video endoscope integrates endoscope, video processing electronics A1439, data storage A1437, compact display A1440 and embedded power supply A1435 for efficient and convenient clinical procedures. The design should be adapted to be suitable for each specific type of procedure to minimize patient discomfort while maximizing clinical efficacy.

According to some embodiments, an ergonomically designed handheld hysteroscope is provided. In particular, the display A1440 is mounted on the back end of the device and relatively centered with respect to the shaft of the endoscope. The screen of display A1440 is situated at the center of the physician's field of view while performing the procedure. The design shown advantageously provides a low off-axis profile, which allows the physician to move the device freely including rotation and longitudinal motion without bumping into the patient's legs or into the table.

The screw driver type handle body A1402 is preferably about 1.0 inches in width. Display screen A1440 is about 3 to 5 inches measured diagonally. The design provides for easy longitudinal translation as well as easy rotation. Slim design facilitates easy hand grip and longitudinal movement. Video display screen A1440 is mounted with low overall off-axis profile for easy rotation or tilting.

FIGS. A21A-A21B illustrate a sampling endoscope having a pistol grip, according to some embodiments. Many of the elements of the embodiment shown in FIGS. A21A-A21B are the same as or similar to those discussed in the previously described embodiments, and such elements may not be described or may only briefly described. It will also be appreciated that the aspects of the embodiments previously described may also apply to the present embodiments. Sampling endoscope A2100 is similar to endoscope A1400 depicted in FIGS. A14A-A14D, A16 and A17 except that a pistol handle A2100 is provided. According to some embodiments, the endoscope probe sheath A1424 and video display A1440 can rotate while the pistol handle A2110 remains stationary. Zooming and capture buttons A2160 can be provided on pistol grip A2110 as shown. According to some embodiments, the handle body A1402 rotates along with the probe A1610 and display assembly A1640, and according to other embodiments the handle body A1632 remains stationary relative to pistol grip A2110. According to some embodiments, the fluid connector A1622 and hub assembly A1626 rotate along with the probe A1610 and display assembly A1640, and according to other embodiments the fluid connector A1622 and hub assembly A1626 remain stationary relative to pistol grip A2110. According to some embodiments, the pistol grip A2110 is disposable and according to other embodiments the grip A2110 is re-usable. By allowing the pistol grip A2110 to remain stationary while the sheath A1424 and display A1440 rotate, the physician is able to move the device freely including rotation and longitudinal motion without bumping the pistol grip A2110 into the patient's legs or into other equipment such as a table.

According to some embodiments, the sheath A1424 and hub assembly A1405 are detachable and disposable, while the handle A1402, pistol grip A2110 and display A1440 are re-usable. According to some embodiments, the rotation of the sheath and video assembly is motor driven. According to some embodiments the rotation angle is registered by the control system and can be used for rotating the image back in software. Where software rotation is implemented, according to some embodiments, only the sheath A1424 and hub assembly A1405 rotate and the image on the display A1440 is rotated in real time to compensate.

According to some embodiments, as an alternative, the manually controlled syringe of FIGS. A15A-A15D is replaced by a dedicated fluid container A2152 and trigger-actuated bidirectional pump A2150 that is affixed to or located within the handle portion A1402 or pistol grip A2110 of the device A2100, which can facilitate the ability for a physician to perform the combined hysteroscopy and endometrial sampling procedure without the need for an assistant to operate the syringe. Included in FIGS. A21A-A21B is one or more embodiments in which the device A2100 is outfitted with an enhanced pistol-grip type handle A2110, wherein the physician may apply positive or negative fluid pressure by squeezing a trigger-type button A2166. A switch A2164 is provided that allows the physician to select between positive pumping pressure and negative suction pressure. For one embodiment, the fluid pumping and suction pressure may result solely from manual squeezing of the trigger A2166, with operation being analogous that of a fillable household spray bottle having a squeeze-trigger. For another embodiment, motorized operation can be provided using electrical energy from the rechargeable battery A1435 of the handle portion or an external source. As described, for some embodiments in which a pistol-grip type handle A2100 is used, the handle portion A1402 may be configured so as to allow the trigger A2166 and handle-grip A2100 to remain at a fixed angle in one hand, while the video display A1440 and sampling sheath A1424 can be rotated in unison to different clockface angles relative to the longitudinal axis of the device. The physician may alter the angle of the video display A1440 and sampling sheath A1424 by directly manipulating the angle of the video display A1440 with their second hand. The mechanical fit between the components should be reasonably tight or resistive so that the video display A1440 and sampling sheath A1424 do not rotate loosely on their own, but will only rotate when so affirmatively manipulated by the physician's second hand.

Another variation that is also within the scope of the present teachings is to leave the video display A1440 upright and fixed in angular relation to the pistol-grip style handle A2110, while the sampling sheath A1424 is independently rotatable around the longitudinal axis. For this embodiment, the angle of the sampling sheath can be electronically or electromechanically measured, and then the angle of the image as it appears on the video display A1440 can be rotated using software or firmware running on processor A1439 to correspond to the angle of the sampling sheath.

By way of still further example, another variation that is also within the scope of the present teachings is to use a pistol-grip A2110 that is not triggered, but into which can be placed a single-use fluid syringe A1435a. The physician can use their second hand to work the syringe A1435a while holding the pistol-grip steady with their first hand. By way of even further example, another variation that is also within the scope of the present teachings is to incorporate a low-cost rotary fluid pump directly into the fluid and connector hub A1405, or to build the low-cost rotary fluid pump into the fluid tube that leads to the fluid and connector hub from an external reservoir, and to make all of the sampling portion, the reservoir, the fluid tube, and fluid pump be single-use disposable items. One example of a suitable low-cost fluid pump that could be adapted for use into the described embodiments is the WPM Ultra-Compact Peristaltic Pump available from Welco, Ltd., of Tokyo, Japan. Therefore, references to the details of the preferred embodiments are not intended to limit their scope.

Further details with respect to imaging sensors and related technology will now be provided, according to some embodiments. CMOS (Complementary metal-oxide-semiconductor) sensor technologies have advanced greatly. Pixel signal to noise is improving while pixel size is reduced, making it possible to achieve high resolution with very small sensor area. CMOS sensor requires low power and voltage. CMOS requires fewer connection wires and the wires can transmit distance up to several meters. These characteristics make CMOS sensors ideal for miniature video endoscopes for in vivo direct visualization of many different tissues of interest in human body. Because of the miniaturization, it is possible to embed video cameras in catheters, sheath and other tools and provide in vivo and sometime concurrent direct visualization.

Higher resolution and high photon flux will render higher image quality. However, there is a physics limit to the size of pixel. As the individual pixel size become smaller, the signal to noise, dynamic range decrease and circuitry complexity increases. The basic tradeoffs between image resolution, clinical value including invasiveness and the economics of single use cameras, have not been obvious and a systematic will now be provided.

FIG. A19 illustrates various factors in optimal sensor design for single use video endoscopes, according to some embodiments. Major factors in optimal sensor design for single use video endoscopes include the following. (1) Sensor Area (SA)—larger sensor area allows imaging of larger area. However, cost (C) and invasiveness (INV) increases with sensor size. (2) Adequate image quality (AIQ)—refers to image quality that provides adequate visualization. AIQ for three targeted groups of imaging applications are plotted in curves A1910, A1912 and A1914. For certain sizes of targeted area to be visualized, AIQ increases with sensor size but levels off after certain point (the level-off points A1920, A1922 and A1924), beyond which AIQ changes very slowly with SA, i.e. the quality of visualization does not change significantly. (3) Invasiveness (INV), plotted in curve A1930—as sensor area increases the invasiveness to tissue increases quickly because the video endoscope size is directly proportional to the sensor area. (4) Cost (C), plotted in curve A1932—cost of video endoscope increases as chip area increases because of chip fabrication cost. Cost also increases as size approaches very small because of assembly and packaging. Cost is very critical in making single-use feasible.

As shown in FIG. A19, an optimal area A1940 of operation is highlighted. Table 1 lists the range of sensor resolution for the 3 application groups.

TABLE 1

| Targeted Group | Pixel Size | Number of Pixels | Endoscope OD (not including illumination) |
|---|---|---|---|
| G1 | 1.75~3.0 mm | 1~2 Millions | <5 mm Such as 3.6 mm |
| G2 | 1.4~2.5 mm | 50K~270K | <3 mm Such as 1.6 mm |
| G3 | 1.1~1.75 mm | 8K~40K | <1.5 mm Such as 1.2 mm |

Thus, in applying CMOS (Complementary metal-oxide-semiconductor) sensor technologies for medical endoscopes, optimal sensor specification is achieved based on the following major factors: Adequate quality for intended use; invasiveness to the tissue; and cost of manufacturing and assembly. The current teachings, according to some embodiments, relate to single-use video endoscopes or video probes for several common diagnostic and therapeutic procedures including single-use, flexible and miniature endoscope is inserted through, or fixed within, the working channel of sheath or catheter to assist the deployment and verification of biopsy and ablation with RF or Microwave. With single-use, flexible and miniature endoscope built-in the sheath or catheter, the targeted tissue sites and can be visualized concurrent to the RF or Microwave ablation or tissue biopsy, according to some embodiments. With single-use, flexible and miniature endoscope built-in the sheath, contraceptive sterilization procedure can be visualized and verified, according to some embodiments. Ultra-slim, single-use endoscope on a curved or angled tip for assisting deployment and verification of implant devices including IUD (Intra-Uterine Device), and for diagnosis or treatment of body joints and spines, according to some embodiments. Ultra-slim, single-use video probes that can be placed inside a cardiac catheter sheath together or in place of the usual guide wire, which enables continuous visualization of the catheterization process inside the cardiovascular vessels and enhance the procedure which reduce X-ray doses by fluoroscopy, according to some embodiments.

According to some embodiments the techniques described herein can be used for other types of direct optical visualization of the human body including for example, encephaloscopy, esophagoscopy, thoracoscopy, angioscopy, nephroscopy, proctoscopy, colonoscopy, arthroscopy, rhinoscopy, laryngoscopy, bronchoscopy, mediastinsocopy, gastroscopy, laparoscopy, amnioscopy, and cystoscopy.

Many of the embodiments described herein are directed to "single use", and this provides a significant advantage in many applications since sterilization is tedious and requires expensive materials and construction of the scopes. Additionally, sterilization can be never be perfect. "Single use" means disposability. The teachings provided herein provide a "sweet spot" or a good compromise in balancing of the invasiveness, acceptable image quality and cost.

Referring again to FIGS. A14A-A14D, A16 and A17, according to some embodiments, the handset including probe A1424, connector hub A1405 and handle A1402 is a single disposable piece. The display assembly A1440 is designed to be re-used many times. A highly durable design for the connector between the handset A1402 and the display A1440 is provided so that the display A1440 can be re-used many times.

One example of the procedure is described as follows: (1) clean and disinfect the display A1440; (2) take the handset out of sterile package and connect it to the display A1440; (3) perform the entire hysteroscopy and biopsy procedure; (4) detach handset and dispose of it; (5a) clean and disinfect display A1440; or (5b) peel a protective sheath used to cover the display A1440 and replace with a new sheath; and (6) the display A1440 is now ready to use for new procedure.

According to some embodiments, the display A1440 and handle A1402 is a single piece that is reusable. A highly durable design for a connector between the handle A1402 and hub A1405 allows for the display and handle to be reused many times.

According to some embodiments, the endoscopic system is formed of three main parts. Display A1440 is designed to be reused many times. Handle A1402 is designed to be reused fewer times, and sheath A1424 and hub A1405 are designed for single use.

Conventional video endoscopes use a sheath containing channels for multiple purposes, including instilling distending media and or collecting tissue samples. According to some embodiments, the design of the distal tip of an endoscope that includes a video camera and illumination, combined with a channel for instillation of distending fluid or gas. Specifically, structures for fluid inflow allow a solid rounded distal end of the device to enter the uterus, urethra, or other hollow organ while maintaining forward flow of distending medium to provide excellent visualization. According to some embodiments, the use of this principle is combined with a built-in endometrial biopsy port to allow directed biopsy without the need to insert other instruments.

FIGS. A20A-A20C illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example embodiments, the sheath A1424 having OD less than about 4 mm. A backward facing side port A2022 is angled backward such that the in-flow fluid is naturally directed toward the forward facing side port A2024. The forward facing side port A2024 is preferably angled at less than 30 degrees from the central axis of sheath A1424 near its distal end.

Multi-purpose fluid channel A1812 is used to carry fluids under positive pressure outward from the device, for example to distend the uterus, as well as to carry fluids under negative pressure inward into the device, for example for sample collection. A flex cable or wire A1499 is also shown and can be embedded within the wall of sheath A1424, or more preferably, positioned within the channel A1812. The camera head A1830 in this example has an OD of between 1 and 2.62 mm, and an aperture A2038. Illumination is provided by LEDs, such as LEDs A2034 and A2036.

According to some embodiments an optional soft flap A2026 is provided for gating in-flow fluid (i.e. fluid flowing into the uterus) through forward facing port A2024 instead of backward facing port A2022. The optional soft flap A2026 is designed to at least partially occlude the backward port A2022 in the in-flow phase, thereby forcing most or all of the fluid under positive pressure through the forward port A2024.

By providing the two ports as shown the design advantageously provides for efficient and effective bi-directional sampling. Backward facing port A2022 captures more samples when sheath moves backwards, while forward facing port A2024 captures more samples when sheath moves forwards. FIG. A20C shows further details of the shape of the forward facing port A2024 and backward facing port A2022, and dimensions, according to one embodiment.

Thus, by providing more than one port at or near the distal end, in-flow of fluids as well as sample collection is facilitated. As shown the lateral forward port A2024 is provided with angled ramp that allows the inflow fluid to be injected with a trajectory at an angle equal or less than 30 degrees from the forward direction. With the design shown in FIGS. A20A-A20C, there is no need for an opening at the very distal tip surface. This frees up more room for camera, as well as for LEDs or other illumination means. This also allows a solid rounded distal end to facilitate entry into the uterus, urethra, or other hollow organ while maintaining forward flow of distending medium to provide excellent visualization. Thus by providing dual ports or multiple ports, samples can be captured whether the device move forward or backward or rolling.

FIGS. A22A-A22B illustrate an endoscope having optical fiber illumination, according to some embodiments. Endoscope A2200 is similar to device A1400 or device A2100 as shown in and described with respect to FIGS. A14A-A14D, A15A-A15D, A16, A17, A18A-A18D and/or A21A-A21B. In this example, however, illumination is provided by a high brightness LED module A2228 that is embedded inside the hub body A2226 as shown. The LED light couples into optical fibers embedded within the wall of sheath A1424. The population of optical fibers, such as fiber A2214 shown in FIG. A22B, is embedded into the sheath material A2212 of sheath A1424. The optical fibers can be glass (or plastic) light guiding fibers as is well known, which carry illumination light from the LED source A2228 to the distal tip A1408. At the distal tip A1408 the optical fibers are terminated and sealed or covered with light translucent materials. According to some embodiments, the optical fibers each have a diameter of about 30 Microns and a numerical aperture of >0.7. The fibers are preferably held together with epoxy and polished at the end for coupling with the LED source A2228. The top section A2230 of sheath A1424, which also corresponds to the same sector as the irrigation and sample retrieval port A2208, contains no fibers and remains optically clear so as to allow the user to see specimen sample fluid as the fluid is being drawn through the central opening A1812 of sheath A1424. This "clear sector" A2230, according to some embodiments, takes up between 25-50% (i.e. 90-180 degrees) of the sheath wall circumference. According to one embodiment, the clear sector A2230 is spiraled along the length of the sheath A1424 so that the user can view the specimen fluid from any viewing angle.

FIGS. A23A-A23D illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, the wall of sheath A1424 has OD of less than about 4 mm. The backward facing side port A2322 is tilted backward so as to direct the in-flow fluid (i.e. fluid flowing into the uterus) in multi-purpose fluid channel A1812 toward the forward port A2324. Forward facing side port A2324 is preferably angled at less than 30 degrees. A flex cable or wire A1499 is connected to camera head A1830, which preferably has an OD of between 1 mm and 2.62 mm, and an aperture A2338. Illumination is provided by LEDs such as LEDs A2334 and A2336. Forward facing port A2324 preferably has a blunt edge A2328 to facilitate ease of insertion of the endoscope by lessening risk that the edge A2328 catches on tissue during insertion. According to some embodiments, an optional soft flap A2326 is provided for gating in-flow fluid through forward facing port A2324 instead of backward facing port A2322.

FIGS. A23C and A23D shows further details of the shape and dimensions of the backward facing port A2322 and forward facing port A2324 respectively, according to some embodiments. As in the case of the design shown in FIGS. A20A-A20C, the design shown in FIGS. A23A-A23D provide for bi-directional sampling. Backward facing port A2322 captures more samples when sheath moves backwards; while forward facing port A2324 captures more samples when sheath moves forwards.

FIGS. A24A-A24B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example forward facing port A2424 and backward facing port A2422 are on the opposite side of the sheath tube A1424 to allow in-flow fluid to be more uniform on all sides of sheath A1424. Forward facing port A2424 is more proximal relative to the backward port to allow the backward facing port A2422 to be closer to the distal end of sheath A1424. Forward facing port A2424 has an edge A2428 that is preferably rounded to avoid catching up tissue. In one embodiment camera wire A1499 and is pushed up within multi-channel fluid channel A1812 so as to be closer the upper wall of sheath A1424, such as by gluing, etc. This has been found to allow greater in-flow fluid to the forward port A2424.

Block or stuffing A2426 behind the camera module A1830 is shaped so at to direct the in-flow fluid to the forward port A2424. According to some embodiments, sheath A1424 including its distal end can be made of a single piece of suitable plastic material. Alternatively, distal tip can be made of metal while the portions of the sheath A1424 other than the tip are made of plastic material. The structures shown allow for fluid inflow, while the solid rounded distal end facilitates entry into the uterus, urethra, or other hollow organ while maintaining forward flow of distending medium to provide excellent visualization.

FIGS. A25A-A25B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, a backward facing side port A2522 is angled backward such that the in-flow fluid is naturally directed toward the forward facing port A2524. The forward facing port A2524 is formed in the very distal end of sheath A1424 as shown.

Multi-purpose fluid channel A1812 is used to carry fluids under positive pressure outward from the device, for example to distend the uterus, as well as to carry fluids under negative pressure inward into the device, for example for sample collection. A flex cable or wire A1499 is also shown and can be embedded within the wall of sheath A1424, or more preferably, positioned within the channel 1812. The camera head A1830 has an aperture A2538. Illumination is provided by LEDs, such as LEDs A2534 and A2536. A filling A2514 such as glue is used to hold the camera A1830 and to fix the position and orientation of the LEDs as shown. By providing the in-flow port A2524 on the tip of the device as shown, clear fluid such as saline can wash over the aperture of camera A1830 and illumination LEDs so as to enhance imaging quality. Additionally, the design allows for the backward facing side port A2522 to be positioned closer to the distal end of sheath A1424 which enhances the ability to efficiently collect tissue samples.

FIGS. A26A-A26B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, the sheath A1424 has an oblong cross section. A backward facing side port A2622 is angled backward such that the in-flow fluid is naturally directed toward the forward facing port A2624. Forward facing port A2424 is more proximal relative to the backward port to allow the backward facing port A2422 to be closer to the distal end of sheath A1424. Forward facing port A2624 has an edge A2628 that is preferably rounded to avoid catching up tissue.

Multi-purpose fluid channel A1812 is used to carry fluids under positive pressure outward from the device, for example to distend the uterus, as well as to carry fluids under negative pressure inward into the device, for example for sample collection. A flex cable or wire A1499 is also shown positioned within the channel A1812. The camera head A1830 has an aperture A2638. Illumination is provided by LEDs, such as LEDs A2634 and A2636. A filler A2614 such as glue is used to hold the camera A1830 and to fix the position and orientation of the LEDs as shown. The oblong cross section of sheath A1424 has been found to allow the sampling port to be placed closer to the distal tip while also creating room for in-flow fluid port A2624 and sampling port A2622 to be placed on opposite sides of the sheath A1424 as shown.

FIGS. A27A-A27B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, the sheath A1424 has an oblong cross section. A backward facing side port A2722 is angled backward such that the in-flow fluid is naturally directed toward the forward facing port A2724. The forward facing port A2724 is formed in the very distal end of sheath A1424 as shown.

Multi-purpose fluid channel A1812 is used to carry fluids under positive pressure outward from the device, for example to distend the uterus, as well as to carry fluids under negative pressure inward into the device, for example for sample collection. A flex cable or wire A1499 is also shown positioned within the channel A1812. The camera head A1830 has an aperture A2738. Illumination is provided by LEDs, such as LEDs A2734 and A2736. A filler A2714 such as glue is used to hold the camera A1830 and to fix the position and orientation of the LEDs as shown. The oblong cross section of sheath A1424 has been found to allow the sampling port A2722 to be placed closer to the distal tip while also creating room for in-flow fluid port A2724 on the tip of the device as shown. By providing the port A2724 on the tip, clear fluid such as saline can wash over the aperture of camera A1830 and illumination LEDs so as to enhance imaging quality.

FIGS. A28A-A28B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, the sheath A1424 has an oblong cross section and front facing port A2824 is positioned on the distal tip and above the camera A1830. This design allows for the backward facing side port A2822 to be placed even more closely to the distal end of sheath A1424. The multi-purpose fluid channel A1812 carries fluids under positive pressure outward from the device, for example to distend the uterus, as well as to carry fluids under negative pressure inward into the device, for example for sample collection. Flex cable or wire A1499 is positioned within lower part of the channel A1812, preferably opposite to the sampling port A2822 and in-flow port A2824. The camera head A1830 has an aperture A2838. Illumination is provided by LEDs, such as LEDs A2834 and A2836. A filler A2814 such as glue is used to hold the camera A1830 and to fix the position and orientation of the LEDs as shown.

FIGS. A29A-A29B illustrate details near the distal end of a device having combined hysteroscopy and endometrial sampling capability, according to some embodiments. The device can be such as device A1400 or device A2100 as shown in and described with respect to FIGS. A14A-A14D, A15A-A15D, A16, A17, A18A-A18D and/or A21A-A21B. In this example, the sheath A1424 has an oblong cross section and front facing port/lumen A2924 is positioned on the distal tip and above the camera block A1830. The sheath A1424 is also molded into a multi-lumen tip structure. The sheath material A1424 is used to separate the camera housing A1830 from the in-flow lumen A2924. It has been found that this design prevents adhesives used for mounting the camera block A1830 from seeping into the in-flow lumen A2924. The multi-purpose fluid channel A1812 carries fluids under positive pressure outward from the device, for example to distend the uterus, as well as to carry fluids under negative pressure inward into the device, for example for sample collection. Flex cable A1499 is positioned within lower part of the channel A1812, preferably opposite to the sampling port A2922 and in-flow port A2924. In this design, the camera block A1830 is partially housed by the sheath material such that forward fluid pressure is not applied directly to the camera module directly, thereby reducing the risk of the camera module being dislodged by the in-flow fluid. Also preferably included is a wrapper or sleeve A2914 for the camera block A1830. In FIG. A29B, further detail of the camera block A1830 can be seen, as will be shown in described in even greater detail herein below. Six LEDs, such as LEDs A1934 and A1936 are mounted on a ring-shaped LED housing A3034. The camera centrally located and has an aperture A1938. A light shield A3076 acts a lens hood and shields direct light from the LEDs from entering the aperture. Portion A2940 is part of the sheath A1424 located further away from the distal tip, near to the sampling port A1922 in longitudinal position.

FIG. A30 is a cross sectional view illustrating further detail of a camera module for use with a device having combined hysteroscopy and endometrial sampling capability, according to some embodiments. The CMOS sensor A3080 and glass lens A3070 are housed within a stainless steel lens holder A3056 such that there is an air gap A3054 in between. The CMOS sensor A3080 electronically communicates via conducting wires such as wires A3052 that pass through cable A1499. The same or similar wires can provide power to LEDs near sensor A3080. The cable A1499 is supported by a grommet A3050. The entire camera module A1830 is housed and protected by a stainless steel outer housing A3060. A metallic aperture plate A3074 has a small aperture A3038 through which light is allowed to pass. The aperture plate A3074 is covered by a glass plate A3072 which is mounted slightly recessed from the most distal end of the camera module A1830. A number of LEDs, such as LEDs A3036 and A3037 are mounted on ring-shaped LED housing A3034. A light shield A3076 is positioned between the LEDs and the aperture A3038 so as to block light from the LEDs from directly entering the aperture thereby enhancing the video images captured by CMOS sensor A3080.

FIG. A31 illustrates a device having combined hysteroscopy and endometrial ablation capability, according to some embodiments. Global endometrial ablation (GEA) is being used widely for treating women with abnormal uterine bleeding conditions. Many different technologies and platforms have been developed, such as the NovaSure® system, ThermaChoice® system and also systems that employ microwave, or other sources of thermal, laser, radiofrequency, microwave energy as well as other energy sources. However, none of these systems (other than those which circulate heated free fluid under hysteroscopic vision) or procedures have been integrated with direct visualization. An endoscope or ultrasound may be used prior to the application of the GEA device, but not in the same insertion. The device A3100 integrates visualization for visually guided GEA procedures. In particular, the device A3100, in addition to the features of a conventional GEA system such as the NovaSure® system, includes a miniature camera unit A1830, which can be as described in FIG. 30 and/or elsewhere herein. The camera unit A1830 electronically communicates via cable A1499. The distal tip of sheath A1424 also preferably includes an illumination source (not shown). An integrated display A1440 is preferably mounted on the end of handle portion A2110 so as to aid in visualization during the GEA procedure. According to some embodiments, the integrated visualization components are mostly single use or disposable with the GEA components.

FIGS. A32A-A32C illustrate the distal end of a device having combined hysteroscopy and endometrial ablation capability, according to some embodiments. The distal tip of the sheath A1424 includes two tapered end pieces A3220 and A3222 that are shaped so as to facilitate insertion of the device through the cervix and into the uterus of the patient. Also shown is the folded electrode structure A3210 that includes an expandable conductive mesh as is known. In the embodiment shown in FIG. A32A, and LED A3234 is mounted near the tip of piece A3222 and LED A3236 is mounted near the tip of piece A3220. The LEDs and the camera module A1830 are electrically connected to the system via cable A1499. The mounting location of the LEDs A3234 and A3236 are preferably slightly away from the central axis of sheath A1424 so as to reduce the amount of light from LEDs directly entering the camera module A1830. According to some embodiments, the camera module A1830 is 2 mm or less in diameter. FIG. A32B illustrates an embodiment where the two pieces A3222 and A3220 are made from a translucent material, and LEDs A3244 and A3246 are mounted within the pieces A3222 and A3220 respectively. FIG. A32C illustrates an embodiment where the LEDs are mounted in a small ring-shaped holder A3254 surrounding the camera module A1830, such as shown and described with respect to FIGS. A29A-A29B and A30. The embodiments of FIGS. A32A-A32B have an advantage over the embodiment of FIG. A32C in that the overall size of the combination of the ring-shaped LED holder A3254 and camera module A1830 is larger than the camera module alone.

According to some embodiments, the illumination is provided by a source in the handle of the device A3100 and optical fiber(s) are used to carry the light to the distal tip, such as shown and described with respect to FIGS. A22A and A22B herein. For example, high brightness LEDs can be used within the handle structure A2110 of device A3100, and light-guiding optical fibers can either be mounted on the inner surface of sheath A1424 or embedded into the wall of sheath A1424. At the distal tip of device A3100, the optical fibers are terminated and sealed or covered with light translucent materials.

FIGS. A33A-A33C illustrates the device A3100 at respective phases of a method for combined hysteroscopy and endometrial ablation according to some embodiments. In FIG. A33A, the distal end of sheath A1424 is inserted through the cervix A3310. Fluid is infused through sheath A1424 so as to distend the uterine cavity A3320. The camera module A1830 has a field of view A3330 and provides visual images to the medical practitioner(s) of the inner surfaces of uterine cavity A3320 such as endometrium A3322. In FIG. A33B, the visual images from camera module A1830 are used to guide the ablation sheath A1424 to the top of the uterus (fundus). Through the aid of visual images, the integrated hysteroscopy and endometrial ablation device has the advantages of (1) reducing the risk of perforation of the uterine tissues; and (2) helps to ensure a central positioning of the sheath within the uterine cavity A3320 so as to enhance an even distribution of the electrode structure.

In FIG. A33C, the sheath A1424 is pulled back together with the camera, allowing the electrode mesh structure A3340 to expand and conform to the shape of the uterine cavity for ablation. According to some embodiments, the camera is designed to remain near the distal tip of the electrode mesh structure A3340. After deployment of the mesh structure 3340, the ablation procedure is carried out.

Although the embodiments described in FIGS. A31, A32A-A32C and A33A-A33C are for a device having combined hysteroscopy and GEA capability with a systems such as the Novasure® system, according to other embodiments, the same or similar components are combined with GEA systems having other types of ablation sheaths and/or use other types of GEA technology. In general, visualization provided by the described embodiments ensures that the GEA device is correctly inserted into the uterine cavity and minimizes the risk of a perforation. Without the integrated visualization provided by these embodiments, cavity integrity tests are indirect and not always accurate.

Certain embodiments described above can be used as a low-cost medical instrument that is disposable at least in part and in a single insertion distends, images and biopsies a patient's uterus. The device comprises an elongated conduit having a distal portion configured and dimensioned for insertion into the patient's uterus, and a proximal portion. Non-limiting examples of such a conduit are sampling portion A104, A1404, and probe A1424, without or together with connection or hub A200, A300, A400, and A1405, The conduit comprises (a) one or more proximal ports at the proximal portion of the conduit, configured to provide passage of fluid into the conduit and of fluid and biopsy samples out of the conduit; (b) one or more distal openings at the distal portion of the sampling conduit configured to provide fluid outflow from the conduit and the inflow of fluid and biopsy samples into the conduit; and (c) one or more biopsy implements at the distal end of the conduit, configured and shaped to transfer biopsy samples from the uterus into the conduit. Non-limiting examples are: (a) for proximal ports, the opening into sheath A124 from fluid line A132 (FIG. A3), openings A103, the opening for fluid line A133 into hub A105 (FIG. A9), and opening A1403; (b) for distal openings, hole A127 and ports A127A, A127B, A1427, A2322, A2324, A2522, A2622, A2722, A2822, and A2922; and, for biopsy implements, the shaped edges and sides of the distal openings. The medical instrument further comprises a handle secured to the conduit at the proximal portion thereof and configured and dimensioned to be grasped by a user's hand and manipulated by a user to introduce the distal portion of the conduit into the patient's uterus, move the conduit's distal portion within the patient's uterus, and withdraw the conduit from the patient's uterus. Non-limiting examples of the handle are module A102, and handle A1401, A1402 (and/or pistol grip A2110). The instrument includes an imaging system at the distal portion of the sampling device. Non-limiting examples of an imaging system are imaging module 108, imaging head A1408, and camera head A1830. The instrument further includes an illumination system configured to illuminate the uterus at an illumination field viewed by said imaging system. Examples of an illumination system are illustrated at A108B, A1834, A1836, A1934, A1936, A2034, A2036, A2228 and A2214, A2334, A2336, A2436, A2534, A2536, A2634, A2636, A2734, A2736, A2834, A2836, A2934, A2936, A3036, A3037, A3234 and A3236. An image display can be secured to said handle, such as image display A140 and A1440. A control system can be secured to the handle and coupled with the imaging system, the illumination system and the image display and is configured to selectively cause, in response to user commands, the illumination system to illuminate the uterus, the imaging system to provide an image of the uterus, and the display system to display the image for viewing by the user. Examples of control systems are seen at A112, A1439 (with or without control buttons A1452-A1456 and/or the control buttons and/or trigger illustrated in FIGS. A21A-A21B). At least the conduit is configured to be disposable after a single use in a patient, but the handle may also be disposable it desired. Further, all three of the conduit, handle and display can be disposable if desired, as can the control system. The instrument is configured for a medical procedure in which the distal portion is inserted only once into the patient's uterus to provide each of (a) uterus distention by introducing fluid under positive pressure into one or more of the proximal ports, which fluid passes through the conduit and enters the uterus through one or more of the distal openings, (b) an image of the uterus by illuminating the uterus with the illumination system and imaging the illuminated uterus with the imaging system, and (c) taking biopsy samples from the uterus by engaging the uterus with the biopsy implements and drawing fluid and biopsy samples from the uterus into the conduit through one or more of the more distal openings and out of one or more of the proximal ports by applying negative pressure to one or more of the proximal ports. Preferably, the conduit is releasably coupled with the handle so that a new conduit can be secured to the handle for use with a new patient, and the used conduit can be uncoupled thereafter, preferably by hand and without requiring the use of tools, and disposed of in preparation for use with another patient. In addition, or alternatively, the handle and the display can be releasably secured to each other so that a new handle and a new conduit can be secured to the display before use with a new patient, and thereafter the handle and the conduit can be uncoupled from the display, preferably by hand and without requiring tools, and disposed of. An inflatable balloon can be secured to the conduit, such as balloon 106, and selectively inflated when the distal end of the conduit is in the uterus, to resist fluid flow out of the uterus. The instrument can be provided with an ablation device at the distal portion of the conduit to selectively ablate at least a selected portion of the uterus under user control. Examples of ablation devices are electrode mesh structure 3340, although other types of ablation structures using heat or other means to ablate can be used instead or in addition (for example, laser light).

The medical instrument that is at least party disposable can be used in a method of distending, imaging and taking biopsy samples of a patient's uterus in a single insertion of the instrument into the uterus. The method includes: (a) inserting the distal portion of the conduit into the patient's uterus by manually manipulating the handle; (b) distending the uterus by introducing fluid under pressure into the conduit through one or more proximal ports at the proximal portion of the conduit and out of the conduit and into the uterus through one or more of the distal openings at the distal portion of the conduit; (c) while the distal portion remains inserted in the uterus, illuminating a portion of the uterus with an illumination system emitting light from the distal portion of the conduit; (d) while the distal portion remains inserted in the uterus, imaging the illuminated portion of the uterus with an imaging system secured at the distal portion of the conduit; (e) still while the distal portion remains inserted in the uterus, displaying, on a display secured to said handle, images provided by the imaging system; (f) while the distal portion remains inserted in the uterus, manipulating the distal portion of the conduit in the patient's uterus and causing the transfer of fluid and biopsy samples from the uterus into at least one of the distal openings and out of at least one of said one or more proximal ports; (g) withdrawing the conduit from the patient's uterus; and (h) disposing of at least the conduit before using at least the display for another patient. Only the conduit can be disposed of and replaced with a new one for a new patient, or both the handle and the conduit can be disposed of and replaced with a new conduit and handle for a new patient, or the entire instrument cab be disposed of and replaced with a new one for a new patient. If ablation is indicated or desired, an instrument that additionally includes an ablation structure at the dital portion can be used to ablate at least a selected portion of the uterus.

Although the foregoing has been described in some detail for purposes of clarity, it will be apparent that certain changes and modifications may be made without departing from the principles thereof. It should be noted that there are many alternative ways of implementing both the processes and apparatuses described herein, including for using the described devices or certain aspects thereof for hysteroscopy but not for endometrial biopsy, or for endometrial biopsy but not for hysteroscopy, or for endoscopy and/or biopsy other than of the uterus. For example, in some applications the device shown in FIGS. A50-A51 could also be used for taking fluid and/or fluid/tissue endometrial samples through the forward facing fluid parts. Accordingly, the present embodiments are to be considered as illustrative and not restrictive, and the body of work described herein is not to be limited to the details given herein, which may be modified within the scope and equivalents of the appended claims.

What it claimed is:

1. A low-cost medical instrument for examining a patient's uterus, which instrument includes a single-use portion that in a single insertion distends, images and biopsies a patient's uterus, said instrument comprising:

a single-use, elongated conduit having a distal portion configured and dimensioned for insertion into the patient's uterus, and a proximal portion, said conduit comprising:

a fluid hub formed at the proximal portion of the conduit;

one or more proximal ports at the fluid hub, configured to provide passage of fluid into the conduit and out of the conduit;

one or more distal openings at the distal portion of the conduit configured to provide fluid outflow from the conduit and inflow of fluid and biopsy samples into the conduit;

one or more biopsy implements at the distal end of the conduit, configured and shaped to take biopsy samples from the uterus and transfer them into the conduit;

an imaging system at the distal portion of the conduit configured to image the uterus and provide video signals;

an illumination system at the distal portion of the conduit configured to illuminate the uterus at an illumination field viewed by said imaging system; and an electrical cable extending from a proximal end of the hub to the imaging and illumination systems and configured to carry video signals and control signals;

a multiple-use handle that includes electronic and electrical components and is configured and dimensioned to be grasped by a user's hand and manipulated by the user;

a coupling formed of portions of the handle and the fluid hub and configured to directly and releasably couple the fluid hub to the handle and thus mount the conduit to the handle;

said coupling comprising (i) an extension of one of the handle and the hub and (ii) a channel in the other one of the handle and the hub, wherein the extension releasably fits in the channel;

said hub comprising an outer shell having a distal portion and a proximal portion;

a barrier fitted inside the outer shell of the fluid hub and comprising a first seal configured to keep fluid in the conduit from entering the hub in the proximal direction but allowing passage of the electrical cable from the proximal portion of the hub to the distal portion of the conduit;

said first seal being spaced in the proximal direction from said one or more proximal ports in the hub;

at least one additional seal disposed between the first seal and the handle and configured to keep fluid and tissue samples flowing in the conduit from reaching the handle, including a seal formed by an inner portion of said barrier tightly enveloping a radial extend of a proximal portion of the said cable;

whereby the handle interior is kept from contamination with fluid and tissue samples in use of the instrument to examine a patient's uterus and therefore need not be sterilized but can be simply wiped for cleaning and disinfection after the conduit is detached from the handle and disposed;

said handle comprising an integral image display and including a control system that is electrically coupled with said imaging system, the illumination system and the image display when the conduit is coupled to and mounted to the handle and is configured to selectively cause, in response to user commands entered through the handle, the illumination system to illuminate the uterus, the imaging system to provide an image of the uterus, and the display system to display the image for viewing by the user when the conduit is inserted in the patient's uterus;

wherein:
said conduit is configured to be uncoupled by hand from the handle after a single use in a patient and disposed; and the instrument is configured for a medical procedure in which said distal portion is inserted only once into the patient's uterus to provide each of (a) uterus distention by introducing fluid under positive pressure into one or more of said one or more proximal ports of the fluid hub, which fluid passes through said conduit and enters the uterus through one or more of said one or more distal openings, (b) an image of the uterus by illuminating the uterus with said illumination system and imaging the illuminated uterus with said imaging system, and (c) taking biopsy samples from the uterus by engaging the uterus with said biopsy implements and drawing fluid and biopsy samples from the uterus into the conduit through one or more of said one or more distal openings by applying negative pressure to one or more of said one or more proximal ports of the fluid hub.

2. The medical instrument of claim 1 wherein said one or more distal openings comprise plural openings.

3. The medical instrument of claim 1 wherein said one or more proximal ports comprise plural ports.

4. The medical instrument of claim 1 wherein said biopsy implements are formed at one or more of said one or more distal openings.

5. The medical instrument of claim 4 wherein said biopsy implements are formed at one of said one or more distal openings, and said biopsy implements includes a sharp edge positioned so as to facilitate collection of endometrial sample tissue by scraping.

6. The medical instrument of claim 5 wherein the one of said one or more distal openings at which sharp edge is positioned is a side-facing distal opening and is positioned on an outwardly-facing side surface of the conduit.

7. The medical instrument of claim 6 wherein one of the one or more distal openings is forward-facing and is positioned on an end of the distal portion of the conduit.

8. The medical instrument of claim 7 wherein the conduit includes first and second separate fluid channels, the first fluid channel being in fluid communication with the forward facing distal opening and the second fluid channel being in fluid communication being in fluid communication with the side-facing distal opening.

9. The medical instrument of claim 1 wherein the medical procedure for which the instrument is configured further includes collapsing the uterus to a less-distended state by at least one of (i) reducing a rate of introduction of fluid into the uterus and (ii) applying a suction of fluid from the uterus and into at least one of said one or more distal openings.

10. The medical instrument of claim 1 wherein the imaging system includes a single-chip sensor module having a color CMOS image sensor core, image sensor processing circuitry and image output interface circuitry.

11. The medical instrument of claim 1 wherein the illumination system includes one or more LEDs mounted near a distal end of the distal portion of the conduit.

12. The medical instrument of claim 1 wherein the at least one additional seal comprises a ring pressed between the fluid hub and the handle.

13. The medical instrument of claim 1 wherein said ring is an o-ring pressed between lips of the barrier and the handle.

14. The medical instrument of claim 1 in which said at least one additional seal comprises a projection extending from one of the barrier and the proximal end of the electrical cable and an indentation in the other, into which said projection tightly fits.

15. The medical instrument of claim 1 wherein said extension is a part of the hub and said channel is in the handle.

16. The medical instrument of claim 1 wherein the outer shell of the hub includes a lip tightly fitting over a distal end of the handle.

17. The medical instrument of claim 1 wherein one of the extension and the channel includes a bump and the other includes a depression in which the bump fits when the conduit is mounted to the handle.

18. The medical instrument of claim 1 wherein the at least one additional seal is spaced in the proximal direction from said one of more ports in the hub and comprises both (a) portions of the barrier and of the electrical cable fitting into each other, and (b) a seal between the distal portion of the handle and a proximal portion of the hub.

* * * * *